US012673072B2

(12) United States Patent
Veiseh et al.

(10) Patent No.: US 12,673,072 B2
(45) Date of Patent: Jul. 7, 2026

(54) ENCAPSULATED CELLS EXPRESSING IL-12 AND USES THEREOF

(71) Applicant: William Marsh Rice University, Houston, TX (US)

(72) Inventors: Omid Veiseh, Houston, TX (US); Amanda Nash, Houston, TX (US); Samira Aghlara-Fotovat, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 705 days.

(21) Appl. No.: 18/067,204

(22) Filed: Dec. 16, 2022

(65) Prior Publication Data

US 2024/0041939 A1      Feb. 8, 2024

Related U.S. Application Data

(60) Provisional application No. 63/291,129, filed on Dec. 17, 2021.

(51) Int. Cl.
| *A61K 35/36* | (2015.01) |
| *A61P 35/00* | (2006.01) |
| *C07K 14/54* | (2006.01) |
| *C12N 5/071* | (2010.01) |
| *C12N 11/08* | (2020.01) |

(52) U.S. Cl.
CPC .............. *A61K 35/36* (2013.01); *A61P 35/00* (2018.01); *C07K 14/5434* (2013.01); *C12N 5/0602* (2013.01); *C12N 11/08* (2013.01)

(58) Field of Classification Search
CPC ..................................................... A61K 35/36
See application file for complete search history.

(56) References Cited

U.S. PATENT DOCUMENTS

| 5,573,764 | A | * | 11/1996 | Sykes | .................. A61K 38/208 424/85.2 |
| 7,910,564 | B2 | * | 3/2011 | Sung | ....................... A61P 31/16 536/23.1 |
| 2003/0143642 | A1 | * | 7/2003 | Jesperson | .......... G01N 33/5436 435/7.5 |
| 2007/0269408 | A1 | | 11/2007 | Sung et al. | |
| 2014/0147437 | A1 | * | 5/2014 | Ma | ....................... C07K 16/303 424/139.1 |
| 2018/0333485 | A1 | | 11/2018 | Weiner et al. | |

(Continued)

FOREIGN PATENT DOCUMENTS

| WO | WO2001068802 A2 | 9/2001 |
| WO | WO2017201350 A1 | 11/2017 |
| WO | WO2021026484 A1 | 2/2021 |

OTHER PUBLICATIONS

Cameron, M.J. and Kelvin, D.J. Cytokines, Chemokines, and Their Receptors. Landes Biosciences, this version accessed online on May 14, 2024, 25 pages.

(Continued)

*Primary Examiner* — Mark L Shibuya
(74) *Attorney, Agent, or Firm* — Baker, Donelson, Bearman, Caldwell & Berkowitz, PC

(57) ABSTRACT

The present disclosure relates to implantable constructs (encapsulated cells) designed to deliver therapeutic reagents, such as IL-12 and/or IL-12 and methods of using the same to treat conditions, such as cancer.

18 Claims, 11 Drawing Sheets

Specification includes a Sequence Listing.

(56) References Cited

U.S. PATENT DOCUMENTS

| | | | |
|---|---|---|---|
| 2019/0184067 A1 | 6/2019 | Vegas et al. | |
| 2020/0102363 A1* | 4/2020 | Mishra | A61K 9/5123 |
| 2020/0246420 A1* | 8/2020 | Reshetnyak | A61P 35/00 |
| 2022/0143099 A1* | 5/2022 | Scadden | A61K 38/208 |
| 2024/0041755 A1* | 2/2024 | Veiseh | C12N 5/0012 |

OTHER PUBLICATIONS

Chin, J.X. et al. Codon Optimization OnLine (COOL): a web-based multi-objective optimization platform for synthetic gene design. Bioinformatics, vol. 30, Issue 15, p. 2210-2212 (2014).

COOL (Codon Optimization OnLine), webpage http://bioinfo.bti.a-star.edu.sg/COOL/, Nov. 18, 2024, 2 pages.

Grote, A. et al. JCat: a novel tool to adapt codon usage of a target gene to its potential expression host. Nucleic Acids Research, vol. 33, Issue suppl_2, pp. W526-W531 (2005).

Gutierrez-Ortega, A. et al; "Expression of a Single-Chain Human Interleukin-12 Gene In Transgenic Tobacco Plants And Functional Studies;" Biotechnology and Bioengineering, John Wiley, Hoboken, USA; vol. 85; No. 7; Feb. 4, 2004; pp. 734-740; XP071032897; ISSN: 0006-3592; DOI: 10.1002/BIT.20027.

International Search Report for PCT/US2022/081747 mailed Mar. 15, 2023, 4 pages.

JCAT (Java Codon Adaptation Tool), website http://www.jcat.de, last accessed May 14, 2024, 1 page.

Park, C. G. et al. Extended release of perioperative immunotherapy prevents tumor recurrence and eliminates metastases. Sci. Transl. Med. 10(433):eaar191, 14 pages (2018).

Written Opinion for PCT/US2022/081747 mailed Mar. 15, 2023, 6 pages.

Zheng S. et al; "Continuous Release of 1-6, Interleukin 12 From Microencapsulated 8-13, 15 Engineered Cells For Colon Cancer Therapy;" World Journal of Gastroenterology, WJG Press, CN; vol. 9; No. 5; May 15, 2003; pp. 951-955; XP001247101; ISSN:1007-9327.

* cited by examiner

SEQUENCE LISTING

```
Sequence total quantity: 11
SEQ ID NO: 1              moltype = DNA  length = 1444
FEATURE                  Location/Qualifiers
source                   1..1444
                         mol_type = other DNA
                         organism = synthetic construct
SEQUENCE: 1
atttcgcttt cattttgggc cgagctggag gcggcggggc cgtcccggaa cggctgcggc   60
cgggcacccc gggagttaat ccgaaagcgc cgcaagcccc gcgggccggc cgcaccgcac  120
gtgtcaccga gaagctgatg tagagagaga cacagaagga gacagaaagc aagagaccag  180
agtccctggga aagtcctgcc gcgcctcggg acaattataa aaatgtggcc ccctgggtca  240
gcctcccagc caccgccctc acctgccgcg gccacaggtc tgcatccagc ggctcgccct  300
gtgtccctgc agtgccggct cagcatgtgt ccagcgcgca gcctcctcct tgtggctacc  360
ctggtcctcc tggaccacct cagtttggcc agaaacctcc ccgtggccac tccagaccca  420
ggaatgttcc catgccttca ccactcccaa aacctgctga gggccgtcag caacatgctc  480
cagaaggcca gacaaactct agaattttac ccttgcactt ctgaagagat tgatcatgaa  540
gatatcacaa aagataaaac cagcacagtg gaggcctgtt taccattgga attaaccaag  600
aatgagagtt gcctaaattc cagagagacc tctttcataa ctaatgggag ttgcctggcc  660
tccagaaaga cctcttttat gatggccctg tgccttagta gtatttatga agacttgaag  720
atgtaccagg tggagttcaa gaccatgaat gcaaagcttc tgatggatcc taagaggcag  780
atctttctag atcaaaacat gctggcagtt attgatgagc tgatgcaggc cctgaatttc  840
aacagtgaga ctgtgccaca aaaatcctcc cttgaagaac cggattttta taaaactaaa  900
atcaagctct gcatacttct tcatgctttc agaattcggg cagtgactat tgatagagtg  960
atgagctatc tgaatgcttc ctaaaaagcg aggtccctcc aaaccgttgt cattttata  1020
aaactttgaa atgaggaaac tttgatagga tgtggattaa gaactaggga gggggaaaga  1080
aggatgggac tattacatcc acatgatacc tctgatcaag tatttttgac atttactgtg  1140
gataaattgt ttttaagttt tcatgaatga attgctaaga agggaaaata tccatcctga  1200
aggtgttttt cattcacttt aatagaaggg caaatattta taagctattt ctgtaccaaa  1260
gtgtttgtgg aaacaaacat gtaagcataa cttattttaa aatatttatt tatataactt  1320
ggtaatcatg aaagcatctg agctaactta tatttattta tgttatattt attaaattat  1380
ttatcaagtg tatttgaaaa atatttttaa gtgttctaaa aataaaagta ttgaattaaa  1440
gtga                                                              1444

SEQ ID NO: 2              moltype = DNA  length = 2364
FEATURE                  Location/Qualifiers
source                   1..2364
                         mol_type = other DNA
                         organism = synthetic construct
SEQUENCE: 2
agaagaaaca acatctgttt cagggccatt ggactctccg tcctgcccag agcaagatgt   60
gtcaccagca gttggtcatc tcttggtttt ccctggtttt tctggcatct cccctcgtgg  120
ccatatggga actgaagaaa gatgtttatg tcgtagaatt ggattggtat ccggatgccc  180
ctggagaaat ggtggtcctc acctgtgaca cccctgaaga agatggtatc acctggacct  240
tggaccagag cagtgaggtc ttaggctctg gcaaaaccct gaccatccaa gtcaaagagt  300
ttggagatgc tggccagtac acctgtcaca aaggaggcga ggttctaagc cattcgctcc  360
tgctgcttca caaaaaggaa gatggaattt ggtccactga tattttaaag gaccagaaag  420
aacccaaaaa taagaccttt ctaagatgcg aggccaagaa ttattctgga cgtttcacct  480
gctggtggct gacgacaatc agtactgatt tgacattcag tgtcaaaagc agcagaggct  540
cttctgaccc ccaaggggtg acgtgcggag ctgctacact ctctgcagag agagtcagag  600
gggacaacaa ggagtatgag tactcagtgg agtgccagga ggacagtgcc tgcccagctg  660
ctgaggagag tctgcccatt gaggtcatgg tggatgccgt tcacaagctc aagtatgaaa  720
actacaccag cagcttcttc atcagggaca tcatcaaacc tgacccaccc aagaacttgc  780
```

```
agctgaagcc attaaagaat tctcggcagg tggaggtcag ctgggagtac cctgacacct   840
ggagtactcc acattcctac ttctccctga cattctgcgt tcaggtccag ggcaagagca   900
agagagaaaa gaaagataga gtcttcacgg acaagacctc agccacggtc atctgccgca   960
aaaatgccag cattagcgtg cgggcccagg accgctacta tagctcatct tggagcgaat  1020
gggcatctgt gccctgcagt taggttctga tccaggatga aaatttggag gaaaagtgga  1080
agatattaag caaaatgttt aaagacacaa cggaatagac ccaaaaagat aatttctatc  1140
tgatttgctt taaaacgttt ttttaggatc acaatgatat ctttgctgta tttgtatagt  1200
tagatgctaa atgctcattg aaacaatcag ctaatttatg tatagatttt ccagctctca  1260
agttgccatg ggccttcatg ctatttaaat atttaagtaa tttatgtatt tattagtata  1320
ttactgttat ttaacgtttg tctgccagga tgtatggaat gtttcatact cttatgacct  1380
gatccatcag gatcagtccc tattatgcaa aatgtgaatt taattttatt tgtactgaca  1440
acttttcaag caaggctgca agtacatcag ttttatgaca atcaggaaga atgcagtgtt  1500
ctgataccag tgccatcata cacttgtgat ggatgggaac gcaagagata cttacatgga  1560
aacctgacaa tgcaaacctg ttgagaagat ccaggagaac aagatgctag ttcccatgtc  1620
tgtgaagact tcctggagat ggtgttgata aagcaattta gggccactta cacttctaag  1680
caagtttaat ctttggatgc ctgaatttta aaagggctag aaaaaaatga ttgaccagcc  1740
tgggaaacat aacaagaccc cgtctctaca aaaaaaattt aaaattagcc aggcgtggtg  1800
gctcatgctt gtggtcccag cgttcagga ggatgaggca ggaggatctc ttgagcccag  1860
gaggtcaagg ctatggtgag ccgtgattgt gccactgcat accagcctag gtgacagaat  1920
gagaccctgt ctcaaaaaaa aaaatgattg aaattaaaat tcagctttag cttccatggc  1980
agtcctcacc cccacctctc taaaagacac aggaggatga cacagaaaca ccgtaagtgt  2040
ctggaaggca aaaagatctt aagattcaag agagaggaca agtagttatg gctaaggaca  2100
tgaaattgtc agaatggcag gtggcttctt aacagccctg tgagaagcag acagatgcaa  2160
agaaaatctg gaatcccttt ctcattagca tgaatgaacc tgatacacaa ttatgaccag  2220
aaaatatggc tccatgaagg tgctactttt aagtaatgta tgtgcgctct gtaaagtgat  2280
tacatttgtt tcctgtttgt ttatttattt atttatttt gcattctgag ctgaactaa  2340
taaaaactct tctttgtaat cata                                          2364

SEQ ID NO: 3              moltype = AA  length = 219
FEATURE                  Location/Qualifiers
source                   1..219
                         mol_type = protein
                         organism = synthetic construct
SEQUENCE: 3
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNAS                          219

SEQ ID NO: 4              moltype = AA  length = 328
FEATURE                  Location/Qualifiers
source                   1..328
                         mol_type = protein
                         organism = synthetic construct
SEQUENCE: 4
MCHQQLVISW FSLVFLASPL VAIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCS                                      328

SEQ ID NO: 5              moltype = AA  length = 335
FEATURE                  Location/Qualifiers
source                   1..335
                         mol_type = protein
                         organism = synthetic construct
SEQUENCE: 5
MCPQKLTISW FAIVLLVSPL MAMWELEKDV YVVEVDWTPD APGETVNLTC DTPEEDDITW    60
TSDQRHGVIG SGKTLTITVK EFLDAGQYTC HKGGETLSHS HLLLHKKENG IWSTEILKNF   120
KNKTFLKCEA PNYSGRFTCS WLVQRNMDLK FNIKSSSSSP DSRAVTCGMA SLSAEKVTLD   180
QRDYEKYSVS CQEDVTCPTA EETLPIELAL EARQQNKYEN YSTSFFIRDI IKPDPPKNLQ   240
MKPLKNSQVE VSWEYPDSWS TPHSYFSLKF FVRIQRKKEK MKETEEGCNQ KGAFLVEKTS   300
TEVQCKGGNV CVQAQDRYYN SSCSKWACVP CRVRS                              335

SEQ ID NO: 6              moltype = DNA  length = 462
FEATURE                  Location/Qualifiers
source                   1..462
                         mol_type = other DNA
                         organism = synthetic construct
SEQUENCE: 6
atgtacagga tgcaactcct gtcttgcatt gcactaagtc ttgcacttgt cacaaacagt    60
gcacctactt caagttctac aaagaaaaca cagctacaac tggagcattt actgctggat   120
ttacagatga ttttgaatgg aattaataat tacaagaatc ccaaactcac caggatgctc   180
acatttaagt tttacatgcc caagaaggcc acagaactga aacatcttca gtgtctagaa   240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt ctgaacagaa   420
tggattacct ttgtcaaag catcatctca acactgactt ga                      462
```

-continued

```
SEQ ID NO: 7            moltype = DNA  length = 462
FEATURE                 Location/Qualifiers
source                  1..462
                        mol_type = other DNA
                        organism = synthetic construct
SEQUENCE: 7
atgtaccgga tgcagctgct gtcctgcatc gcactgtccc tcgccctggt gacaaattct  60
gcccccacct cctccagcac aaaaaagacc cagttgcagc tggagcacct gctgctggat  120
ctgcagatga tcctgaatgg catcaataac tacaaaaacc ctaaactgac cagaatgctg  180
acctttaaat tttacatgcc taaaaaggca accgagctga agcacctgca gtgcctggaa  240
gaggaactga agcccctgga ggaggtgctg aacctggccc agagcaagaa cttttcacctg  300
cggccccgcg acctgatcag caacatcaac gtgatcgtgc tggagctgaa gggcagtgaa  360
accacattca tgtgcgagta cgccgacgag accgccacaa tcgtggagtt cctgaacaga  420
tggatcacat tctgtcagtc catcattagc acactgacct aa                      462

SEQ ID NO: 8            moltype = DNA  length = 462
FEATURE                 Location/Qualifiers
source                  1..462
                        mol_type = other DNA
                        organism = synthetic construct
SEQUENCE: 8
atgtaccgca tgcagctgct gagctgcatc gccctgagcc tggccctggt gaccaacagc  60
gcccccacca gcagcagcac caagaagacc cagctgcagc tggagcacct gctgctggac  120
ctgcagatga tcctgaacgg catcaacaac tacaagaacc ccaagctgac ccgcatgctg  180
accttcaagt tctacatgcc caagaaggcc accgagctga agcacctgca gtgcctggag  240
gaggagctga agcccctgga ggaggtgctg aacctggccc agagcaagaa cttccacctg  300
cgccccgcg acctgatcag caacatcaac gtgatcgtgc tggagctgaa gggcagcgag  360
accaccttca tgtgcgagta cgccgacgag accgccacca tcgtggagtt cctgaaccgc  420
tggatcacct tctgccagag catcatcagc accctgacct aa                      462

SEQ ID NO: 9            moltype = DNA  length = 459
FEATURE                 Location/Qualifiers
source                  1..459
                        mol_type = other DNA
                        organism = synthetic construct
SEQUENCE: 9
atgtatagga tgcagctgct ctcttgtatc gcgttgtctc tggctttggt gactaactca  60
gctcccacgt ccagcagtac caaaaagacc cagctgcagc tggaacatct tctgttggat  120
ctgcaaatga tactgaatgg gatcaacaac tataaaaacc caaaactgac tagaatgctg  180
actttcaagt tctacatgcc taaaaaggca acagaattga agcaccttca gtgcctggag  240
gaggagctta agcccctgga ggaggtgctg aatctggccc aaagtaagaa ttttcatctg  300
cgacccaggg atctgatcag taatatcaat gtgatcgtcc tggagctgaa gggcagtgag  360
accacgttta tgtgtgaata cgcagacgaa accgccacta tcgttgaatt cttgaacagg  420
tggatcacct tttgtcagag tatcatcagc accctcact                         459

SEQ ID NO: 10           moltype = DNA  length = 462
FEATURE                 Location/Qualifiers
source                  1..462
                        mol_type = other DNA
                        organism = synthetic construct
SEQUENCE: 10
atgtacagaa tgcagctgct gagctgcatc gccctgagcc tggccctggt gaccaacagc  60
gcccccacaa gcagcagcac caagaagaca cagctgcagc tggagcacct gctgctggac  120
ctgcagatga tcctgaacgg catcaacaac tacaagaacc ccaagctgac aagaatgctg  180
accttcaagt tctacatgcc caagaaggcc accgagctga agcacctgca gtgcctggag  240
gaggagctga agcccctgga gaggtgctg aacctggctc agagcaagaa cttccacctg  300
agacctagag acctgatcag caacatcaac gtgatcgtgc tggagctgaa gggcagcgag  360
accaccttca tgtgcgagta cgccgacgag accgccacca tcgtggagtt cctgaacaga  420
tggatcacct tctgtcagag catcatcagc accctgacct ga                      462

SEQ ID NO: 11           moltype = AA  length = 153
FEATURE                 Location/Qualifiers
source                  1..153
                        mol_type = protein
                        organism = synthetic construct
SEQUENCE: 11
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                                153
```

ENCAPSULATED CELLS EXPRESSING IL-12 AND USES THEREOF

CROSS-REFERENCE TO RELATED APPLICATIONS

This application claims priority to U.S. Provisional Application No. 63/291,129, filed Dec. 17, 2021, which is hereby incorporated by reference in its entirety.

BACKGROUND

Reference to Sequence Listing Submitted Electronically

This instant application contains a Sequence Listing which has been submitted electronically in XML file format and is hereby incorporated by reference in its entirety. Said XML copy, created on Dec. 9, 2022, is named "258717 000801 Seq.XML" and is 17,695 bytes in size.

FIELD

The present disclosure relates to the fields of biology, medicine, bioengineering and medicals devices. More particular, it relates to the development and use of implantable constructs designed to deliver antigenic therapeutic reagents to a subject and protect them from immune responses generated by the host. In particular, the constructs are designed to degrade over time or upon a particular signal, thereby providing control of the length of time the therapeutic agent is delivered to the subject.

RELATED ART

Advances in biomedical research have led to methods for localized and targeted therapies for the treatment of diseases, such as cancer. However, in many instances, the percentage of patients responsive to these approaches remain modest (Park et al., Sci. Transl. Med. 10(433) 2018).

One approach involves the use of implantable devices to deliver therapeutic agents, however, a fundamental barrier to successful device-based therapies is the inability to deliver a sustained amount of therapeutics that do not have a systemic toxic impact on the subject. Thus, there is a need for identifying new compositions and methods to enhance the delivery, distribution, and/or efficacy of therapeutic agents.

SUMMARY

In some embodiments, populations of encapsulated cells comprising a plurality of oligonucleotide molecules encoding a IL-12 polypeptide are provided. In some embodiments, the IL-12 polypeptide is a native human IL-12 polypeptide, a recombinant IL-12 polypeptide, or an IL-12 mutein polypeptide. In some embodiments, the native human IL-12 polypeptide is a heterodimeric complex comprising a native human IL-12(p35) polypeptide and a native human IL-12 (p40) polypeptide. In some embodiments, the plurality of oligonucleotide molecules encodes the native human IL-12 (p35) polypeptide and the native human IL-12(p40) polypeptide. In some embodiments, the expressed IL-12(p35) polypeptide and the expressed IL-12(p40) polypeptide form a heterodimeric complex. In some embodiments, the oligonucleotide encoding the native human IL-12(p35) polypeptide comprises a sequence of SEQ ID NO: 1. In some embodiments, the oligonucleotide encoding the native human IL-12(p40) polypeptide comprises a sequence of SEQ ID NO: 2. In some embodiment, the IL-12(p40) mutein polypeptide comprises a mutation selected from N222L or N222Q as compared to SEQ ID NO: 4.

In some embodiments, pharmaceutical compositions comprising the population of encapsulated cells provided herein are provided.

In some embodiment, methods of treating a tumor, such as a pancreatic tumor, in a subject, the method comprising implanting in the intraperitoneal space of the subject a pharmaceutical composition comprising a plurality of encapsulated cells (e.g., a capsule), provided herein, to the subject to treat the cancer are provided.

In some embodiments, methods of reducing tumor burden, such as a pancreatic tumor, in a subject, the method comprising implanting in the intraperitoneal space of the subject a pharmaceutical composition comprising a plurality of encapsulated cells (e.g., a capsule), provided herein, to the subject to treat the cancer are provided.

In some embodiments, methods of treating a tumor, such as a melanoma tumor, in a subject, the method comprising implanting in the subcutaneous space of the subject a pharmaceutical composition comprising a plurality of encapsulated cells (e.g., a capsule), provided herein, to the subject to treat the cancer are provided.

In some embodiments, methods of reducing tumor burden, such as a melanoma tumor, in a subject, the method comprising implanting in the subcutaneous space of the subject a pharmaceutical composition comprising a plurality of encapsulated cells (e.g., a capsule), provided herein, to the subject to treat the cancer are provided.

In some embodiments, methods of treating a tumor in a subject by generating memory immunity are provided for herein. In some embodiments, the method comprises implanting a pharmaceutical composition comprising the population of encapsulated cells as provided for herein.

In some embodiments, methods of selectively activating CD8 positive effector T cells are provided. In some embodiments, the method comprises implanting a pharmaceutical composition comprising a population of encapsulated cells as provided for herein.

In some embodiments, methods of increasing interferon gamma (IFN-$\gamma$) in a subject are provided. In some embodiments, the method comprising implanting or administering pharmaceutical composition comprising a population of encapsulated cells as provided for herein.

In some embodiments, methods of preventing or inhibiting fibrosis of the capsule encapsulating cells implanted in a subject are provided. In some embodiments, the method comprises having the implanted encapsulated cells express IL-12 or are exposing the implanted encapsulated cells to IL-12 in the location of implantation. In some embodiments, the inhibition or prevention of fibrosis is complete. In some embodiments, the inhibition or prevention of fibrosis of the capsule is partial. In some embodiments, the fibrosis that occurs is less than would occur without the expression of IL-12 from the capsule or exposure of the capsule to IL-12. In some embodiments, the fibrosis that occurs is not sufficient to completely block secretion of the protein of interest or heterologous protein from the encapsulated cells. In some embodiments, the protein of interest is IL-12. In some embodiments, the anti-fibrotic effect is effectuated on a capsule that encapsulates cells that expresses a protein that is not IL-12, such as IL-2 or another cytokine or expressed by the cells. Non-limiting examples are provided for herein. This anti-fibrotic effect can be said to occur both "cis" on the same capsule expressing IL-12, but can also act "trans" on a capsule that does not express IL-12.

In some embodiments, methods of preparing encapsulated cells producing a recombinant protein are provided. In some embodiments, the method comprises feeding through a coaxial needle a first composition comprising a polymeric hydrogel and a second composition comprising cells to be encapsulated suspended in a polymeric hydrogel to drop into a crosslinking solution to form the encapsulated cells, wherein the crosslinking solution comprises a sugar alcohol, a buffer, a metal salt, and a surfactant.

In some embodiments, suspensions of encapsulated cells are provided. In some embodiments, the suspension comprises a population of encapsulated cells as provided for herein, wherein the encapsulated cells are encapsulated by a polymeric hydrogel, and the suspension a crosslinking solution that comprises a sugar alcohol, a buffer, a metal salt, and a surfactant.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

Figure 1:
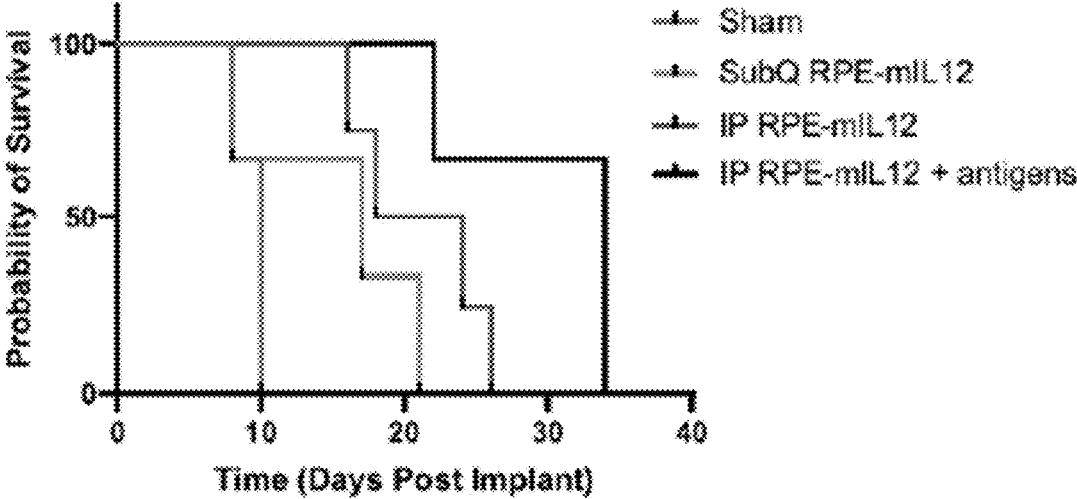
FIG. 1 illustrates survival curves (top panel) and tumor growth curves (bottom panel) for melanoma B16F10 mice threated subcutaneously or intraperitoneally with the encapsulated cells disclosed herein or sham surgery.
Figure 1:
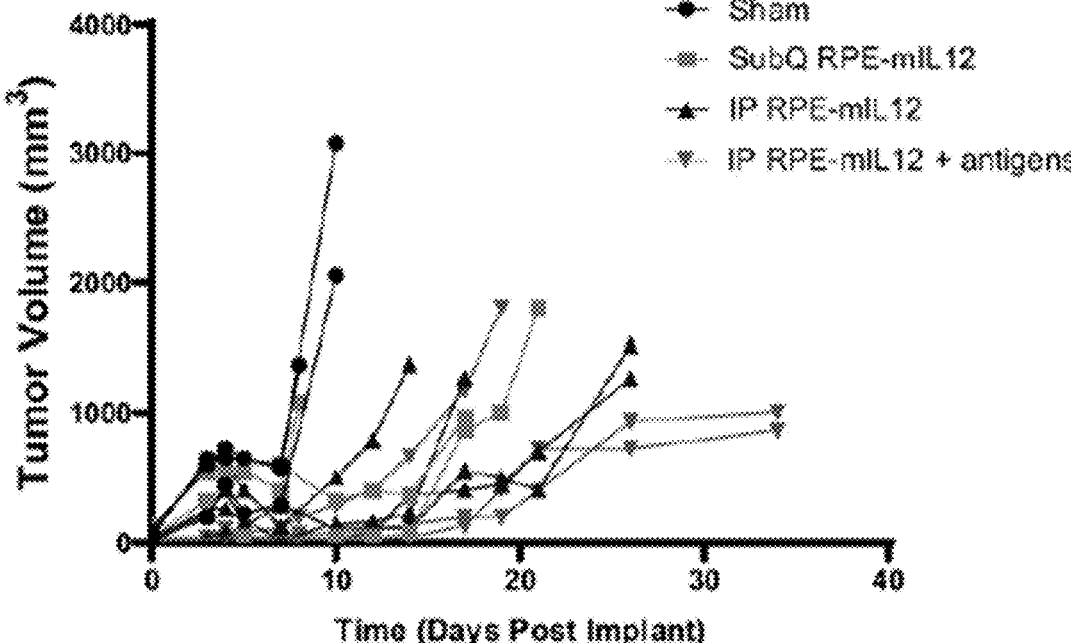

The present disclosure features implantable constructs for delivery of native human IL-12 to a subject in a controlled release manner, and related methods of use thereof. These embodiments will be described below in more detail.

A. DEFINITIONS

"Cell," as used herein, refers to an individual cell. In some embodiments, a cell is a primary cell or is derived from a cell culture. In some embodiments, a cell is a stem cell or is derived from a stem cell. A cell may be xenogeneic, autologous, or allogeneic. In some embodiments, a cell is engineered (e.g., genetically engineered) or is not engineered (e.g., not genetically engineered). In some embodiments, the cell is an APRE-19 cell. In some embodiments, the cell expresses native human IL-12 protein.

"Prevention," "prevent," and "preventing" as used herein refers to a treatment that comprises administering or applying a therapy, e.g., administering an implantable construct (e.g., as described herein) comprising a therapeutic agent (e.g., a therapeutic agent described herein) prior to the onset of a disease or condition in order to preclude the physical manifestation of said disease or condition. In some embodiments, "prevention," "prevent," and "preventing" require that signs or symptoms of the disease or condition have not yet developed or have not yet been observed. In some embodiments, treatment comprises prevention and in other embodiments it does not. In some embodiments, the prevention is the prevention of the recurrence of a disease, such as a tumor (cancer) after the tumor or cancer has been eradicated by an initial treatment.

"Subject," as used herein, refers to the recipient of the implantable construct described herein. The subject may include a human and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development (e.g., a male or female of any age group, e.g., a pediatric subject (e.g., infant, child, adolescent) or adult subject (e.g., young adult, middle-aged adult, or senior adult). A non-human animal may be a transgenic animal.

"Treatment," "treat," and "treating," as used herein, refer to reversing, alleviating, delaying the onset of, or inhibiting the progress of one or more of a symptom, manifestation, or underlying cause of a disease or condition. (e.g., as described herein), e.g., by administering or applying a therapy, e.g., administering an implantable construct comprising a therapeutic agent (e.g., a therapeutic agent described herein). In some embodiments, treating comprises reducing, reversing, alleviating, delaying the onset of, or inhibiting the progress of a symptom of a disease, disorder, or condition. In some embodiments, treating comprises reducing, reversing, alleviating, delaying the onset of, or inhibiting the progress of a manifestation of a disease or condition. In some embodiments, treating comprises reducing, reversing, alleviating, reducing, or delaying the onset of, an underlying cause of a disease or condition. In some embodiments, "treatment," "treat," and "treating" require that signs or symptoms of the disease or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence. Treatment may also be continued after symptoms have resolved, for example, to delay or prevent recurrence. In some embodiments, treatment comprises prevention and in other embodiments it does not.

B. CELLS

Implantable constructs described herein may contain a cell, for example, an engineered cell. A cell be derived from any mammalian organ or tissue, including the brain, nerves, ganglia, spine, eye, heart, liver, kidney, lung, spleen, bone, thymus, lymphatic system, skin, muscle, pancreas, stomach, intestine, blood, ovary, uterus, or testes. In some embodiments, the cell is a APRE-19 cell. The implantable constructs can be referred to as a capsule. The capsule is the "shell" that encapsulates a population of cells. As provided for herein, the cells can be engineered to express a protein that is expressed from a heterologous nucleic acid molecule (exogenously introduced into the cell).

A cell may be derived from a donor (e.g., an allogeneic cell), derived from a subject (e.g., an autologous cell), or from another species (e.g., a xenogeneic cell). In some embodiments, a cell can be grown in cell culture, or prepared from an established cell culture line, or derived from a donor (e.g., a living donor or a cadaver). In some embodiments, a cell is genetically engineered. In another embodiment, a cell is not genetically engineered. A cell may include a stem cell, such as a reprogrammed stem cell, or an induced pluripotent cell. Exemplary cells include mesenchymal stem cells (MSCs), fibroblasts (e.g., primary fibroblasts). HEK cells (e.g., HEK293T), Jurkat cells, HeLa cells, retinal pigment epithelial (RPE) cells, HUVEC cells, NIH3T3 cells, CHO-K1 cells, COS-1 cells, COS-7 cells, PC-3 cells, HCT 116 cells, A549MCF-7 cells, HuH-7 cells, U-2 OS cells, HepG2 cells, Neuro-2a cells, and SF9 cells. In some embodiments, a cell for use in an implantable construct is an RPE cell.

A cell included in an implantable construct may produce or secrete a therapeutic agent, such as a native human IL-12. In some embodiments, the native human IL-12 is a heterodimeric complex comprising a native human IL-12(p35) and a native human IL-12(p40). In some embodiments, the therapeutic agent us a recombinant IL-12. In some embodiments, the recombinant IL-12 is a heterodimeric complex comprising a recombinant IL-12(p35) and a recombinant IL-12(p40). In some embodiments, the recombinant IL-12 is a heterodimeric complex comprising a native human IL-12 (p35) and a recombinant IL-12(p40). In some embodiments, the recombinant IL-12 is a heterodimeric complex comprising a recombinant IL-12(p35) and a native human IL-12 (p40). In some embodiments, the therapeutic agent us an IL-12 mutein. In some embodiments, the IL-12 mutein is a heterodimeric complex comprising an IL-12(p35) mutein and an IL-12(p40) mutein. In some embodiments, the IL-12 mutein is a heterodimeric complex comprising a native human IL-12(p35) and an IL-12(p40) mutein. In some embodiments, the IL-12 mutein is a heterodimeric complex comprising an IL-12(p35) mutein and a native human IL-12 (p40). In some embodiments, the IL-12 mutein is as provided herein. In some embodiments, a cell included in an implantable construct may produce or secrete a single type of therapeutic agent or a plurality of therapeutic agents. In some embodiments, the plurality of therapeutic agents comprises a IL-12, as provided herein, and a IL-2, as provided herein. In some embodiments, an implantable construct may comprise a cell that is transduced or transfected with a nucleic acid (e.g., a vector) comprising an expression sequence of a therapeutic agent. For example, a cell may be transduced or transfected with a lentivirus. A nucleic acid introduced into a cell (e.g., by transduction or transfection) may be incorporated into a nucleic acid delivery system, such as a plasmid, or may be delivered directly. In some embodiments, a nucleic acid introduced into a cell (e.g., as part of a plasmid) may include a region to enhance expression of the therapeutic agent and/or to direct targeting or secretion, for example, a promoter sequence, an activator sequence, or a cell-signaling peptide, or a cell export peptide. Exemplary promoters include EF-1a, CMV, Ubc, hPGK, VMD2, and CAG. Exemplary activators include the TET1 catalytic domain, P300 core, VPR, rTETR, Cas9 (e.g., from *S. pyogenes* or *S. aureus*), and Cpf1 (e.g., from *L. bacterium*). An implantable construct described herein may comprise a cell or a plurality of cells. In the case of a plurality of cells, the concentration and total cell number may be varied depending on a number of factors, such as cell type, implantation location, and expected lifetime of the implantable construct. In some embodiments, the total number of cells included in an implantable construct is greater than about 2, 4, 6, 8, 10, 20, 30, 40, 50, 75, 100, 200, 250, 500, 750, 1000, 1500, 2000, 5000, 10000, or more. In some embodiments, the implantable construct comprises about 10000 to about 50000 cells. In some embodiments, the implantable construct comprises about 10000 to about 40000 cells. In some embodiments, the implantable construct comprises about 10000 to about 30000 cells. In some embodiments, the implantable construct comprises about 10000 to about 20000 cells. In some embodiments, the implantable construct comprises about 20000 to about 40000 cells. In some embodiments, the implantable construct comprises about 25000 to about 35000 cells. In some embodiments, the implantable construct comprises about 30000 cells. In some embodiments, the implantable construct comprises about 40000 cells. In some embodiments, the implantable construct comprises about 50000 cells. In some embodiments, the implantable construct comprises about 10000 cells. In some embodiments, the implantable construct comprises about 20000 cells. In some embodiments, the total number of cells included in an implantable construct is greater than about $1.0 \times 10^2$, $1.0 \times 10^3$, $1.0 \times 10^4$, $1.0 \times 10^5$, $1.0 \times 10^6$, $1.0 \times 10^7$, $1.0 \times 10^8$, $1.0 \times 10^9$, $1.0 \times 10^{10}$, or more. In some embodiments, the total number of cells included in an implantable construct is less than about than about 50000, 40000, 30000, 20000, 10000, 5000, 2500, 2000, 1500, 1000, 750, 500, 250, 200, 100, 75, 50, 40, 30, 20, 10, 8, 6, 4, 2, or less. In some embodiments, the total number of cells included in an implantable construct is less than about $1.0 \times 10^{10}$, $1.0 \times 10^9$, $1.0 \times 10^8$, $1.0 \times 10^7$, $1.0 \times 10^6$, $1.0 \times 10^5$, $1.0 \times 10^4$, $1.0 \times 10^3$, $1.0 \times 10^2$, or less. In some embodiments, a plurality of cells is present as an aggregate. In some embodiments, a plurality of cells is present as a cell dispersion.

Specific features of a cell contained within an implantable construct may be determined, e.g., prior to and/or after incorporation into the implantable construct. For example, cell viability, cell density, or cell expression level may be assessed. In some embodiments, cell viability, cell density, and cell expression level may be determined using standard techniques, such as cell microscopy, fluorescence microscopy, histology, or biochemical assay.

C. THERAPEUTIC AGENTS

An implantable construct described herein may contain a therapeutic agent, for example, produced or secreted by a cell, such as a native human IL-12. In some embodiments, the therapeutic agent is a recombinant IL-12. In some embodiments, the therapeutic agent is an IL-12 mutein. In some embodiments, the therapeutic agent is a native human IL-12(p35). In some embodiments, the therapeutic agent is a native human IL-12(p40). In some embodiments, the therapeutic agent is an IL-12(p35) mutein. In some embodiments, the therapeutic agent is an IL-12(p40) mutein. In some embodiments, the therapeutic agent is a recombinant IL-12(p35). In some embodiments, the therapeutic agent is a recombinant IL-12(p40). In some embodiments, the therapeutic agent is a recombinant IL-12. In some embodiments, the therapeutic agent is an IL-12 mutein. In some embodiments, an implantable construct described herein may contain a plurality of therapeutic agents, for example, produced or secreted by a population of cells, such as native human IL-12(p35) and native human IL-12(p40). A therapeutic agent may include a nucleic acid encoding the protein (e.g., an RNA, a DNA, or an oligonucleotide), a protein (e.g., an antibody, enzyme, cytokine, hormone, receptor) that is secreted from the cell, and the like. In some embodiments, the implantable construct comprises a cell or a plurality of cells that are genetically engineered to produce or secrete a therapeutic agent. In some embodiments, the implantable construct comprises a cell or a plurality of cells that are genetically engineered to produce or secrete a plurality of therapeutic agents.

In some embodiments, native human IL-12 refers to a IL-12(p70), or a heterodimeric complex comprising native human IL-12(p35) and native human IL-12(p40). Without wishing to be bound to a particular theory, when the IL-12 (p35) subunit and the IL-12(p40) subunit are expressed they interact with each other to form a heterodimeric complex comprising the IL-12(p'70), or as referred to herein, IL-12.

In some embodiments, native human IL-12(p35) refers to a protein encoded by a nucleic acid sequence comprising:

```
                                              (SEQ ID NO: 1)
ATTTCGCTTTCATTTTGGGCCGAGCTGGAGGCGGCGGGGC

CGTCCCGGAACGGCTGCGGCCGGGCACCCCGGGAGTTAAT

CCGAAAGCGCCGCAAGCCCCGCGGGCCGGCCGCACCGCAC

GTGTCACCGAGAAGCTGATGTAGAGAGAGACACAGAAGGA

GACAGAAAGCAAGAGACCAGAGTCCCGGGAAAGTCCTGCC

GCGCCTCGGGACAATTATAAAAATGTGGCCCCCTGGGTCA

GCCTCCCAGCCACCGCCCTCACCTGCCGCGGCCACAGGTC

TGCATCCAGCGGCTCGCCCTGTGTCCCTGCAGTGCCGGCT

CAGCATGTGTCCAGCGCGCAGCCTCCTCCTTGTGGCTACC

CTGGTCCTCCTGGACCACCTCAGTTTGGCCAGAAACCTCC

CCGTGGCCACTCCAGACCCAGGAATGTTCCCATGCCTTCA

CCACTCCCAAAACCTGCTGAGGGCCGTCAGCAACATGCTC

CAGAAGGCCAGACAAACTCTAGAATTTTACCCTTGCACTT

CTGAAGAGATTGATCATGAAGATATCACAAAAGATAAAAC

CAGCACAGTGGAGGCCTGTTTACCATTGGAATTAACCAAG

AATGAGAGTTGCCTAAATTCCAGAGAGACCTCTTTCATAA

CTAATGGGAGTTGCCTGGCCTCCAGAAAGACCTCTTTTAT

GATGGCCCTGTGCCTTAGTAGTATTTATGAAGACTTGAAG

ATGTACCAGGTGGAGTTCAAGACCATGAATGCAAAGCTTC

TGATGGATCCTAAGAGGCAGATCTTTCTAGATCAAACAT

GCTGGCAGTTATTGATGAGCTGATGCAGGCCCTGAATTTC

AACAGTGAGACTGTGCCACAAAAATCCTCCCTTGAAGAAC

CGGATTTTTATAAAACTAAAATCAAGCTCTGCATACTTCT

TCATGCTTTCAGAATTCGGGCAGTGACTATTGATAGAGTG

ATGAGCTATCTGAATGCTTCCTAAAAAGCGAGGTCCCTCC

AAACCGTTGTCATTTTTATAAAACTTTGAAATGAGGAAAC

TTTGATAGGATGTGGATTAAGAACTAGGGAGGGGGAAAGA

AGGATGGGACTATTACATCCACATGATACCTCTGATCAAG

TATTTTTGACATTTACTGTGGATAAATTGTTTTTAAGTTT

TCATGAATGAATTGCTAAGAAGGGAAAATATCCATCCTGA

AGGTGTTTTTCATTCACTTTAATAGAAGGGCAAATATTTA

TAAGCTATTTCTGTACCAAAGTGTTTGTGGAAACAAACAT

GTAAGCATAACTTATTTTAAAATATTTATTTATATAACTT

GGTAATCATGAAAGCATCTGAGCTAACTTATATTTATTTA

TGTTATATTTATTAAATTATTTATCAAGTGTATTTGAAAA

ATATTTTTAAGTGTTCTAAAAATAAAAGTATTGAATTAAA

GTGA.
```

In some embodiments, native human IL-12(p40) refers to a protein encoded by a nucleic acid sequence comprising:

```
                                      (SEQ ID NO: 2)
AGAAGAAACAACATCTGTTTCAGGGCCATTGGACTCTCCG

TCCTGCCCAGAGCAAGATGTGTCACCAGCAGTTGGTCATC

TCTTGGTTTTCCCTGGTTTTTCTGGCATCTCCCCTCGTGG

CCATATGGGAACTGAAGAAAGATGTTTATGTCGTAGAATT

GGATTGGTATCCGGATGCCCCTGGAGAAATGGTGGTCCTC

ACCTGTGACACCCCTGAAGAAGATGGTATCACCTGGACCT

TGGACCAGAGCAGTGAGGTCTTAGGCTCTGGCAAAACCCT

GACCATCCAAGTCAAAGAGTTTGGAGATGCTGGCCAGTAC

ACCTGTCACAAAGGAGGCGAGGTTCTAAGCCATTCGCTCC

TGCTGCTTCACAAAAAGGAAGATGGAATTTGGTCCACTGA

TATTTTAAAGGACCAGAAAGAACCCAAAAATAAGACCTTT

CTAAGATGCGAGGCCAAGAATTATTCTGGACGTTTCACCT

GCTGGTGGCTGACGACAATCAGTACTGATTTGACATTCAG

TGTCAAAAGCAGCAGAGGCTCTTCTGACCCCCAAGGGGTG

ACGTGCGGAGCTGCTACACTCTCTGCAGAGAGAGTCAGAG

GGGACAACAAGGAGTATGAGTACTCAGTGGAGTGCCAGGA

GGACAGTGCCTGCCCAGCTGCTGAGGAGAGTCTGCCCATT

GAGGTCATGGTGGATGCCGTTCACAAGCTCAAGTATGAAA

ACTACACCAGCAGCTTCTTCATCAGGGACATCATCAAACC

TGACCCACCCAAGAACTTGCAGCTGAAGCCATTAAAGAAT

TCTCGGCAGGTGGAGGTCAGCTGGGAGTACCCTGACACCT

GGAGTACTCCACATTCCTACTTCTCCCTGACATTCTGCGT

TCAGGTCCAGGGCAAGAGCAAGAGAGAAAAGAAAGATAGA

GTCTTCACGGACAAGACCTCAGCCACGGTCATCTGCCGCA

AAAATGCCAGCATTAGCGTGCGGGCCCAGGACCGCTACTA

TAGCTCATCTTGGAGCGAATGGGCATCTGTGCCCTGCAGT

TAGGTTCTGATCCAGGATGAAAATTTGGAGGAAAAGTGGA

AGATATTAAGCAAAATGTTTAAAGACACAACGGAATAGAC

CCAAAAAGATAATTTCTATCTGATTTGCTTTAAAACGTTT

TTTTAGGATCACAATGATATCTTTGCTGTATTTGTATAGT

TAGATGCTAAATGCTCATTGAAACAATCAGCTAATTTATG

TATAGATTTTCCAGCTCTCAAGTTGCCATGGGCCTTCATG

CTATTTAAATATTTAAGTAATTTATGTATTTATTAGTATA

TTACTGTTATTTAACGTTTGTCTGCCAGGATGTATGGAAT

GTTTCATACTCTTATGACCTGATCCATCAGGATCAGTCCC

TATTATGCAAAATGTGAATTTAATTTTATTTGTACTGACA

ACTTTTCAAGCAAGGCTGCAAGTACATCAGTTTTATGACA

ATCAGGAAGAATGCAGTGTTCTGATACCAGTGCCATCATA
```

```
                           -continued
CACTTGTGATGGATGGGAACGCAAGAGATACTTACATGGA

AACCTGACAATGCAAACCTGTTGAGAAGATCCAGGAGAAC

AAGATGCTAGTTCCCATGTCTGTGAAGACTTCCTGGAGAT

GGTGTTGATAAAGCAATTTAGGGCCACTTACACTTCTAAG

CAAGTTTAATCTTTGGATGCCTGAATTTTAAAAGGGCTAG

AAAAAAATGATTGACCAGCCTGGGAAACATAACAAGACCC

CGTCTCTACAAAAAAAATTTAAAATTAGCCAGGCGTGGTG

GCTCATGCTTGTGGTCCCAGCTGTTCAGGAGGATGAGGCA

GGAGGATCTCTTGAGCCCAGGAGGTCAAGGCTATGGTGAG

CCGTGATTGTGCCACTGCATACCAGCCTAGGTGACAGAAT

GAGACCCTGTCTCAAAAAAAAAAAATGATTGAAATTAAAAT

TCAGCTTTAGCTTCCATGGCAGTCCTCACCCCCACCTCTC

TAAAAGACACAGGAGGATGACACAGAAACACCGTAAGTGT

CTGGAAGGCAAAAAGATCTTAAGATTCAAGAGAGAGGACA

AGTAGTTATGGCTAAGGACATGAAATTGTCAGAATGGCAG

GTGGCTTCTTAACAGCCCTGTGAGAAGCAGACAGATGCAA

AGAAAATCTGGAATCCCTTTCTCATTAGCATGAATGAACC

TGATACACAATTATGACCAGAAAATATGGCTCCATGAAGG

TGCTACTTTTAAGTAATGTATGTGCGCTCTGTAAAGTGAT

TACATTTGTTTCCTGTTTGTTTATTTATTTATTTATTTTT

GCATTCTGAGGCTGAACTAATAAAAACTCTTCTTTGTAAT

CATA
```

In some embodiments, the native human protein produced by the cell comprises a polypeptide comprising a first polypeptide comprising the sequence of:

```
                                      (SEQ ID NO: 3)
MCPARSLLLVATLVLLDHLSLARNLPVATPDPGMFPCLHHSQNLLRAV

SNMLQKARQTLEFYPCTSEEIDHEDITKDKTSTVEACLPLELTKNESC

LNSRETSFITNGSCLASRKTSFMMALCLSSIYEDLKMYQVEFKTMNAK

LLMDPKRQIFLDQNMLAVIDELMQALNENSETVPQKSSLEEPDFYKTK

IKLCILLHAFRIRAVTIDRVMSYLNAS;
``` and a second polypeptide comprising the sequence of:

```
                                      (SEQ ID NO: 4)
MCHQQLVISWFSLVFLASPLVAIWELKKDVYVVELDWYPDAPGEMVVL

TCDTPEEDGITWTLDQSSEVLGSGKTLTIQVKEFGDAGQYTCHKGGEV

LSHSLLLLHKKEDGIWSTDILKDQKEPKNKTFLRCEAKNYSGRFTCWW

LTTISTDLTFSVKSSRGSSDPQGVTCGAATLSAERVRGDNKEYEYSVE

CQEDSACPAAEESLPIEVMVDAVHKLKYENYTSSFFIRDIIKPDPPKN

LQLKPLKNSRQVEVSWEYPDTWSTPHSYESLTFCVQVQGKSKREKKDR

VFTDKTSATVICRKNASISVRAQDRYYSSSWSEWASVPCS;
``` wherein the first and second polypeptide forms a heterodimeric complex.

In some embodiments, the IL-12(p35) polypeptide and the IL-12(p40) polypeptide is expressed at a ratio of 1:1, 1:2, 1:3, 1:4, 1:5, 1:6, 1:7, 1:8, 1:9, or 1:10. In some embodiments, the IL-12(p35) polypeptide and the IL-12(p40) polypeptide is expressed at a ratio of 1:1. In some embodiments, the IL-12(p35) polypeptide and the IL-12(p40) polypeptide is expressed at a ratio of 1:2. In some embodiments, the IL-12(p35) polypeptide and the IL-12(p40) polypeptide is expressed at a ratio of 1:3. In some embodiments, the IL-12(p35) polypeptide and the IL-12(p40) polypeptide is expressed at a ratio of 1:4. In some embodiments, the IL-12(p35) polypeptide and the IL-12(p40) polypeptide is expressed at a ratio of 1:5. In some embodiments, the IL-12(p35) polypeptide and the IL-12(p40) polypeptide is expressed at a ratio of 1:6. In some embodiments, the IL-12(p35) polypeptide and the IL-12(p40) polypeptide is expressed at a ratio of 1:7. In some embodiments, the IL-12(p35) polypeptide and the IL-12(p40) polypeptide is expressed at a ratio of 1:8. In some embodiments, the IL-12(p35) polypeptide and the IL-12(p40) polypeptide is expressed at a ratio of 1:9. In some embodiments, the IL-12(p35) polypeptide and the IL-12(p40) polypeptide is expressed at a ratio of 1:10. In some embodiments, the IL-12(p35) polypeptide and the IL-12(p40) polypeptide expressed at a ratio of 1:1, 1:2, 1:3, 1:4, 1:5, 1:6, 1:7, 1:8, 1:9, or 1:10, interact with each other to form a heterodimeric complex. In some embodiments, the IL-12(p35) polypeptide and the IL-12(p40) polypeptide, expressed at a ratio of 1:1, interact with each other to form a heterodimeric complex. In some embodiments, the IL-12(p35) polypeptide and the IL-12(p40) polypeptide, expressed at a ratio of 1:2, interact with each other to form a heterodimeric complex. In some embodiments, the IL-12(p35) polypeptide and the IL-12(p40) polypeptide, expressed at a ratio of 1:3, interact with each other to form a heterodimeric complex. In some embodiments, the IL-12(p35) polypeptide and the IL-12(p40) polypeptide, expressed at a ratio of 1:4, interact with each other to form a heterodimeric complex. In some embodiments, the IL-12(p35) polypeptide and the IL-12(p40) polypeptide, expressed at a ratio of 1:5, interact with each other to form a heterodimeric complex. In some embodiments, the IL-12(p35) polypeptide and the IL-12(p40) polypeptide, expressed at a ratio of 1:6, interact with each other to form a heterodimeric complex. In some embodiments, the IL-12(p35) polypeptide and the IL-12(p40) polypeptide, expressed at a ratio of 1:7, interact with each other to form a heterodimeric complex. In some embodiments, the IL-12(p35) polypeptide and the IL-12(p40) polypeptide, expressed at a ratio of 1:8, interact with each other to form a heterodimeric complex. In some embodiments, the IL-12(p35) polypeptide and the IL-12(p40) polypeptide, expressed at a ratio of 1:9, interact with each other to form a heterodimeric complex. In some embodiments, the IL-12(p35) polypeptide and the IL-12(p40) polypeptide, expressed at a ratio of 1:10, interact with each other to form a heterodimeric complex.

In some embodiments, the IL-12 is a IL-12 mutein, a recombinant IL-12, or a modified IL-12 molecule, fusion proteins or antibodies that act on the IL-12 pathway. In some embodiments, the IL-12(p35) is a IL-12(p35) mutein, a recombinant IL-12(p35), or a modified IL-12(p35) molecule, a fusion proteins or an antibody. In some embodiments, the IL-12(p40) is a IL-12(p40) mutein, a recombinant IL-12(p40), or a modified IL-12(p40) molecule, a fusion proteins or an antibody. In some embodiments, the IL-12 (p35) and the IL-12(p40) interact with one another to form a heterodimeric complex.

In some embodiments, an IL-12 mutein can be prepared by mutating one or more of the residues of IL-12. In some embodiments, the mutation is a deletion, a substitution, or an insertion. In some embodiments, the mutation is a substitution. In some embodiments, the substitution is a naturally occurring amino acid. In some embodiments, an IL-12(p35) mutein can be prepared by mutating one or more residues of IL-12(p35). In some embodiments, an IL-12(p40) mutein can be prepared by mutating one or more residues of IL-12(p40). In some embodiments, the IL-12 mutein molecule comprises a mutation in the polypeptide sequence at a position of amino acid 220. In some embodiments, the IL-12 mutein molecule comprises a mutation in the polypeptide sequence at a position of amino acid 222. In some embodiments, the IL-12 mutein molecule comprises a mutation in the polypeptide sequence at a position of amino acid 220 and/or 222. In some embodiments, the IL-12 comprises a N222L mutation. In some embodiments, the IL-12 comprises a N222L mutation in the IL-12(p40) amino acid sequence. In some embodiments, the IL-12 comprises a N222L mutation in the IL-12(p40) amino acid sequence as compared to SEQ ID NO: 4. In some embodiments, the IL-12(p40) mutein comprises a N222L mutation that corresponds to SEQ ID NO: 4. In some embodiments, the IL-12 comprises a N222Q mutation. In some embodiments, the IL-12 comprises a N222Q mutation in the IL-12(p40) amino acid sequence. In some embodiments, the IL-12 comprises a N222Q mutation in the IL-12(p40) amino acid sequence as compared to SEQ ID NO: 4. In some embodiments, the IL-12(p40) mutein comprises a N222Q mutation that corresponds to SEQ ID NO: 4. In some embodiments, the IL-12 comprises a N220L mutation. In some embodiments, the IL-12 comprises a N220L mutation in the IL-12(p40) amino acid sequence. In some embodiments, the IL-12 comprises a N220L mutation in the IL-12(p40) amino acid sequence as compared to SEQ ID NO: 5. In some embodiments, the IL-12(p40) mutein comprises a N220L mutation that corresponds to SEQ ID NO: 5. In some embodiments, an IL-12 (p40) mutein can be prepared by mutating one or more of the residues of IL-12(p40). In some embodiments, the IL-12 (p35) comprises a mutation at any position as compared to SEQ ID NO: 3. In some embodiments, the IL-12(p40) comprises a mutation at any position as compared to SEQ ID NO: 4. In some embodiments, the IL-12(p40) comprises a mutation at any position as compared to SEQ ID NO: 5. In some embodiments, the IL-12(p40) mutein comprises a mutation of asparagine at position 222 as compared to SEQ ID NO: 4. In some embodiments, the IL-12(p40) mutein comprises a substitution at position N222 as compared to SEQ ID NO: 4. In some embodiments, the IL-12(p40) mutein comprises a mutation of N222L as compared to SEQ ID NO: 4. In some embodiments, the IL-12(p40) mutein comprises a mutation of N222Q as compared to SEQ ID NO: 4. In some embodiments, the IL-12(p40) mutein comprises a mouse IL-12(p40) as set forth in SEQ ID NO: 5. In some embodiments, the mouse IL-12(p40) mutein comprises a mutation of N220L as compared to SEQ ID NO: 5.

(SEQ ID NO: 5)
MCPQKLTISWFAIVLLVSPLMAMWELEKDVYVVEVDWTPDAPGETVNL

TCDTPEEDDITWTSDQRHGVIGSGKTLTITVKEFLDAGQYTCHKGGET

-continued

LSHSHLLLHKKENGIWSTEILKNEKNKTFLKCEAPNYSGRFTCSWLVQ

RNMDLKFNIKSSSSSPDSRAVTCGMASLSAEKVTLDQRDYEKYSVSCQ

EDVTCPTAEETLPIELALEARQQNKYENYSTSFFIRDIIKPDPPKNLQ

MKPLKNSQVEVSWEYPDSWSTPHSYFSLKFFVRIQRKKEKMKETEEGC

NQKGAFLVEKTSTEVQCKGGNVCVQAQDRYYNSSCSKWACVPCRVRS mouse IL-12(p40).

In some embodiments, the IL-12 mutein, the IL-12(p35) mutein, and the IL-12(p40) mutein are as provided in PCT Publication Nos. WO2001068802, and WO2017201350, each of which is incorporated hereby by reference in its entirety.

The cell can also be modified to produce or secrete an additional protein or molecule in addition to native human IL-12. In some embodiments, the cell is modified to produce or secrete a native human IL-2.

In some embodiments, native human IL-2 refers to a protein encoded by a nucleic acid sequence comprising

```
                                        (SEQ ID NO: 6)
ATGTACAGGATGCAACTCCTGTCTTGCATTGCACTAAGTCTTGCACTT

GTCACAAACAGTGCACCTACTTCAAGTTCTACAAAGAAAACACAGCTA

CAACTGGAGCATTTACTGCTGGATTTACAGATGATTTTGAATGGAATT

AATAATTACAAGAATCCCAAACTCACCAGGATGCTCACATTTAAGTTT

TACATGCCCAAGAAGGCCACAGAACTGAAACATCTTCAGTGTCTAGAA

GAAGAACTCAAACCTCTGGAGGAAGTGCTAAATTTAGCTCAAAGCAAA

AACTTTCACTTAAGACCCAGGGACTTAATCAGCAATATCAACGTAATA

GTTCTGGAACTAAAGGGATCTGAAACAACATTCATGTGTGAATATGCT

GATGAGACAGCAACCATTGTAGAATTTCTGAACAGATGGATTACCTTT

TGTCAAAGCATCATCTCAACACTGACTTGA.
```

In some embodiments, the nucleic acid coding sequence encoding native human IL-2 is codon-optimized. In some embodiments, the nucleic acid coding sequence encoding native human IL-2 is codon-optimized for expression in a mammalian cell. The codon optimized sequence may be generated using a commercially available algorithm, e.g., GeneOptimizer (ThermoFisher Scientific), Optimum-Gene™ (GenScript, Piscataway, NJ USA), GeneGPS® (ATUM, Newark, CA USA), Java Codon Adaptation Tool (JCat, www.jcat.de, Grote, A. et al., Nucleic Acids Research, Vol 33, Issue suppl_2, pp. W526-W531 (2005), IDT Codon Optimization Tool (Integrated DNA Technologies), Vector-Builder Codon Optimization tool (VectorBuilder Inc.), Codon Optimization OnLine (COOL, bioinfo.bti.a-star.e-du.sg/COOL/; Chin J. X., et al., Bioinformatics, Vol 30, Issue 15, p.2210-2212 (2014)), or ExpOptimizer (NovoPro, Shanghai, China). Examples of codon-optimized nucleic acid coding sequences encoding native human IL-2 comprise, but are not limited to:

```
                                        (SEQ ID NO: 7)
ATGTACCGGATGCAGCTGCTGTCCTGCATCGCACTGTCCCTCGCCCTG

GTGACAAATTCTGCCCCCACCTCCTCCAGCACAAAAAAGACCCAGTTG

CAGCTGGAGCACCTGCTGCTGGATCTGCAGATGATCCTGAATGGCATC
```

-continued

```
AATAACTACAAAAACCCTAAACTGACCAGAATGCTGACCTTTAAATTT

TACATGCCTAAAAAGGCAACCGAGCTGAAGCACCTGCAGTGCCTGGAA

GAGGAACTGAAGCCCCTGGAGGAGGTGCTGAACCTGGCCCAGAGCAAG

AACTTTCACCTGCGGCCCCGCGACCTGATCAGCAACATCAACGTGATC

GTGCTGGAGCTGAAGGGCAGTGAAACCACATTCATGTGCGAGTACGCC

GACGAGACCGCCACAATCGTGGAGTTCCTGAACAGATGGATCACATTC

TGTCAGTCCATCATTAGCACACTGACCTAA;
```

```
                                        (SEQ ID NO: 8)
ATGTACCGCATGCAGCTGCTGAGCTGCATCGCCCTGAGCCTGGCCCTG

GTGACCAACAGCGCCCCCACCAGCAGCAGCACCAAGAAGACCCAGCTG

CAGCTGGAGCACCTGCTGCTGGACCTGCAGATGATCCTGAACGGCATC

AACAACTACAAGAACCCCAAGCTGACCCGCATGCTGACCTTCAAGTTC

TACATGCCCAAGAAGGCCACCGAGCTGAAGCACCTGCAGTGCCTGGAG

GAGGAGCTGAAGCCCCTGGAGGAGGTGCTGAACCTGGCCCAGAGCAAG

AACTTCCACCTGCGCCCCCGCGACCTGATCAGCAACATCAACGTGATC

GTGCTGGAGCTGAAGGGCAGCGAGACCACCTTCATGTGCGAGTACGCC

GACGAGACCGCCACCATCGTGGAGTTCCTGAACCGCTGGATCACCTTC

TGCCAGAGCATCATCAGCACCCTGACCTAA;
```

```
                                        (SEQ ID NO: 9)
ATGTATAGGATGCAGCTGCTCTCTTGTATCGCGTTGTCTCTGGCTTTG

GTGACTAACTCAGCTCCCACGTCCAGCAGTACCAAAAAGACCCAGCTG

CAGCTGGAACATCTTCTGTTGGATCTGCAAATGATACTGAATGGGATC

AACAACTATAAAAACCCAAAACTGACTAGAATGCTGACTTTCAAGTTC

TACATGCCTAAAAAGGCAACAGAATTGAAGCACCTTCAGTGCCTGGAG

GAGGAGCTTAAGCCCCTGGAGGAGGTGCTGAATCTGGCCCAAAGTAAG

AATTTTCATCTGCGACCCAGGGATCTGATCAGTAATATCAATGTGATC

GTCCTGGAGCTGAAGGGCAGTGAGACCACGTTTATGTGTGAATACGCA

GACGAAACCGCCACTATCGTTGAATTCTTGAACAGGTGGATCACCTTT

TGTCAGAGTATCATCAGCACCCTCACT;
or
```

```
                                        (SEQ ID NO: 10)
ATGTACAGAATGCAGCTGCTGAGCTGCATCGCCCTGAGCCTGGCCCTG

GTGACCAACAGCGCCCCCACAAGCAGCAGCACCAAGAAGACACAGCTG

CAGCTGGAGCACCTGCTGCTGGACCTGCAGATGATCCTGAACGGCATC

AACAACTACAAGAACCCCAAGCTGACAAGAATGCTGACCTTCAAGTTC

TACATGCCCAAGAAGGCCACCGAGCTGAAGCACCTGCAGTGCCTGGAG

GAGGAGCTGAAGCCCCTGGAAGAGGTGCTGAACCTGGCTCAGAGCAAG

AACTTCCACCTGAGACCTAGAGACCTGATCAGCAACATCAACGTGATC

GTGCTGGAGCTGAAGGGCAGCGAGACCACCTTCATGTGCGAGTACGCC

GACGAGACCGCCACCATCGTGGAGTTCCTGAACAGATGGATCACCTTC

TGTCAGAGCATCATCAGCACCCTGACCTGA.
```

In some embodiments, the codon-optimized nucleic acid coding sequence encoding native human IL-2 comprise the nucleic acid sequence as set forth in SEQ ID NO: 7-10. In some embodiments, the codon-optimized nucleic acid coding sequence encoding native human IL-2 comprise the nucleic acid sequence as set forth in SEQ ID NO: 7. In some embodiments, the codon-optimized nucleic acid coding sequence encoding native human IL-2 comprise the nucleic acid sequence having at least 90%, 92%, 93%, 94%, 95%, 96%, 97%, 98%, 99%, or 100% identity to the sequence of SEQ ID NO: 7-10. In some embodiments, the codon-optimized nucleic acid coding sequence encoding native human IL-2 comprise the nucleic acid sequence having at least 90%, 92%, 93%, 94%, 95%, 96%, 97%, 98%, 99%, or 100% identity to the sequence of SEQ ID NO: 7.

In some embodiments, the native human protein produced by the cell is formed from the formed from an amino acid sequence of:

(SEQ ID NO: 11)
MYRMQLLSCIALSLALVINSAPTSSSTKKTQLQLEHLLLDLQMILNGI

NNYKNPKLTRMLTFKFYMPKKATELKHLQCLEEELKPLEEVLNLAQSK

NFHLRPRDLISNINVIVLELKGSETTFMCEYADETATIVEFLNRWITF

CQSIISTLT.

In some embodiments, the additional protein or molecule is a native human IL-2. In some embodiments, the additional protein or molecule is a IL-2 mutein or a modified IL-2 molecule, fusion proteins or antibodies that act on the IL-2 pathway. In some embodiments, the IL-2 is a pegylated IL-2 molecule. In some embodiments, the pegylated IL-2 molecule has a wild-type sequence. In some embodiments, the pegylated IL-2 has a mutant IL-2 sequence. In some embodiments, the additional protein or molecule is selected from NKTR-214, THOR-707, ALKS 4230, Nemvaleukin Alfa, TransCon IL-2 β/γ, BNT151, BNT153, CLN-617, CUE-101, CUE-102, CUE-103, Anktiva® (N-803), KY1043, MDNA11, NL-201, SO-C101, R06874281, Simlukafusp Alfa, RG7461, WTX-124, WTX-330, XTX202, or XTX401, or any combination thereof. The additional protein may be of any size, e.g., greater than about 100 Da, 200 Da, 250 Da, 500 Da, 750 Da, 1 KDa, 1.5 kDa, 2 kDa, 2.5 kDa, 3 kDa, 4 kDa, 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, kDa, 75 kDa, 80 kDa, 85 kDa, 90 kDa, 95 kDa, 100 kDa, 125 kDa, 150 kDa, 200 kDa, 200 kDa, 250 kDa, 300 kDa, 400 kDa, 500 kDa, 600 kDa, 700 kDa, 800 Da, 900 kDa, or more. In some embodiments, the protein is composed of a single subunit or multiple subunits (e.g., a dimer, trimer, tetramer, etc.). A protein produced or secreted by a cell may be modified, for example, by glycosylation, methylation, or other known natural or synthetic protein modification. A protein may be produced or secreted as a pre-protein or in an inactive form and may require further modification to convert it into an active form.

Proteins produced or secreted by a cell may be include antibodies or antibody fragments, for example, an Fc region or variable region of an antibody. Exemplary antibodies include anti-PD-1, anti-PD-L1, anti-CTLA4, anti-TNFα, and anti-VEGF antibodies. An antibody may be monoclonal or polyclonal. Other exemplary proteins include a lipoprotein, an adhesion protein, hemoglobin, enzymes, proenkephalin, a growth factor (e.g., EGF, IGF-1, VEGF alpha, HGF, TGF beta, bFGF), or a cytokine.

A protein produced or secreted by a cell may also include a hormone. Exemplary hormones include growth hormone, growth hormone releasing hormone, prolactin, lutenizing hormone (LH), anti-diuretic hormone (ADH), oxytocin, thyroid stimulating hormone (TSH), thyrotropin-release hormone (TRH), adrenocorticotropic hormone (ACTH), follicle-stimulating hormone (FSH), thyroxine, calcitonin, parathyroid hormone, aldosterone, cortisol, epinephrine, glucagon, insulin, estrogen, progesterone, and testosterone.

A protein produced or secreted by a cell may include other cytokines. A cytokine may be a pro-inflammatory cytokine or an anti-inflammatory cytokine. Example of cytokines include IL-I, IL-1α, IL-1β, IL-1RA, IL-4, IL-5, IL-6, IL-7, IL-8, IL-9, IL-10, IL-11, IL-12, IL-12a, IL-12b, IL-13, IL-14, IL-15, IL-16, IL-17, G-CSF, GM-CSF, IL-20, IL-23, IFN-α, IFN-β, IFN-γ, CD154, LT-f3, CD70, CD153, CD178, TRAIL, TNF-α, TNF-β, SCF, M-CSF, MSP, 4-1BBL, LIF, OSM, and others. For example, a cytokine may include any cytokine described in M. J. Cameron and D. J. Kelvin, *Cytokines, Chemokines, and Their Receptors* (2013), Landes Biosciences, which is incorporated herein by reference in its entirety.

An provided for herein implantable construct may comprise a cell expressing a single type of therapeutic agent, e.g., a single protein or nucleic acid, or may express more than one type of therapeutic agent, e.g., a plurality of proteins or nucleic acids. In some embodiments, an implantable construct comprises a cell expressing two types of therapeutic agents (e.g., two types of proteins or nucleic acids). In some embodiments, an implantable construct comprises a cell expressing three types of therapeutic agents (e.g., three types of proteins or nucleic acids). In some embodiments, an implantable construct comprises a cell expressing four types of therapeutic agents (e.g., four types of proteins or nucleic acids).

In some embodiments, an implantable construct comprises a cell expressing a single type of nucleic acid (e.g., DNA or RNA) or may express more than one type of nucleic acid, e.g., a plurality of nucleic acid (e.g., DNA or RNA). In some embodiments, an implantable construct comprises a cell expressing two types of nucleic acids (e.g., DNA or RNA). In some embodiments, an implantable construct comprises a cell expressing three types of nucleic acids (e.g., DNA or RNA). In some embodiments, an implantable construct comprises a cell expressing four types of nucleic acids (e.g., DNA or RNA).

In some embodiments, an implantable construct comprises a cell expressing a single type of protein, or may express more than one type of protein, e.g., a plurality of proteins. In some embodiments, an implantable construct comprises a cell expressing two types of proteins. In some embodiments, an implantable construct comprises a cell expressing three types of proteins. In some embodiments, an implantable construct comprises a cell expressing four types of proteins.

In some embodiments, an implantable construct comprises a cell expressing a single type of enzyme, or may express more than one type of enzyme, e.g., a plurality of enzymes. In some embodiments, an implantable construct comprises a cell expressing two types of enzymes. In some embodiments, an implantable construct comprises a cell expressing three types of enzymes. In some embodiments, an implantable construct comprises a cell expressing four types of enzymes.

In some embodiments, an implantable construct comprises a cell expressing a single type of antibody or antibody fragment or may express more than one type of antibody or antibody fragment, e.g., a plurality of antibodies or antibody fragments. In some embodiments, an implantable construct comprises a cell expressing two types of antibodies or antibody fragments.

In some embodiments, an implantable construct comprises a cell expressing three types of antibodies or antibody fragments. In some embodiments, an implantable construct comprises a cell expressing four types of antibodies or antibody fragments.

In some embodiments, an implantable construct comprises a cell expressing a single type of hormone, or may express more than one type of hormone, e.g., a plurality of hormones. In some embodiments, an implantable construct comprises a cell expressing two types of hormones. In some embodiments, an implantable construct comprises a cell expressing three types of hormones. In some embodiments, an implantable construct comprises a cell expressing four types of hormones.

In some embodiments, an implantable construct comprises a cell expressing a single type of enzyme, or may express more than one type of enzyme, e.g., a plurality of enzymes. In some embodiments, an implantable construct comprises a cell expressing two types of enzymes. In some embodiments, an implantable construct comprises a cell expressing three types of enzymes. In some embodiments, an implantable construct comprises a cell expressing four types of enzymes.

In some embodiments, an implantable construct comprises a cell expressing a single type of cytokine or may express more than one type of cytokine, e.g., a plurality of cytokines. In some embodiments, an implantable construct comprises a cell expressing two types of cytokines. In some embodiments, an implantable construct comprises a cell expressing three types of cytokines. In some embodiments, an implantable construct comprises a cell expressing four types of cytokines.

D. FEATURES OF IMPLANTABLE CONSTRUCTS

The implantable construct described herein may take any suitable shape or morphology. For example, an implantable construct may be a sphere, spheroid, tube, cord, string, ellipsoid, disk, cylinder, sheet, torus, cube, stadiumoid, cone, pyramid, triangle, rectangle, square, or rod. An implantable construct may comprise a curved or flat section. In some embodiments, an implantable construct may be prepared through the use of a mold, resulting in a custom shape.

The implantable construct may vary in size, depending, for example, on the use or site of implantation. For example, an implantable construct may have a mean diameter or size greater than 0.1 mm, e.g., greater than 0.25 mm, 0.5 mm, 0.75, 1 mm, 1.5 mm, 2 mm, 3 mm, 4 mm, 5 mm, 6 mm, 7 mm, 8 mm, 9 mm, 10 mm, 20 mm, 30 mm, 40 mm, 50 mm, or more. In some embodiments, an implantable construct may have a section or region with a mean diameter or size greater than 0.1 mm, e.g., greater than 0.25 mm, 0.5 mm, 0.75, 1 mm, 1.5 mm, 2 mm, 3 mm, 4 mm, 5 mm, 6 mm, 7 mm, 8 mm, 9 mm, 10 mm, 20 mm, 30 mm, 40 mm, 50 mm, or more. In some embodiments, an implantable construct may have a mean diameter or size less than 1 cm, e.g., less 50 mm, 40 mm, 30 mm, 20 mm, 10 mm, 7.5 mm, 5 mm, 2.5 mm, 1 mm, 0.5 mm, or smaller. In some embodiments, an implantable construct may have a section or region with a mean diameter or size less than 1 cm, e.g., less 50 mm, 40 mm, 30 mm, 20 mm, 10 mm, 7.5 mm, 5 mm, 2.5 mm, 1 mm, 0.5 mm, or smaller.

In some embodiments, an implantable construct comprises at least one zone capable of preventing exposure of an enclosed antigenic or therapeutic agent from the outside milieu, e.g., a host effector cell or tissue. In some embodiments, the implantable construct comprises an inner zone (IZ). In some embodiments, the implantable construct comprises an outer zone (OZ). In some embodiments, either the inner zone (IZ) or outer zone (OZ) may be erodible or degradable. In some embodiments, the inner zone (IZ) is erodible or degradable. In some embodiments, the outer zone (OZ) is erodible or degradable. In some embodiments, the implantable construct comprises both an inner zone (IZ) and an outer zone (OZ), either of which may be erodible or degradable. In some embodiments, the implantable construct comprises both an inner zone (IZ) and an outer zone (OZ), wherein the outer zone is erodible or degradable. In some embodiments, the implantable construct comprises both an inner zone (IZ) and an outer zone (OZ), wherein the inner zone is erodible or degradable. The thickness of either of the zone, e.g., either the inner zone or outer zone, may be correlated with the length or duration of a "shielded" phase, in which the encapsulated antigenic or therapeutic agent is protected or shielded from the outside milieu, e.g., a host effector cell or tissue.

In some embodiments, the implantable construct can be a matrix of a polymer admixed with cells expressing a molecule of interest. For example, the implantable construct can be prepared according to methods provided for herein or known to one of skill in the art to create an implantable construct that comprises a layer of a hydrogel (e.g., alginate) that surrounds a population of cells expressing a molecule of interest, such as IL-12 or as otherwise provided for herein. In some embodiments, the layer is an acellular layer. In some embodiments, what would be considered the outer layer comprises cells distributed in the outer area of the implantable construct.

Thus, the implantable construct can comprise a zone that comprises a majority of the cells, but they can also be distributed throughout the construct.

As used herein, the term "encapsulated" as it is used in reference to the implantable construct refers to a cells that are surrounded by a matrix or hydrogel polymer, such as alginate. The term "encapsulated" can refer to a construct that has an acellular layer as the outer layer or an outer layer that has cells distributed in it. Encapsulated is a general term and is meant to include cells being admixed with the polymer in general, not that there are no cells at or near the surface of the construct. As provided for herein, this can also be referred to as a capsule that encapsulates a population of cells. The phrase "a population of encapsulated cells" should be understood to refer to one or more capsules encapsulating a population of cells. A composition, such as a pharmaceutical composition, can comprise a plurality of capsules. The composition can also comprise different capsules, in that it comprises a capsule that encapsulates cells heterologously expressing one first of interest and a second capsule that encapsulates cells heterologously expressing a second protein of interest. In some embodiments, the first protein of interest is IL-2 and the second protein of interest is IL-12. In some embodiments, the a capsule comprises a population of cells that expresses IL-2 and IL-12 from either the same cell or different cells encapsulated in the same capsule.

In some embodiments, a zone (e.g., the inner zone or outer zone) or layer of the implantable construct may comprise a degradable entity, e.g., an entity capable of degradation. A degradable entity may comprise an enzyme cleavage site, a photolabile site, a pH-sensitive site, or other labile region that can be eroded or comprised over time. In some embodiments, the degradable entity is preferentially degraded upon exposure to a first condition (e.g., exposure to a first milieu, e.g., a first pH or first enzyme) relative to a second condition (e.g., exposure to a second milieu, e.g., a second pH or second enzyme). In one embodiment, the degradable entity is degraded at least 2, 5, 10, 20, 30, 40, 50, 60, 70, 80, or 100 times faster upon exposure to a first condition relative to a second condition. In some embodiments, the degradable entity is an enzyme cleavage site, e.g., a proteolytic site. In some embodiments, the degradable entity is a polymer (e.g., a synthetic polymer or a naturally occurring polymer, e.g., a peptide or polysaccharide). In some embodiments, the degradable entity is a substrate for an endogenous host component, e.g., a degradative enzyme, e.g., a remodeling enzyme, e.g., a collagenase or metalloprotease. In some embodiments, the degradable entity comprises a cleavable linker or cleavable segment embedded in a polymer.

In some embodiments, an implantable construct comprises a pore or opening to permit passage of an object, such as a small molecule (e.g., nutrients or waste), a protein, or a nucleic acid. For example, a pore in or on an implantable construct may be greater than 0.1 nm and less than 10 µm. In some embodiments, the implantable construct comprises a pore or opening with a size range of 0.1 µm to 10 µm, 0.1 µm to 9 µm, 0.1 µm to 8 µm, 0.1 µm to 7 µm, 0.1 µm to 6 µm, µm to 5 µm, 0.1 µm to 4 µm, 0.1 µm to 3 µm, 0.1 µm to 2 µm.

An implantable construct described herein may comprise a chemical modification in or on any enclosed material. Exemplary chemical modifications include small molecules, peptides, proteins, nucleic acids, lipids, or oligosaccharides. The implantable construct may comprise at least 0.5%, 1%, 2%, 3%, 4%, 5%, 7.5%, 10%, 15%, 20%, 30%, 40%, 50%, 60%, 70%, 80% or more of a material that is chemically modified, e.g., with a chemical modification described herein. An implantable construct may be partially coated with a chemical modification, e.g., at least about 5%, 10%, 15%, 20%, 25%, 30%, 35%, 40%, 45%, 50%, 55%, 60%, 65%, 70%, 75%, 80%, 85%, 90%, 95%, 99%, or 99.9% coated with a chemical modification.

In some embodiments, the implantable construct is formulated such that the duration of release of the antigenic and/or therapeutic agent is tunable. For example, an implantable construct may be configured in a certain manner to release a specific amount of an antigenic or therapeutic agent over time, e.g., in a sustained or controlled manner. In some embodiments, the implantable construct comprises a zone (e.g., an inner zone or an outer zone) that is degradable, and this controls the duration of therapeutic release from the construct by gradually ceasing immunoprotection of encapsulated cells or causing gradual release of the antigenic agent. In some embodiments, the implantable construct is configured such that the level of release of an antigenic or therapeutic agent is sufficient to modulate the ratio of a host effector cell, e.g., a host T cell. In some embodiments, the implantable construct is configured such that the level of release of an antigenic or therapeutic agent is sufficient to activate a host cell (e.g., a host T effector cell or a host NK cell) or increase the level of certain host cells (e.g., host T effector cells or host NK cells). In some embodiments, the implantable construct is configured such that the level of release of an antigenic or therapeutic agent is not sufficient to activate a host regulator cell (e.g., a host T regulator cell) or increase the level of host regulator cells (e.g., host T regulator cells).

In some embodiments, the implantable construct comprises a zone that is targeted by the natural foreign body response (FBR) of a host or subject, e.g., over a period of time. In some embodiments, the implantable construct is coated with fibrotic overgrowth upon administration to a subject, e.g., over a period of time. Fibrotic overgrowth on the surface of the implantable construct may lead to a decrease in function of the implantable construct. For example, a decrease in function may comprise a reduction in the release of an antigenic or therapeutic agent over time, a decrease in pore size, or a decrease in the diffusion rate of oxygen and other key nutrients to the encapsulated cells, leading to cell death. In some embodiments, the rate of fibrotic overgrowth may be tuned to design a dosing regimen. For example, the fibrotic overgrowth on the surface of an implantable construct may result in a decrease in function of the implantable construct about 6 hours, 12 hours, 18 hours, 1 day, 2 days, 3 days, 4 days, 5 days, 6 days, 7 days, 8 days, 9 days, 10 days, 11 days, 12 days, 13 days, 2 weeks, 2.5 weeks, 3 weeks, 4 weeks, or 6 weeks after administration (e.g., injection or implantation) to a subject.

In some embodiments, the implantable construct is chemically modified with a specific density of modifications. The specific density of chemical modifications may be described as the average number of attached chemical modifications per given area. For example, the density of a chemical modification on or in an implantable construct may be 0.01, 0.1, 0.5, 1, 5, 10, 15, 20, 50, 100, 200, 400, 500, 750, 1,000, 2,500, or 5,000 chemical modifications per square µm or square mm.

An implantable construct may be formulated or configured for implantation in any organ, tissue, cell, or part of a subject. For example, the implantable construct may be implanted or disposed into the intraperitoneal space of a subject. In some embodiments, the implantable construct may be implanted or disposed into the subcutaneous space of a subject. An implantable construct may be implanted in or disposed on a tumor or other growth in a subject, or be implanted in or disposed about 0.1 mm, 0.5 mm, 1 mm, 0.25 mm, 0.5 mm, 0.75, 1 mm, 1.5 mm, 2 mm, 3 mm, 4 mm, 5 mm, 6 mm, 7 mm, 8 mm, 9 mm, 10 mm, 20 mm, 30 mm, 40 mm, 50 mm, 1 cm, 5, cm, 10 cm, or further from a tumor or other growth in a subject. An implantable construct may be configured for implantation, or implanted, or disposed on or in the skin, under the skin, a mucosal surface, a body cavity, the central nervous system (e.g., the brain or spinal cord), an organ (e.g., the heart, eye, liver, kidney, spleen, lung, ovary, breast, uterus), the lymphatic system, vasculature, oral cavity, nasal cavity, gastrointestinal tract, bone, muscle, adipose tissue, or other area.

An implantable construct may be formulated for use for any period of time. For example, an implantable construct may be used for 1 hour, 2 hours, 4 hours, 6 hours, 12 hours, 1 day, 36 hours, 2 days, 3 days, 4 days, 5 days, 6 days, 1 week, 2 weeks, 3 weeks, 4 weeks, 5 weeks, 6 weeks, 2 months, 3 months, 4 months, 5 months, 6 months, 1 year, or longer. An implantable construct can be configured for limited exposure (e.g., less than 2 days, e.g., less than 2 days, 1 day, 24 hours, 20 hours, 16 hours, 12 hours, 10 hours, 8 hours, 6 hours, 5 hours, 4 hours, 3 hours, 2 hours, 1 hour or less). A implantable construct can be configured for prolonged exposure (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more). An implantable construct can be configured for permanent exposure (e.g., at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more).

In some embodiments, the degradable zone comprises a polymeric hydrogel, such as but not limited to chitosan, cellulose, hyaluronic acid, or alginate. In some embodiments, the alginate is SLG20. In some embodiments, the alginate is not modified. In some embodiments, the alginate is not modified with an anti-fibrotic molecule. For clarity, a cell expressing a molecule that may have an anti-fibrotic effect is not a modification of the alginate or hydrogel that would be considered anti-fibrotic.

Accordingly, in some embodiments, a population of encapsulated cells comprising an oligonucleotide molecule encoding a native human IL-12 polypeptide is provided. In some embodiments, a population of encapsulated cells comprising an oligonucleotide molecule encoding a recombinant IL-12 polypeptide is provided. In some embodiments, a population of encapsulated cells comprising an oligonucleotide molecule encoding an IL-12 mutein polypeptide is provided. In some embodiments, a population of encapsulated cells comprising an oligonucleotide molecule encoding a native human IL-12(p35) polypeptide is provided. In some embodiments, a population of encapsulated cells comprising an oligonucleotide molecule encoding a native human IL-12(p40) polypeptide is provided. In some embodiments, a population of encapsulated cells comprising an oligonucleotide molecule encoding a recombinant IL-12(p35) polypeptide is provided. In some embodiments, a population of encapsulated cells comprising an oligonucleotide molecule encoding a recombinant IL-12(p40) polypeptide is provided. In some embodiments, a population of encapsulated cells comprising an oligonucleotide molecule encoding an IL-12(p35) mutein polypeptide is provided. In some embodiments, a population of encapsulated cells comprising an oligonucleotide molecule encoding an IL-12(p40) mutein polypeptide is provided.

In some embodiments, a population of encapsulated cells comprising a plurality of oligonucleotide molecules encoding a native human IL-12 polypeptide is provided. In some embodiments, a population of encapsulated cells comprising a plurality of oligonucleotide molecules encoding a recombinant IL-12 polypeptide is provided. In some embodiments, a population of encapsulated cells comprising a plurality of oligonucleotide molecules encoding an IL-12 mutein polypeptide is provided. In some embodiments, a population of encapsulated cells comprising a plurality of oligonucleotide molecules encoding a native human IL-12(p35) polypeptide is provided. In some embodiments, a population of encapsulated cells comprising a plurality of oligonucleotide molecules encoding a native human IL-12(p40) polypeptide is provided. In some embodiments, a population of encapsulated cells comprising a plurality of oligonucleotide molecules encoding a recombinant IL-12(p35) polypeptide is provided. In some embodiments, a population of encapsulated cells comprising a plurality of oligonucleotide molecules encoding a recombinant IL-12(p40) polypeptide is provided. In some embodiments, a population of encapsulated cells comprising a plurality of oligonucleotide molecules encoding an IL-12(p35) mutein polypeptide is provided. In some embodiments, a population of encapsulated cells comprising a plurality of oligonucleotide molecules encoding an IL-12(p40) mutein polypeptide is provided. In some embodiments, a population of encapsulated cells comprising a plurality of oligonucleotide molecules encoding a native human IL-12(p35) polypeptide and a native human IL-12(p40) polypeptide is provided. In some embodiments, a population of encapsulated cells comprising a plurality of oligonucleotide molecules encoding a recombinant IL-12 (p35) polypeptide and a recombinant IL-12(p40) polypeptide is provided. In some embodiments, a population of encapsulated cells comprising a plurality of oligonucleotide molecules encoding an IL-12(p35) mutein polypeptide and an IL-12(p40) mutein polypeptide is provided. In some embodiments, a population of encapsulated cells comprising a plurality of oligonucleotide molecules encoding a native human IL-12(p35) polypeptide and a recombinant IL-12 (p40) polypeptide is provided. In some embodiments, a population of encapsulated cells comprising a plurality of oligonucleotide molecules encoding a recombinant IL-12 (p35) polypeptide and a native human IL-12(p40) polypeptide is provided. In some embodiments, a population of encapsulated cells comprising a plurality of oligonucleotide molecules encoding a native human IL-12(p35) polypeptide and an IL-12(p40) mutein polypeptide is provided. In some embodiments, a population of encapsulated cells comprising a plurality of oligonucleotide molecules encoding an IL-12 (p35) mutein polypeptide and a native human IL-12(p40) polypeptide is provided. In some embodiments, a population of encapsulated cells comprising a plurality of oligonucleotide molecules encoding a recombinant IL-12(p35) polypeptide and an IL-12(p40) mutein polypeptide is provided. In some embodiments, a population of encapsulated cells comprising a plurality of oligonucleotide molecules encoding an IL-12(p35) mutein polypeptide and a recombinant IL-12(p40) polypeptide is provided.

In some embodiments, the oligonucleotide encoding native human IL-12 polypeptide comprises a sequence of SEQ ID NO: 1 and SEQ ID NO: 2. In some embodiments, the oligonucleotide encoding native human IL-12(p35) polypeptide comprises a sequence of SEQ ID NO: 1. In some embodiments, the oligonucleotide encoding native human IL-12(p40) polypeptide comprises a sequence of SEQ ID NO: 2. In some embodiments, the cell produces a recombinant IL-12 protein. In some embodiments, the cell produces a recombinant IL-12(p35) protein. In some embodiments, the cell produces a recombinant IL-12(p40) protein. In some embodiments, the cell produces an IL-12 mutein protein. In some embodiments, the cell produces an IL-12(p35) mutein protein. In some embodiments, the cell produces an IL-12(p40) mutein protein. In some embodiments, the IL-12(p35) mutein is as provided herein. In some embodiments, the IL-12(p40) mutein is as provided herein.

In some embodiments, the population of encapsulated cells remains viable for at least 1-180 days. In some embodiments, the population of encapsulated cells remains viable for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 55, at least 60, at least at least 70, at least 75, at least 80, at least 85, at least 90, at least 95, at least 100, at least 110, at least 120, at least 130, at least 140, at least 150, at least 160, at least 170, or at least 180 days. In some embodiments, the population of encapsulated cells remains viable for at least 6 days. In some embodiments, the population of encapsulated cells remains viable for at least 14 days. In some embodiments, the population of encapsulated cells remains viable for at least 21 days. In some embodiments, the population of encapsulated cells remains viable for at least 40 days. In some embodiments, the population of encapsulated cells remains viable for at least 120 days.

Also provided for herein are pharmaceutical compositions comprising the encapsulated cells.

E. METHODS OF TREATMENT

Described herein are methods of treatment or uses of encapsulated cells for the preparation of a pharmaceutical composition (or medicament) for the treatment of tumors or a disease.

In some embodiments, the disease is a proliferative disease. In some embodiments, the proliferative disease is cancer. A cancer may be an epithelial, mesenchymal, or hematological malignancy. A cancer includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). In some embodiments, the cancer is a solid tumor (e.g., carcinoid, carcinoma or sarcoma), a soft tissue tumor (e.g., a heme malignancy), or a metastatic lesion, e.g., a metastatic lesion of any of the cancers disclosed herein. In some embodiments, the cancer is a fibrotic or desmoplastic solid tumor. In some embodiments, the tumor is a pancreatic tumor.

Accordingly, in some embodiments, methods of treating a tumor, such as a pancreatic tumor, in a subject, are provided. In some embodiments, the methods comprise implanting in the intraperitoneal space of the subject a pharmaceutical composition comprising a plurality of a population of encapsulated cells (e.g., a capsule) as provided for herein to treat the cancer.

In some embodiments, the pharmaceutical composition comprises a plurality of populations of encapsulated cells that express IL-12, as provided herein. In some embodiments, the pharmaceutical composition comprises a plurality of populations of encapsulated cells that express IL-12 and IL-2 as provided herein.

A method of providing systemic treatment to a subject with cancer, the method comprising implanting in the intraperitoneal space of the subject a pharmaceutical composition comprising a plurality of a the population of encapsulated cells (e.g., a capsule) as provided for herein, whereby the pharmaceutical composition stimulates the activation of immune cells in the intraperitoneal space and the activated immune cells migrate to a region of the subject that is distal to the intraperitoneal space to treat the cancer systemically in the subject.

In some embodiments, methods of providing systemic treatment to a subject with cancer are provided. In some embodiments, the methods comprise implanting in the intraperitoneal space of the subject a pharmaceutical composition comprising a plurality of a the population of encapsulated cells (e.g., a capsules) as provided herein. In some embodiments, the pharmaceutical composition activates immune cells in the IP space. In some embodiments, the activated immune cells migrate out of (away from) the intraperitoneal space to treat the cancer in the subject at a site that is not in the IP space. In some embodiments, the activated immune cells migrate out of (away from) the intraperitoneal space to treat the cancer in the subject at a site that is distal from the IP space. In some embodiments, the site is another organ or tissue, such as pancreas, breast, brain, lungs, bone, or as otherwise provided for herein.

In some embodiments, the subject is administered (e.g., implanted) about 0.01 μg/kg/day to about 20 μg/kg/day, about 0.1 μg/kg/day to about 20 μg/kg/day, about 1 μg/kg/day to about μg/kg/day, about 2 μg/kg/day to about 20 μg/kg/day, about 5 μg/kg/day to about 20 μg/kg/day, about 7.5 to about 20 μg/kg/day, about 9 μg/kg/day to about 20 μg/kg/day, about 10 μg/kg/day to about 20 μg/kg/day, about 11 μg/kg/day to about 20 μg/kg/day, about 12 μg/kg/day to about 20 μg/kg/day, about 13 μg/kg/day to about 20 μg/kg/day, about 14 μg/kg/day to about 15 μg/kg/day, about 15 μg/kg/day to about 20 μg/kg/day, about 10 μg/kg/day to about 15 μg/kg/day, about 11 μg/kg/day to about 15 μg/kg/day, about 12 μg/kg/day to about 15 μg/kg/day, about 13 μg/kg/day to about 15 μg/kg/day, about 14 μg/kg/day to about 15 μg/kg/day, about 16 μg/kg/day to about 20 μg/kg/day, about 17 μg/kg/day to about 20 μg/kg/day, about 18 μg/kg/day to about 20 μg/kg/day, about 0.01 μg/kg/day, about 0.05 μg/kg/day, about 0.1 μg/kg/day, about 0.5 μg/kg/day, about 1 μg/kg/day, about 2 μg/kg/day, about 3 μg/kg/day, about 4 μg/kg/day, about 5 μg/kg/day, about 6 μg/kg/day, about 7 μg/kg/day, about 8 μg/kg/day, about 9 μg/kg/day, about 10 μg/kg/day, about 11 μg/kg/day, about 12 μg/kg/day, about 13 μg/kg/day, about 14 μg/kg/day, about 15 μg/kg/day, about 16 μg/kg/day, about 17 μg/kg/day, about 18 μg/kg/day, about 19 μg/kg/day, or about 20 μg/kg/day, of the encapsulated cells as provided herein.

As described herein, the encapsulated cells producing the recombinant native human IL-12 can be used to create memory immunity against a tumor. Thus, in some embodiments, the methods provided herein can be used to prevent or reduce the probability of a tumor recurring either at the initial site of the tumor or a site that is distal to the origin of the tumor. In some embodiments, the tumor is a pancreatic tumor. In some embodiments, the methods of treating a tumor by generating (inducing) memory immunity comprise implanting a pharmaceutical composition comprising a population of encapsulated cells as provided for herein.

In some embodiments, methods of selectively activating CD8 and/or CD4 positive effector T cells are provided. Without being bound by any particular theory, the CD8 positive and/or CD4 positive effector cells are activated and trigger an immune response against the tumor. This can be initiated or enhanced by the secretion of native human IL-12 in the IP space from the encapsulated cells that are provided for herein. In some embodiments, the methods comprise implanting a pharmaceutical composition comprising a population of encapsulated cells as provided for herein.

In some embodiments, the effector T cells are selectively activated and expanded as compared to Tregs (CD4+CD25+ FOXp3+). In some embodiment, the selectively activated T cell secrete IFN-γ.

In some embodiments, encapsulated cells implanted or administered to the subject do not become significantly fibrosed in the subject. In some embodiments, the encapsulated cells expressing IL-12 implanted or administered to the subject do not become significantly fibrosed in the subject. In some embodiments, the encapsulated cells expressing IL-12 implanted or administered to the subject do not become significantly fibrosed in the subject over time.

Exemplary cancers that can be treated by the methods provided for herein include, but are not limited to, carcinoma, lymphoma, blastoma, sarcoma, and leukemia or lymphoid malignancies. In some embodiments, the cancer affects a system of the body, e.g., the nervous system (e.g., peripheral nervous system (PNS) or central nervous system (CNS)), vascular system, skeletal system, respiratory system, endocrine system, lymph system, reproductive system, or gastrointestinal tract. In some embodiments, cancer affects a part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Other examples of cancers include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In some embodiments, the implantable construct (encapsulated cells) described herein may be used in a method to modulate (e.g., upregulate) the immune response in a subject. For example, upon administration to a subject, the implantable construct (or an antigenic and/or therapeutic agent disposed within) may modulate (e.g., upregulate) the level of a component of the immune system in a subject (e.g., increasing the level or decreasing the level of an immune system component). Exemplary immune system components that may be modulated by an implantable construct or related method described herein include stem cells (hematopoietic stem cells), NK cells, T cells (e.g., an adaptive T cell (e.g., a helper T cell, a cytotoxic T cell, memory T cell, or regulatory T cell) or an innate-like T cell (e.g., natural killer T cell, mucosal-associated invariant T cell, or gamma delta T cell), B cells, an antibody or fragment thereof, or other another component. In some embodiments, the modulation comprises increasing or decreasing the activation of a T cell or other immune system component (e.g., by about 5%, 10%, 15%, 20%, 25%, 30%, 35%, 40%, 45%, 50%, 55%, 60%, 65%. 70%, 75%, 80%, 85%, 90%, 95%, 99%, or more compared with a control). In some embodiments, the encapsulated cells (implantable construct) can be used to activate CD4 positive and/or CD8 positive immune cells.

The implantable construct described herein may be used to modulate the immune response in a subject for a specific period of time. For example, administration of the implantable construct (or an antigenic and/or therapeutic agent disposed within) may activate the immune response (e.g., by increase in the level of an immune system component) in a subject for at least 1 hour, 2 hours, 3 hours, 4 hours, 6 hours, 8 hours, 10 hours, 12 hours, 16 hours, 20 hours, 1 day, 1.5 days, 2 days, 3 days, 4 days, 5 days, 6 days, 1 week, 1.5 weeks, 2 weeks, 3 weeks, 4 weeks, 5 weeks, 6 weeks, 2 months, 2.5 months, 3 months, 4 months, 5 months, 6 months, or longer. In some embodiments, administration of the implantable construct activates the immune response (e.g., by increase in the level of an immune system component) in a subject between 1 hour and 1 month, 1 hour and 3 weeks, 1 hour and 2 weeks, 1 hour and 1 week, 6 hours and 1 week, or 6 hours and 3 days. In some embodiments, implantation of the implantable construct (e.g., an implantable construct described herein) results in upregulation of T cells in a subject, e.g., as measured by a blood test, for at least 1 day.

The implantable constructs described herein may further comprise an additional pharmaceutical agent, such as an anti-proliferative agent, anti-cancer agent, anti-inflammatory agent, an immunomodulatory agent, or a pain-relieving agent, e.g., for use in combination therapy. The additional pharmaceutical agent may be disposed in or on the implantable construct or may be produced by a cell disposed in or on the implantable construct. In some embodiments, the additional pharmaceutical agent is small molecule, a protein, a peptide, a nucleic acid, an oligosaccharide, or other agent.

In some embodiments, the additional pharmaceutical agent is an anti-cancer agent. In some embodiments, the anti-cancer agent is a small molecule, a kinase inhibitor, an alkylating agent, a vascular disrupting agent, a microtubule targeting agent, a mitotic inhibitor, a topoisomerase inhibitor, an anti-angiogenic agent, or an anti-metabolite. In some embodiments, the anti-cancer agent is a taxane (e.g., paclitaxel, docetaxel, larotaxel or cabazitaxel). In some embodiments, the anti-cancer agent is an anthracycline (e.g., doxorubicin). In some embodiments, the anti-cancer agent is a platinum-based agent (e.g., cisplatin or oxaliplatin). In some embodiments, the anti-cancer agent is a pyrimidine analog (e.g., gemcitabine). In some embodiments, the anti-cancer agent is chosen from camptothecin, irinotecan, rapamycin, FK506, 5-FU, leucovorin, or a combination thereof. In other embodiments, the anti-cancer agent is a protein biologic (e.g., an antibody molecule), or a nucleic acid therapy (e.g., an antisense or inhibitory double stranded RNA molecule).

In some embodiments, the additional pharmaceutical agent is an immunomodulatory agent, e.g., one or more of an activator of a costimulatory molecule, an inhibitor of an immune checkpoint molecule, or an anti-inflammatory agent. In some embodiments, the immunomodulatory agent is an inhibitor of an immune checkpoint molecule (e.g., an inhibitor of PD-1, PD-L1, LAG-3, TIM-3 or CTLA4, or any combination thereof). In some embodiments, the immunomodulatory agent is a cancer vaccine.

In some embodiments, the immunomodulatory agent is an inhibitor of PD-1, PD-L1, PD-L2, CTLA4, TIM3, LAGS, VISTA, BTLA, TIGIT, LAIR1, CD73, CD160, 2B4 and/or TGFR beta. In one embodiment, the inhibitor of an immune checkpoint molecule inhibits PD-1, PD-L1, LAG-3, TIM-3 or CTLA4, or any combination thereof. Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof that binds to PD-1, PD-L1, PD-L2, CTLA4, TIM3, LAGS, VISTA, BTLA, TIGIT, LAIR1, CD73, CD160, 2B4 and/or TGFR beta, or a combination thereof. In some embodiments, the immunomodulatory agent is an anti-inflammatory agent, e.g., an anti-inflammatory agent as described herein. In some embodiments, the anti-inflammatory agent is an agent that blocks, inhibits, or reduces inflammation or signaling from an inflammatory signaling pathway. In some embodiments, the anti-inflammatory agent inhibits or reduces the activity of one or more of any of the following an immune component of the subject. In some embodiments, the anti-inflammatory agent is an IL-1 or IL-1 receptor antagonist, such as anakinra, rilonacept, or canakinumab. In some embodiments, the anti-inflammatory agent is an IL-6 or IL-6 receptor antagonist, e.g., an anti-IL-6 antibody or an anti-IL-6 receptor antibody, such as tocilizumab (ACTEMRA®), olokizumab, clazakizumab, sarilumab, sirukumab, siltuximab, or ALX-0061. In some embodiments, the anti-inflammatory agent is a TNF-α antagonist, e.g., an anti-TNF-α antibody, such as infliximab (REMICADE®), golimumab (SIMPONI®), adalimumab (HUMIRA®), certolizumab pegol (CIMZIA®) or etanercept. In one embodiment, the anti-inflammatory agent is a corticosteroid, e.g., as described herein.

F. COMPOSITIONS AND ADMINISTRATIONS OF IMPLANTABLE CONSTRUCTS

The present disclosure also provides pharmaceutical compositions comprising an implantable construct as provided for herein and optionally a pharmaceutically acceptable excipient. In some embodiments, the implantable construct is provided in an effective amount in the pharmaceutical composition. In some embodiments, the effective amount is a therapeutically effective amount. In some embodiments, the effective amount is a prophylactically effective amount.

In some embodiments, the effective amount is an amount that produces an effective amount of a native human IL-12. In some embodiments, the effective amount is an amount that produces an effective amount of a recombinant IL-12. In some embodiments, the effective amount is an amount that produces an effective amount of an IL-12 mutein. In some embodiments, the effective amount is an amount that produces an effective amount of native human IL-12(p35). In some embodiments, the effective amount is an amount that produces an effective amount of native human IL-12(p40). In some embodiments, the effective amount is an amount that produces an effective amount of recombinant IL-12 (p35). In some embodiments, the effective amount is an amount that produces an effective amount of recombinant IL-12(p40). In some embodiments, the effective amount is an amount that produces an effective amount of IL-12(p35) mutein. In some embodiments, the effective amount is an amount that produces an effective amount of IL-12(p40) mutein. In some embodiments, the effective amount is an amount that produces an effective amount of IL-2.

Pharmaceutical compositions described herein can be prepared by any method known in the art of pharmacology. In general, such preparatory methods include the steps of bringing the implantable construct into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the implantable construct may be generally equal to the dosage of the antigenic and/or therapeutic agent which would be administered to a subject and/or a convenient fraction of such a dosage such as, for example, one-half or one-third of such a dosage.

In some embodiments, the pharmaceutical compositions are frozen or cryopreserved. In some embodiments, the pharmaceutical compositions are not frozen or not cryopreserved.

Relative amounts of the implantable construct, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) of any component.

The implantable construct and a pharmaceutical composition thereof may be administered or implanted orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally. In some embodiments, the implantable construct is injected subcutaneously. In some embodiments, the implantable construct is injected into the intraperitoneal space. In some embodiments, the implantable construct is injected into the intraperitoneal space. In some embodiments, the implantable constructed is delivered to the subject using a device, e.g., a cannula or catheter.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For ophthalmic use, provided compounds, compositions, and devices may be formulated as micronized suspensions or in an ointment such as petrolatum.

In some embodiments, the release of an antigenic, therapeutic, or additional pharmaceutical agent is released in a sustained fashion. In order to prolong the effect of a particular agent, it is often desirable to slow the absorption of the agent from injection. This can be accomplished by the use of a liquid suspension of crystalline or amorphous material with poor water solubility. The rate of absorption of the agent then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The implantable constructs provided herein are typically formulated in dosage unit form, e.g., single unit dosage form, for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific therapeutic agent employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

The therapeutic agent administered may be at dosage levels sufficient to deliver from about mg/kg to about 100 mg/kg, from about 0.0001 mg/kg to about 100 mg/kg, from about 0.001 mg/kg to about 100 mg/kg, from about 0.01 mg/kg to about 50 mg/kg, preferably from about mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 0.001 mg/kg to about 1 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The constructs (e.g., encapsulated cells) can be prepared according to any known method. For example, in some embodiments, methods of preparing encapsulated cells producing a recombinant protein are provided. In some embodiments, the methods comprise feeding through a coaxial needle a first composition comprising a polymeric hydrogel and a second composition comprising cells to be encapsulated suspended in a polymeric hydrogel to drop into a crosslinking solution to form the encapsulated cells, wherein the crosslinking solution comprises a sugar alcohol, a buffer, a metal salt, and a surfactant.

In some embodiments, the cells to be encapsulated comprise an oligonucleotide molecule encoding a native human IL-12. In some embodiments, the cells to be encapsulated comprise an oligonucleotide molecule encoding a recombinant IL-12. In some embodiments, the cells to be encapsulated comprise an oligonucleotide molecule encoding an IL-12 mutein. In some embodiments, the cells to be encapsulated comprise an oligonucleotide molecule encoding a native human IL-12(p35). In some embodiments, the cells to be encapsulated comprise an oligonucleotide molecule encoding a native human IL-12(p40). In some embodiments, the cells to be encapsulated comprise an oligonucleotide molecule encoding a recombinant IL-12(p35). In some embodiments, the cells to be encapsulated comprise an oligonucleotide molecule encoding a recombinant IL-12 (p40). In some embodiments, the cells to be encapsulated comprise an oligonucleotide molecule encoding an IL-12 (p35) mutein. In some embodiments, the cells to be encapsulated comprise an oligonucleotide molecule encoding an IL-12(p40) mutein. In some embodiments, the cells to be encapsulated comprise a plurality of oligonucleotide molecules encoding a native human IL-12(p35) and a native human IL-12(p40). In some embodiments, the cells to be encapsulated comprise a plurality of oligonucleotide molecules encoding a recombinant IL-12(p35) and a recombinant IL-12(p40). In some embodiments, the cells to be encapsulated comprise a plurality of oligonucleotide molecules encoding an IL-12(p35) mutein and an IL-12(p40) mutein. In some embodiments, the cells to be encapsulated comprise an oligonucleotide molecule encoding a native human IL-2.

In some embodiments, the oligonucleotide encoding a native human IL-12(p35) comprises a sequence of SEQ ID NO: 1. In some embodiments, the oligonucleotide encoding a native human IL-12(p40) comprises a sequence of SEQ ID NO: 2. In some embodiments, the native human IL-12(p35) and the native human IL-12(p40) interact with each other to form a heterodimeric complex. In some embodiments, the heterodimeric complex is the native human IL-12. In some embodiments, the cell produces a native human IL-12 protein. In some embodiments, the native human IL-12 protein is formed from an amino acid sequence of SEQ ID NO: 3 and SEQ ID NO: 4. In some embodiments, the cell produces a recombinant IL-12 protein. In some embodiments, the recombinant IL-12 protein comprises a recombinant IL-12 (p35) protein and a recombinant IL-12(p40) protein. In some embodiments, the cell produces an IL-12 mutein protein. In some embodiments, the IL-12 mutein protein comprises an IL-12(p35) mutein protein and an IL-12(p40) mutein protein. In some embodiments, the oligonucleotide encoding native human IL-2 comprises a sequence of SEQ ID NO: 6.

The cells can be any type of cell. In some embodiments, the cell is a mammalian cell. In some embodiments, the cell is an epithelial cell. In some embodiments, the cell is a RPE cell. In some embodiments, the cell is a ARPE-19 cell, ARPE-19-SEAP-2-neo cell, RPE-J cell, and hTERT RPE-1 cell. In some embodiments, the cell is an engineered RPE cell. In some embodiments, the engineered cell is derived from the ARPE-19 cell line. In some embodiments, the cell is as provided herein. In some embodiments, the surfactant is TWEEN 20 (polysorbate 20). In some embodiments, the buffer is HEPES buffer. In some embodiments, the sugar alcohol is mannitol. In some embodiments, the metal salt is barium chloride.

In some embodiments, the method comprises washing the encapsulated cells produced according to the methods provided for herein in a buffer solution produced. In some embodiments, the washing step removes substantially all or all of the free barium or barium chloride.

In some embodiments, the encapsulated cells prepared according to the methods provided herein are stored in a storage buffer, such as DMEM/F12 cell culture media. In some embodiments, the stored cells retain viability for at least 10, 20, or 30 days. In some embodiments, the storage buffer is substantially free of plasmalyte buffer.

Also provided for herein, are a population of encapsulated cells prepared according to a method as provided for herein.

In some embodiments, a suspension of encapsulated cells is provided. In some embodiments, the suspension comprises a population of encapsulated cells as provided for herein. In some embodiments, the encapsulated cells are encapsulated by a polymeric hydrogel, and the suspension comprises a crosslinking solution that comprises a sugar alcohol, a buffer, a metal salt, and a surfactant. In some embodiments, the cells are ARPE-19 cells. In some embodiments, the surfactant is TWEEN 20 (polysorbate 20). In some embodiments, the buffer is HEPES buffer. In some embodiments, the sugar alcohol is mannitol. In some embodiments, the metal salt is barium chloride.

In some embodiments, suspensions of encapsulated cells are provided, wherein the suspension comprises a population of encapsulated cells as provided for herein, wherein the encapsulated cells are encapsulated by a polymeric hydrogel, and a storage buffer, such as DMEM/F12 cell culture media.

In some embodiments, the suspension provided for herein are substantially free of plasmalyte buffer.

G. ENUMERATED EMBODIMENTS

1. A population of encapsulated cells comprising a plurality of oligonucleotide molecules encoding a IL-12 polypeptide.

2. The population of encapsulated cells of embodiment 1, wherein the IL-12 polypeptide is a native human IL-12 polypeptide, a recombinant IL-12 polypeptide, or an IL-12 mutein polypeptide.

3. The population of encapsulated cells of embodiment 2, wherein the native human IL-12 polypeptide is a heterodimeric complex comprising a native human IL-12(p35) polypeptide and a native human IL-12(p40) polypeptide.

4. The population of encapsulated cells of any one of embodiments 1-3, wherein the plurality of oligonucleotide molecules encodes the native human IL-12(p35) polypeptide and the native human IL-12(p40) polypeptide.

5. The population of encapsulated cells of any one of embodiments 1-4, wherein the oligonucleotide encoding the native human IL-12(p35) polypeptide comprises a sequence of:

```
                                    (SEQ ID NO: 1)
ATTTCGCTTTCATTTTGGGCCGAGCTGGAGGCGGCGGGGCCGTCCCGGA

ACGGCTGCGGCCGGGCACCCCGGGAGTTAATCCGAAAGCGCCGCAAGCC

CCGCGGGCCGGCCGCACCGCACGTGTCACCGAGAAGCTGATGTAGAGAG

AGACACAGAAGGAGACAGAAAGCAAGAGACCAGAGTCCCGGGAAAGTCC

TGCCGCGCCTCGGGACAATTATAAAAATGTGGCCCCCTGGGTCAGCCTC
```

-continued

CCAGCCACCGCCCTCACCTGCCGCGGCCACAGGTCTGCATCCAGCGGCT

CGCCCTGTGTCCCTGCAGTGCCGGCTCAGCATGTGTCCAGCGCGCAGCC

TCCTCCTTGTGGCTACCCTGGTCCTCCTGGACCACCTCAGTTTGGCCAG

AAACCTCCCCGTGGCCACTCCAGACCCAGGAATGTTCCCATGCCTTCAC

CACTCCCAAAACCTGCTGAGGGCCGTCAGCAACATGCTCCAGAAGGCCA

GACAAACTCTAGAATTTTACCCTTGCACTTCTGAAGAGATTGATCATGA

AGATATCACAAAAGATAAAACCAGCACAGTGGAGGCCTGTTTACCATTG

GAATTAACCAAGAATGAGAGTTGCCTAAATTCCAGAGAGACCTCTTTCA

TAACTAATGGGAGTTGCCTGGCCTCCAGAAAGACCTCTTTTATGATGGC

CCTGTGCCTTAGTAGTATTTATGAAGACTTGAAGATGTACCAGGTGGAG

TTCAAGACCATGAATGCAAAGCTTCTGATGGATCCTAAGAGGCAGATCT

TTCTAGATCAAACATGCTGGCAGTTATTGATGAGCTGATGCAGGCCCT

GAATTTCAACAGTGAGACTGTGCCACAAAAATCCTCCCTTGAAGAACCG

GATTTTTATAAAACTAAAATCAAGCTCTGCATACTTCTTCATGCTTTCA

GAATTCGGGCAGTGACTATTGATAGAGTGATGAGCTATCTGAATGCTTC

CTAAAAAGCGAGGTCCCTCCAAACCGTTGTCATTTTTATAAAACTTTGA

AATGAGGAAACTTTGATAGGATGTGGATTAAGAACTAGGGAGGGGGAAA

GAAGGATGGGACTATTACATCCACATGATACCTCTGATCAAGTATTTTT

GACATTTACTGTGGATAAATTGTTTTTAAGTTTTCATGAATGAATTGCT

AAGAAGGGAAAATATCCATCCTGAAGGTGTTTTTCATTCACTTTAATAG

AAGGGCAAATATTTATAAGCTATTTCTGTACCAAAGTGTTTGTGGAAAC

AAACATGTAAGCATAACTTATTTTAAAATATTTATTTATATAACTTGGT

AATCATGAAAGCATCTGAGCTAACTTATATTTATTTATGTTATATTTAT

TAAATTATTTATCAAGTGTATTTGAAAAATATTTTTAAGTGTTCTAAAA

ATAAAAGTATTGAATTAAAGTGA.

6. The population of encapsulated cells of any one of embodiments 1-5, wherein the oligonucleotide encoding the native human IL-12(p40) polypeptide comprises a sequence of:

(SEQ ID NO: 2)
AGAAGAAACAACATCTGTTTCAGGGCCATTGGACTCTCCGTCCTGCCCA

GAGCAAGATGTGTCACCAGCAGTTGGTCATCTCTTGGTTTTCCCTGGTT

TTTCTGGCATCTCCCCTCGTGGCCATATGGGAACTGAAGAAAGATGTTT

ATGTCGTAGAATTGGATTGGTATCCGGATGCCCCTGGAGAAATGGTGGT

CCTCACCTGTGACACCCCTGAAGAAGATGGTATCACCTGGACCTTGGAC

CAGAGCAGTGAGGTCTTAGGCTCTGGCAAAACCCTGACCATCCAAGTCA

AAGAGTTTGGAGATGCTGGCCAGTACACCTGTCACAAAGGAGGCGAGGT

TCTAAGCCATTCGCTCCTGCTGCTTCACAAAAAGGAAGATGGAATTTGG

TCCACTGATATTTTAAAGGACCAGAAAGAACCCAAAAATAAGACCTTTC

TAAGATGCGAGGCCAAGAATTATTCTGGACGTTTCACCTGCTGGTGGCT

GACGACAATCAGTACTGATTTGACATTCAGTGTCAAAAGCAGCAGAGGC

TCTTCTGACCCCCAAGGGGTGACGTGCGGAGCTGCTACACTCTCTGCAG

-continued

AGAGAGTCAGAGGGGACAACAAGGAGTATGAGTACTCAGTGGAGTGCCA

GGAGGACAGTGCCTGCCCAGCTGCTGAGGAGAGTCTGCCCATTGAGGTC

ATGGTGGATGCCGTTCACAAGCTCAAGTATGAAAACTACACCAGCAGCT

TCTTCATCAGGGACATCATCAAACCTGACCCACCCAAGAACTTGCAGCT

GAAGCCATTAAAGAATTCTCGGCAGGTGGAGGTCAGCTGGGAGTACCCT

GACACCTGGAGTACTCCACATTCCTACTTCTCCCTGACATTCTGCGTTC

AGGTCCAGGGCAAGAGCAAGAGAGAAAAGAAAGATAGAGTCTTCACGGA

CAAGACCTCAGCCACGGTCATCTGCCGCAAAAATGCCAGCATTAGCGTG

CGGGCCCAGGACCGCTACTATAGCTCATCTTGGAGCGAATGGGCATCTG

TGCCCTGCAGTTAGGTTCTGATCCAGGATGAAAATTTGGAGGAAAAGTG

GAAGATATTAAGCAAAATGTTTAAAGACACAACGGAATAGACCCAAAAA

GATAATTTCTATCTGATTTGCTTTAAAACGTTTTTTTAGGATCACAATG

ATATCTTTGCTGTATTTGTATAGTTAGATGCTAAATGCTCATTGAAACA

ATCAGCTAATTTATGTATAGATTTTCCAGCTCTCAAGTTGCCATGGGCC

TTCATGCTATTTAAATATTTAAGTAATTTATGTATTTATTAGTATATTA

CTGTTATTTAACGTTTGTCTGCCAGGATGTATGGAATGTTTCATACTCT

TATGACCTGATCCATCAGGATCAGTCCCTATTATGCAAAATGTGAATTT

AATTTTATTTGTACTGACAACTTTTCAAGCAAGGCTGCAAGTACATCAG

TTTTATGACAATCAGGAAGAATGCAGTGTTCTGATACCAGTGCCATCAT

ACACTTGTGATGGATGGGAACGCAAGAGATACTTACATGGAAACCTGAC

AATGCAAACCTGTTGAGAAGATCCAGGAGAACAAGATGCTAGTTCCCAT

GTCTGTGAAGACTTCCTGGAGATGGTGTTGATAAAGCAATTTAGGGCCA

CTTACACTTCTAAGCAAGTTTAATCTTTGGATGCCTGAATTTTAAAAGG

GCTAGAAAAAATGATTGACCAGCCTGGGAAACATAACAAGACCCCGTC

TCTACAAAAAAATTTAAAATTAGCCAGGCGTGGTGGCTCATGCTTGTG

GTCCCAGCTGTTCAGGAGGATGAGGCAGGAGGATCTCTTGAGCCCAGGA

GGTCAAGGCTATGGTGAGCCGTGATTGTGCCACTGCATACCAGCCTAGG

TGACAGAATGAGACCCTGTCTCAAAAAAAAAAATGATTGAAATTAAAAT

TCAGCTTTAGCTTCCATGGCAGTCCTCACCCCCACCTCTCTAAAAGACA

CAGGAGGATGACACAGAAACACCGTAAGTGTCTGGAAGGCAAAAAGATC

TTAAGATTCAAGAGAGAGGACAAGTAGTTATGGCTAAGGACATGAAATT

GTCAGAATGGCAGGTGGCTTCTTAACAGCCCTGTGAGAAGCAGACAGAT

GCAAAGAAAATCTGGAATCCCTTTCTCATTAGCATGAATGAACCTGATA

CACAATTATGACCAGAAAATATGGCTCCATGAAGGTGCTACTTTTAAGT

AATGTATGTGCGCTCTGTAAAGTGATTACATTTGTTTCCTGTTTGTTTA

TTTATTTATTTATTTTTGCATTCTGAGGCTGAACTAATAAAAACTCTTC

TTTGTAATCATA.

7. The population of encapsulated cells of any one of embodiments 1-6, wherein the expressed IL-12(p35) polypeptide and the expressed IL-12(p40) polypeptide form a heterodimeric complex.

8. The population of encapsulated cells of embodiment 2, wherein the recombinant IL-12 is a heterodimeric complex comprising a recombinant IL-12(p35) polypeptide and a recombinant IL-12(p40) polypeptide.

9. The population of encapsulated cells of embodiment 2, wherein the IL-12 mutein is a heterodimeric complex comprising an IL-12(p35) mutein polypeptide and an IL-12(p40) mutein polypeptide.

10. The population of encapsulated cells of embodiment 9, wherein the plurality of oligonucleotide molecules encodes the IL-12(p35) mutein polypeptide and the IL-12(p40) mutein polypeptide.

11. The population of encapsulated cells of any one of embodiments 9 or 10, wherein the IL-12(p40) mutein polypeptide comprises a mutation selected from N220L, N222L or N222Q as compared to SEQ ID NO: 4.

12. The population of encapsulated cells of any one of embodiments 9 or 10, wherein the IL-12(p40) mutein polypeptide comprises a mutation of N222L as compared to SEQ ID NO: 4.

13. The population of encapsulated cells of any one of embodiments 9 or 10, wherein the IL-12(p40) mutein polypeptide comprises a mutation of N222Q as compared to SEQ ID NO: 4.

14. The population of encapsulated cells of any one of embodiments 9 or 10, wherein the IL-12(p40) mutein polypeptide comprises a mutation of N220L as compared to SEQ ID NO: 5.

15. The population of encapsulated cells of any one of embodiments 1-14, wherein the IL-12(p35) polypeptide and the IL-12(p40) polypeptide is expressed at a ratio of 1:1, 1:2, 1:3, 1:4, 1:5, 1:6, 1:7, 1:8, 1:9, or 1:10.

16. The population of encapsulated cells of any one of embodiments 1-15, wherein the cell produces a native human IL-12 heterodimeric protein, a recombinant IL-12 heterodimeric protein, or an IL-12 mutein heterodimeric protein.

17. The population of encapsulated cells of embodiment 16, wherein the native human IL-12 protein expressed by the cells comprises a polypeptide comprising a first polypeptide comprising the sequence of:

```
                              (SEQ ID NO: 3)
MCPARSLLLVATLVLLDHLSLARNLPVATPDPGMFPCLHHSQNLLRAVS

NMLQKARQTLEFYPCTSEEIDHEDITKDYTSTVEACLPLELTKNESCLN

SRETSFITNGSCLASRKTSFMMALCLSSIYEDLKMYQVEFKTMNAKLLM

DPKRQIFLIQNMLAVIDELMQALNENSETVPQKSSLEEPDFYKTKIKLC

ILLHAFRIRAVTIDRVMSYLNAS;
``` and
a second polypeptide comprising the sequence of:

```
                              (SEQ ID NO: 4)
MCHQQLVISWFSLVFLASPLVAIWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTESVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCS;
``` wherein the first and second polypeptide forms a heterodimeric complex.

18. The population of encapsulated cells of any one of embodiments 1-17, wherein the population of cell produces about 10 to about 50, about 10 to about 30, about 10 to about 20, or about 20 nanograms/cell/day of native human IL-12.

19. The population of encapsulated cells of any one of embodiments 1-18, wherein the cells are as provided herein.

20. The population of encapsulated cells of any one of embodiments 1-19, wherein the cells are ARPE-19 cells, ARPE-19-SEAP-2-neo cells, RPE-J cells, hTERT RPE-1 cells, or any combination thereof.

21. The population of encapsulated cells of any one of embodiments 1-20, wherein the cells are encapsulated with a polymeric hydrogel.

22. The population of encapsulated cells of any one of embodiments 1-21, wherein the polymeric hydrogel comprises chitosan, cellulose, hyaluronic acid, or alginate.

23. The population of encapsulated cells of any one of embodiments 1-22, wherein the polymeric hydrogel comprises alginate.

24. The population of encapsulated cells of any one of embodiments 1-23, wherein the alginate comprises SLG20.

25. The population of encapsulated cells of any one of embodiments 1-24, wherein the cells remain viable for at least 5, 10, 15, 20, 40, 120, or 180 days.

26. The population of encapsulated cells of any one of embodiments 1-25, wherein the encapsulated cells do not proliferate.

27. The population of encapsulated cells of any one of embodiments 1-26, wherein the encapsulated cells show no fibrotic overgrowth over time after implantation in a subject.

28. The population of encapsulated cells of any one of embodiments 1-27, wherein the encapsulated cells show small fibrotic overgrowth over time after implantation in a subject.

29. A pharmaceutical composition comprising the population of encapsulated cells of any one of embodiments 1-28.

30. The pharmaceutical composition of embodiment 29, further comprising a population of encapsulated cells comprising an oligonucleotide molecule encoding native human IL-2.

31. The pharmaceutical composition of embodiment 30, wherein the oligonucleotide encoding native human IL-2 comprises a sequence of:

```
                              (SEQ ID NO: 6)
ATGTACAGGATGCAACTCCTGTCTTGCATTGCACTAAGTCTTGCACTTG

TCACAAACAGTGCACCTACTTCAAGTTCTACAAAGAAAACACAGCTACA

ACTGGAGCATTTACTGCTGGATTTACAGATGATTTTGAATGGAATTAAT

AATTACAAGAATCCCAAACTCACCAGGATGCTCACATTTAAGTTTTACA

TGCCCAAGAAGGCCACAGAACTGAAACATCTTCAGTGTCTAGAAGAAGA

ACTCAAACCTCTGGAGGAAGTGCTAAATTTAGCTCAAAGCAAAAACTTT

CACTTAAGACCCAGGGACTTAATCAGCAATATCAACGTAATAGTTCTGG

AACTAAAGGGATCTGAAACAACATTCATGTGTGAATATGCTGATGAGAC

AGCAACCATTGTAGAATTTCTGAACAGATGGATTACCTTTTGTCAAAGC

ATCATCTCAACACTGACTTGA.
```

32. The pharmaceutical composition of embodiment 31, wherein the oligonucleotide encoding native human IL-2 comprises a sequence that is codon-optimized.

33. The pharmaceutical composition of embodiment 32, wherein the codon-optimized oligonucleotide encoding native human IL-2 comprises a sequence having at least 90%, 91%, 92%, 93%, 94%, 95%, 96%, 97%, 98%, 99%, or 100% sequence identity to SEQ ID NO: 7.

34. The pharmaceutical composition of any one of embodiments 30-33, wherein the cell produces recombinant native human IL-2 protein.

35. The pharmaceutical composition of any one of embodiments 30-34, wherein the recombinant native human IL-2 protein expressed by the cells comprises the amino acid sequence of:

```
                                      (SEQ ID NO: 11)
MYRMQLLSCIALSLALVTNSAPTSSSTKKTQLQLEHLLLDLQMILNGIN

NYKNPKLTRMLTFKFYMPKKATELKHLQCLEEELKPLEEVLNLAQSKNF

HLRPRDLISNINVIVLELKGSETTFMCEYADETATIVEFLNRWITFCQS

IISTLT.
```

36. The pharmaceutical composition of any one of embodiments 30-35, wherein the population of cell produces about 1 to about 10, about 1 to about 5, or about 2 to about 4 PCD (picograms/cell/day) of native human IL-2.

37. A method of treating a tumor, such as a pancreatic tumor, in a subject, the method comprising implanting in the intraperitoneal space of the subject a pharmaceutical composition comprising a plurality of encapsulated cells (e.g., a capsule) of any one of embodiments 1-28 to the subject to treat the cancer.

38. A method of reducing tumor burden, such as a pancreatic tumor, in a subject, the method comprising implanting in the intraperitoneal space of the subject a pharmaceutical composition comprising a plurality of encapsulated cells (e.g., a capsule) of any one of embodiments 1-28 to the subject to treat the cancer.

39. The method of embodiments 37 or 38, wherein the subject is administered about 0.01 µg/kg/day to about 20 µg/kg/day, about 0.1 µg/kg/day to about 20 µg/kg/day, about 1 µg/kg/day to about 20 µg/kg/day, about 2 µg/kg/day to about 20 µg/kg/day, about 5 µg/kg/day to about 20 µg/kg/day, about 7.5 to about 20 µg/kg/day, about 9 µg/kg/day to about 20 µg/kg/day, about 10 µg/kg/day to about 20 µg/kg/day, about 11 µg/kg/day to about 20 µg/kg/day, about 12 µg/kg/day to about 20 µg/kg/day, about 13 µg/kg/day to about 20 µg/kg/day, about 14 µg/kg/day to about 15 µg/kg/day, about 15 µg/kg/day to about 20 µg/kg/day, about 10 µg/kg/day to about 15 µg/kg/day, about 11 µg/kg/day to about 15 µg/kg/day, about 12 µg/kg/day to about 15 µg/kg/day, about 13 µg/kg/day to about 15 µg/kg/day, about 14 µg/kg/day to about 15 µg/kg/day, about 16 µg/kg/day to about 20 µg/kg/day, about 17 µg/kg/day to about 20 µg/kg/day, about 18 µg/kg/day to about 20 µg/kg/day, about 0.01 µg/kg/day, about 0.1 µg/kg/day, about 1 µg/kg/day, about 2 µg/kg/day, about 3 µg/kg/day, about 4 µg/kg/day, about 5 µg/kg/day, about 6 µg/kg/day, about 7 µg/kg/day, about 8 µg/kg/day, about 9 µg/kg/day, about 10 µg/kg/day, about 11 µg/kg/day, about 12 µg/kg/day, about 13 µg/kg/day, about 14 µg/kg/day, about 15 µg/kg/day, about 6 µg/kg/day, about 17 µg/kg/day, about 18 µg/kg/day, about 19 µg/kg/day, or about 20 µg/kg/day, of the encapsulated cells of any one of embodiments 1-28.

40. A method of treating a tumor, such as a melanoma tumor, in a subject, the method comprising implanting in the subcutaneous space of the subject a pharmaceutical composition comprising a plurality of encapsulated cells (e.g., a capsule) of any one of embodiments 1-28 to the subject to treat the cancer.

41. A method of reducing tumor burden, such as a melanoma tumor, in a subject, the method comprising implanting in the subcutaneous space of the subject a pharmaceutical composition comprising a plurality of encapsulated cells (e.g., a capsule) of any one of embodiments 1-28 to the subject to treat the cancer.

42. The method of embodiments 40 or 41, wherein the subject is administered about 0.01 µg/kg/day to about 20 µg/kg/day, about 0.1 µg/kg/day to about 20 µg/kg/day, about 1 µg/kg/day to about 20 µg/kg/day, about 2 µg/kg/day to about 20 µg/kg/day, about 5 µg/kg/day to about 20 µg/kg/day, about 7.5 to about 20 µg/kg/day, about 9 µg/kg/day to about 20 µg/kg/day, about 10 µg/kg/day to about 20 µg/kg/day, about 11 µg/kg/day to about 20 µg/kg/day, about 12 µg/kg/day to about 20 µg/kg/day, about 13 µg/kg/day to about 20 µg/kg/day, about 14 µg/kg/day to about 15 µg/kg/day, about 15 µg/kg/day to about 20 µg/kg/day, about 10 µg/kg/day to about 15 µg/kg/day, about 11 µg/kg/day to about 15 µg/kg/day, about 12 µg/kg/day to about 15 µg/kg/day, about 13 µg/kg/day to about 15 µg/kg/day, about 14 µg/kg/day to about 15 µg/kg/day, about 16 µg/kg/day to about 20 µg/kg/day, about 17 µg/kg/day to about 20 µg/kg/day, about 18 µg/kg/day to about 20 µg/kg/day, about 0.01 µg/kg/day, about 0.1 µg/kg/day, about 1 µg/kg/day, about 2 µg/kg/day, about 3 µg/kg/day, about 4 µg/kg/day, about 5 µg/kg/day, about 6 µg/kg/day, about 7 µg/kg/day, about 8 µg/kg/day, about 9 µg/kg/day, about 10 µg/kg/day, about 11 µg/kg/day, about 12 µg/kg/day, about 13 µg/kg/day, about 14 µg/kg/day, about 15 µg/kg/day, about 6 µg/kg/day, about 17 µg/kg/day, about 18 µg/kg/day, about 19 µg/kg/day, or about 20 µg/kg/day, of the encapsulated cells of any one of embodiments 1-28.

43. A method of treating a tumor in a subject by generating memory immunity, the method comprising implanting a pharmaceutical composition comprising the population of encapsulated cells of any one of embodiments 1-28.

44. A method of reducing tumor burden in a subject by generating memory immunity, the method comprising implanting a pharmaceutical composition comprising the population of encapsulated cells of any one of embodiments 1-28.

45. The method of embodiments 43 or 44, wherein the tumor is a pancreatic tumor, or a melanoma tumor.

46. A method of selectively activating CD8 positive effector T cells, the method comprising implanting a pharmaceutical composition comprising a population of encapsulated cells of any one of embodiments 1-28.

47. The method of embodiment 46, wherein the effector T cells are selectively activated and expanded as compared to Tregs (CD4+CD25+FoxP3+).

48. The method of embodiment 47, wherein the selectively activated effector T cells secrete IFN-γ.

49. A method of increasing interferon gamma (IFN-γ) in a subject, the method comprising implanting or administering pharmaceutical composition comprising a population of encapsulated cells of any one of embodiments 1-28.

50. A method of treating melanoma in a subject, the method comprising implanting or administering pharmaceutical composition comprising a population of encapsulated cells of any one of embodiments 1-28.

51. The method of any one of embodiments 37-50, wherein encapsulated cells implanted or administered to the subject do not become significantly fibrosed in the subject.

52. The method of embodiment 51, wherein encapsulated cells implanted or administered to the subject do not become fibrosed in the subject.

53. A method of preventing or inhibiting fibrosis of encapsulated cells implanted in a subject, the method comprising having the implanted encapsulated cells express IL-12 or exposing the implanted encapsulated cells to IL-12 in the location of implantation.

54. The method of embodiment 53, wherein the implanted encapsulated cells comprise a population of encapsulated cells of any one of embodiments 1-28 or are implanted in an environment that comprises a population of encapsulated cells expressing IL-12 or are implanted in an environment where IL-12 is present.

55. A method of preparing encapsulated cells producing a recombinant protein, the method comprising:

feeding through a coaxial needle a first composition comprising a polymeric hydrogel and a second composition comprising cells to be encapsulated suspended in a polymeric hydrogel to drop into a crosslinking solution to form the encapsulated cells, wherein the crosslinking solution comprises a sugar alcohol, a buffer, a metal salt, and a surfactant.

56. The method of embodiment 55, wherein the cells to be encapsulated comprise a plurality of oligonucleotide molecules encoding a IL-12 polypeptide.

57. The method of embodiment 56, wherein the IL-12 polypeptide is a native human IL-12 polypeptide, a recombinant IL-12 polypeptide, or an IL-12 mutein polypeptide.

58. The method of any one of embodiment 56 or 57, wherein the native human IL-12 polypeptide is a heterodimeric complex comprising a native human IL-12(p35) polypeptide and a native human IL-12(p40) polypeptide.

59. The method of any one of embodiments 56-58, wherein the plurality of oligonucleotide molecules encodes the native human IL-12(p35) polypeptide and the native human IL-12(p40) polypeptide.

60. The method of any one of embodiments 56-59, wherein the oligonucleotide encoding native the human IL-12(p35) polypeptide comprises a sequence of:

```
                                       (SEQ ID NO: 1)
ATTTCGCTTTCATTTTGGGCCGAGCTGGAGGCGGCGGGGCCGTCCCGGA

ACGGCTGCGGCCGGGCACCCCGGGAGTTAATCCGAAAGCGCCGCAAGCC

CCGCGGGCCGGCCGCACCGCACGTGTCACCGAGAAGCTGATGTAGAGAG

AGACACAGAAGGAGACAGAAAGCAAGAGACCAGAGTCCCGGGAAAGTCC

TGCCGCGCCTCGGGACAATTATAAAAATGTGGCCCCCTGGGTCAGCCTC

CCAGCCACCGCCCTCACCTGCCGCGGCCACAGGTCTGCATCCAGCGGCT

CGCCCTGTGTCCCTGCAGTGCCGGCTCAGCATGTGTCCAGCGCGCAGCC

TCCTCCTTGTGGCTACCCTGGTCCTCCTGGACCACCTCAGTTTGGCCAG

AAACCTCCCCGTGGCCACTCCAGACCCAGGAATGTTCCCATGCCTTCAC

CACTCCCAAAACCTGCTGAGGGCCGTCAGCAACATGCTCCAGAAGGCCA

GACAAACTCTAGAATTTTACCCTTGCACTTCTGAAGAGATTGATCATGA

AGATATCACAAAAGATAAAACCAGCACAGTGGAGGCCTGTTTACCATTG

GAATTAACCAAGAATGAGAGTTGCCTAAATTCCAGAGAGACCTCTTTCA

TAACTAATGGGAGTTGCCTGGCCTCCAGAAAGACCTCTTTTATGATGGC

CCTGTGCCTTAGTAGTATTTATGAAGACTTGAAGATGTACCAGGTGGAG
```

-continued

```
TTCAAGACCATGAATGCAAAGCTTCTGATGGATCCTAAGAGGCAGATCT

TTCTAGATCAAAACATGCTGGCAGTTATTGATGAGCTGATGCAGGCCCT

GAATTTCAACAGTGAGACTGTGCCACAAAAATCCTCCCTTGAAGAACCG

GATTTTTATAAAACTAAAATCAAGCTCTGCATACTTCTTCATGCTTTCA

GAATTCGGGCAGTGACTATTGATAGAGTGATGAGCTATCTGAATGCTTC

CTAAAAAGCGAGGTCCCTCCAAACCGTTGTCATTTTTATAAAACTTTGA

AATGAGGAAACTTTGATAGGATGTGGATTAAGAACTAGGGAGGGGGAAA

GAAGGATGGGACTATTACATCCACATGATACCTCTGATCAAGTATTTTT

GACATTTACTGTGGATAAATTGTTTTTAAGTTTTCATGAATGAATTGCT

AAGAAGGGAAAATATCCATCCTGAAGGTGTTTTTCATTCACTTTAATAG

AAGGGCAAATATTTATAAGCTATTTCTGTACCAAAGTGTTTGTGGAAAC

AAACATGTAAGCATAACTTATTTTAAAATATTTATTTATATAACTTGGT

AATCATGAAAGCATCTGAGCTAACTTATATTTATTTATGTTATATTTAT

TAAATTATTTATCAAGTGTATTTGAAAAATATTTTTAAGTGTTCTAAAA

ATAAAAGTATTGAATTAAAGTGA.
```

61. The method of any one of embodiments 56-60, wherein the oligonucleotide encoding the native human IL-12(p40) polypeptide comprises a sequence of:

```
                                       (SEQ ID NO: 2)
AGAAGAAACAACATCTGTTTCAGGGCCATTGGACTCTCCGTCCTGCCCA

GAGCAAGATGTGTCACCAGCAGTTGGTCATCTCTTGGTTTTCCCTGGTT

TTTCTGGCATCTCCCCTCGTGGCCATATGGGAACTGAAGAAAGATGTTT

ATGTCGTAGAATTGGATTGGTATCCGGATGCCCCTGGAGAAATGGTGGT

CCTCACCTGTGACACCCCTGAAGAAGATGGTATCACCTGGACCTTGGAC

CAGAGCAGTGAGGTCTTAGGCTCTGGCAAAACCCTGACCATCCAAGTCA

AAGAGTTTGGAGATGCTGGCCAGTACACCTGTCACAAAGGAGGCGAGGT

TCTAAGCCATTCGCTCCTGCTGCTTCACAAAAAGGAAGATGGAATTTGG

TCCACTGATATTTTAAAGGACCAGAAAGAACCCAAAAATAAGACCTTTC

TAAGATGCGAGGCCAAGAATTATTCTGGACGTTTCACCTGCTGGTGGCT

GACGACAATCAGTACTGATTTGACATTCAGTGTCAAAAGCAGCAGAGGC

TCTTCTGACCCCCAAGGGGTGACGTGCGGAGCTGCTACACTCTCTGCAG

AGAGAGTCAGAGGGGACAACAAGGAGTATGAGTACTCAGTGGAGTGCCA

GGAGGACAGTGCCTGCCCAGCTGCTGAGGAGAGTCTGCCCATTGAGGTC

ATGGTGGATGCCGTTCACAAGCTCAAGTATGAAAACTACACCAGCAGCT

TCTTCATCAGGGACATCATCAAACCTGACCCACCCAAGAACTTGCAGCT

GAAGCCATTAAAGAATTCTCGGCAGGTGGAGGTCAGCTGGGAGTACCCT

GACACCTGGAGTACTCCACATTCCTACTTCTCCCTGACATTCTGCGTTC

AGGTCCAGGGCAAGAGCAAGAGAGAAAAGAAAGATAGAGTCTTCACGGA

CAAGACCTCAGCCACGGTCATCTGCCGCAAAAATGCCAGCATTAGCGTG

CGGGCCCAGGACCGCTACTATAGCTCATCTTGGAGCGAATGGGCATCTG

TGCCCTGCAGTTAGGTTCTGATCCAGGATGAAAATTTGGAGGAAAAGTG
```

```
-continued
GAAGATATTAAGCAAAATGTTTAAAGACACAACGGAATAGACCCAAAAA

GATAATTTCTATCTGATTTGCTTTAAAACGTTTTTTTAGGATCACAATG

ATATCTTTGCTGTATTTGTATAGTTAGATGCTAAATGCTCATTGAAACA

ATCAGCTAATTTATGTATAGATTTTCCAGCTCTCAAGTTGCCATGGGCC

TTCATGCTATTTAAATATTTAAGTAATTTATGTATTTATTAGTATATTA

CTGTTATTTAACGTTTGTCTGCCAGGATGTATGGAATGTTTCATACTCT

TATGACCTGATCCATCAGGATCAGTCCCTATTATGCAAAATGTGAATTT

AATTTTATTTGTACTGACAACTTTTCAAGCAAGGCTGCAAGTACATCAG

TTTTATGACAATCAGGAAGAATGCAGTGTTCTGATACCAGTGCCATCAT

ACACTTGTGATGGATGGGAACGCAAGAGATACTTACATGGAAACCTGAC

AATGCAAACCTGTTGAGAAGATCCAGGAGAACAAGATGCTAGTTCCCAT

GTCTGTGAAGACTTCCTGGAGATGGTGTTGATAAAGCAATTTAGGGCCA

CTTACACTTCTAAGCAAGTTTAATCTTTGGATGCCTGAATTTTAAAAGG

GCTAGAAAAAAATGATTGACCAGCCTGGGAAACATAACAAGACCCCGTC

TCTACAAAAAAAATTTAAAATTAGCCAGGCGTGGTGGCTCATGCTTGTG

GTCCCAGCTGTTCAGGAGGATGAGGCAGGAGGATCTCTTGAGCCCAGGA

GGTCAAGGCTATGGTGAGCCGTGATTGTGCCACTGCATACCAGCCTAGG

TGACAGAATGAGACCCTGTCTCAAAAAAAAAAATGATTGAAATTAAAAT

TCAGCTTTAGCTTCCATGGCAGTCCTCACCCCCACCTCTCTAAAAGACA

CAGGAGGATGACACAGAAACACCGTAAGTGTCTGGAAGGCAAAAAGATC

TTAAGATTCAAGAGAGAGGACAAGTAGTTATGGCTAAGGACATGAAATT

GTCAGAATGGCAGGTGGCTTCTTAACAGCCCTGTGAGAAGCAGACAGAT

GCAAAGAAAATCTGGAATCCCTTTCTCATTAGCATGAATGAACCTGATA

CACAATTATGACCAGAAAATATGGCTCCATGAAGGTGCTACTTTTAAGT

AATGTATGTGCGCTCTGTAAAGTGATTACATTTGTTTCCTGTTTGTTTA

TTTATTTATTTATTTTTGCATTCTGAGGCTGAACTAATAAAAACTCTTC

TTTGTAATCATA.
```

62. The method of any one of embodiments 56-61, wherein the expressed IL-12(p35) polypeptide and the expressed IL-12(p40) polypeptide form a heterodimeric complex.

63. The method of embodiment 57, wherein the recombinant IL-12 is a heterodimeric complex comprising a recombinant IL-12(p35) polypeptide and a recombinant IL-12(p40) polypeptide.

64. The method of embodiment 63, wherein the plurality of oligonucleotide molecules encodes the recombinant IL-12(p35) polypeptide and the recombinant IL-12(p40) polypeptide.

65. The method of embodiment 57, wherein the IL-12 mutein is a heterodimeric complex comprising an IL-12 (p35) mutein polypeptide and an IL-12(p40) mutein polypeptide.

66. The method of embodiment 65, wherein the plurality of oligonucleotide molecules encodes the IL-12(p35) mutein polypeptide and the IL-12(p40) mutein polypeptide.

67. The method of any one of embodiments 65 or 66, wherein the IL-12(p40) mutein polypeptide comprises a mutation selected from N220L, N222L or N222Q as compared to SEQ ID NO: 4.

68. The method of any one of embodiments 65 or 66, wherein the IL-12(p40) mutein polypeptide comprises a mutation of N222L as compared to SEQ ID NO: 4.

69. The method of any one of embodiments 65 or 66, wherein the IL-12(p40) mutein polypeptide comprises a mutation of N222Q as compared to SEQ ID NO: 4.

70. The method of any one of embodiments 65 or 66, wherein the IL-12(p40) mutein polypeptide comprises a mutation of N220L as compared to SEQ ID NO: 5.

71. The method of any one of embodiments 55-70, wherein the IL-12(p35) and IL-12(p40) polypeptides are expressed at a ratio of 1:1, 1:2, 1:3, 1:4, 1:5, 1:6, 1:7, 1:8, 1:9, or 1:10.

72. The method of any one of embodiments 55-71, wherein the IL-12(p35) and IL-12(p40) polypeptides are expressed at a ratio of 1:3.

73. The method of any one of embodiments 55-72, wherein the cell produces recombinant native human IL-12 heterodimeric protein.

74. The method of any one of embodiments 55-73, wherein the recombinant native human IL-12 protein expressed by the cells comprises a polypeptide comprising a first polypeptide comprising the sequence of:

```
                                          (SEQ ID NO: 3)
MCPARSLLLVATLVLLDHLSLARNLPVATPDPGMFPCLHHSQNLLRAVS

NMLQKARQTLEFYPCTSEEIDHEDITKDKTSTVEACLPLELTKNESCLN

SRETSFITNGSCLASRKTSFMMALCLSSIYEDLKMYQVEFKTMNAKLLM

DPKRQIFLDQNMLAVIDELMQALNFNSETVPQKSSLEEPDFYKTKIKLC

ILLHAFRIRAVTIDRVMSYLNAS;
```
and a second polypeptide comprising the sequence of:

```
                                          (SEQ ID NO: 4)
MCHQQLVISWFSLVFLASPLVAIWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCS;
``` wherein the first and second polypeptide forms a heterodimeric complex.

75. The method of any one of embodiments 37-74, wherein the cells are ARPE-19 cells, ARPE-19-SEAP-2-neo cells, RPE-J cells, hTERT RPE-1 cells, or any combination thereof.

76. The method of any one of embodiments 37-75, wherein the surfactant is TWEEN 20 (polysorbate 20).

77. The method of any one of embodiments 37-76, wherein the buffer is HEPES buffer.

78. The method of any one of embodiments 37-77, wherein the sugar alcohol is mannitol.

79. The method of any one of embodiments 37-78, wherein the metal salt is barium chloride.

80. The method of any one of embodiments 37-79, wherein the method further comprises washing the encapsulated cells in a buffer solution.

81. The method of any one of embodiments 37-80, wherein the method further comprises storing the encapsulated cells in a storage buffer, such as DMEM/F12 cell culture media.

82. The method of embodiment 81, wherein the stored cells retain viability for at least 30 days.

83. The method of embodiments 81 or 82, wherein the storage buffer is substantially free of plasmalyte buffer.

84. A population of encapsulated cells prepared according to a method of any one of embodiments 55-83.

85. A suspension of encapsulated cells, wherein the suspension comprises a population of encapsulated cells of any one of embodiments 1-28, wherein the encapsulated cells are encapsulated by a polymeric hydrogel, and the suspension a crosslinking solution that comprises a sugar alcohol, a buffer, a metal salt, and a surfactant.

86. The suspension of embodiment 85, wherein the cells are ARPE-19 cells, ARPE-19-SEAP-2-neo cells, RPE-J cells, hTERT RPE-1 cells, or any combination thereof.

87. The suspension of embodiments 85 or 86, wherein the surfactant is TWEEN 20 (polysorbate 20).

88. The suspension of any one of embodiments 85-87, wherein the buffer is HEPES buffer.

89. The suspension of any one of embodiments 85-88, wherein the sugar alcohol is mannitol.

90. The suspension of any one of embodiments 85-89, wherein the metal salt is barium chloride.

91. A suspension of encapsulated cells, wherein the suspension comprises a population of encapsulated cells of any one of embodiments 1-28, wherein the encapsulated cells are encapsulated by a polymeric hydrogel, and a storage buffer, such as DMEM/F12 cell culture media.

92. The suspension of embodiment 91, wherein the suspended encapsulated cells retain viability for at least 30 days.

93. The suspension of any one of embodiments 85-92, wherein the suspension buffer is substantially free of plasmalyte buffer.

H. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain alike or similar result without departing from the spirit and scope of the disclosure.

Example 1. Encapsulated Cells are Non-Tumorigenic

Implantable cells can become tumorigenic, thus it is important to demonstrate the inability of the encapsulated cells to become tumorigenic or divide uncontrollably. The cells that were used, ARPE-19 cells, were selected because it is non-tumorigenic, displays contact-inhibited growth characteristics in 2D culture, is amendable to genetic modification, and has shown to be safe in prior clinical studies. In order to assess ARPE-19 cell fate after encapsulation various assays were performed to analyze the viability and proliferation of the encapsulated ARPE-19 cells within the capsules. These studies demonstrated that encapsulated ARPE-19 cells exhibited the desired characteristics including viability in culture for at least 4 weeks, expansion in 2D culture, and contact inhibition upon encapsulation, preventing further cell growth within the capsules. Briefly, the LIVE/DEAD Viability/Cytotoxicity Kit was used to assess ARPE-19 viability within encapsulation over time in vitro to quickly discriminate live cells from dead cells by simultaneously staining with green-fluorescent stain to indicate intracellular esterase activity (live cells) and red-fluorescent ethidium homodimer-1 (dead cells) to indicate loss of plasma membrane integrity. Proliferation of the cells within the capsules was measured using Click-iT EdU imaging kit. A 1× working solution of EdU diluted in media was added to each capsule. At 0, 24, 72 hours, and 7 days, the media was removed and capsules were fixed in 4% PFA. Capsules were washed with 3% BSA, and permeabilized using 0.5% Triton X-100. To stain the cells, 0.2 ml of the Click-iT reaction cocktail was added to each capsule and incubated for 30 minutes. The capsules were subsequently washed with 3% BSA. Lastly, cell nuclei were stained using Hoechst 33343 (NucBlu). Capsules were imaged using an EVOS XL microscope at 4× magnification.

First, the inventors assessed the viability of the encapsulated ARPE-19 using live/dead stain by fluorescence microscopy. They observed no differences in the number of encapsulated viable ARPE-19 cells in vitro over the 28-day period. Next, they investigated the proliferation status of ARPE-19 cells. An in vitro assessment of the capsules was conducted to compare proliferation of encapsulated ARPE cells with cells known to exhibit continued in vitro proliferation within alginate hydrogels (HEK cells). ARPE cells (or HEK cells as a control) were encapsulated into 1.5 mm alginate capsules and imaged in vitro over time for up to 7 days. At discreet time points, capsules were pulled from the main population at random and assayed qualitatively using DAPI staining to visualize the cells within the capsules and EdU (GFP) as a proliferation marker. Images were taken at 4× magnification. Only the HEK cells stained with the GFP marker, confirming that the ARPE-19 cells do not proliferate after encapsulation within the alginate hydrogels (data not shown). This observation was confirmed using PCR analysis. In conclusion, in vitro the encapsulated ARPE-19 remained viable for at least 28 days. The encapsulated ARPE-19 cell line could be expanded in 2D culture but exhibited contact inhibition upon encapsulation and thus did not continue expanding inside of the capsules. This feature is critical for regulating the dose of cytokine secretion per capsule post administration.

Example 2. Preparation of Encapsulated Cells

Polyclonal ARPE-19 cells were expanded and transfected using a lipofectamine protocol with a ratio of 5:1 (transposase:transposon) to create cells expressing human native IL-12. Transfected cells were cultured and plated at 0.5 cells/well for single cell outgrowth, although if a polyclonal sample of cells, which could be used, the concentration can be different. IL-12 production of the selected clone was about ~3.8 PCD (picograms/cell/day). The clone was expanded in cell flasks/stacks for up to two weeks before being harvested into a cell pellet and suspended in alginate (SLG20) for encapsulation. The encapsulation process comprises loading two syringes, one with SLG20, and one with the cell pellet (10.5 million cells/mL) suspended in alginate (SLG20). The syringes were fed into a coaxial needle through use of a power supply (electric current) allowing droplets to fall into a crosslinking bath, which contained mannitol, barium chloride, HEPES buffer and Tween 20, which was where the capsules take shape.

Capsules were collected from the bath after sitting in the bath for 5 minutes and washed 8 times at a 1:25 ratio of capsules to HEPES buffer solution (2 minutes/wash) to help to help remove loosely bound barium. The encapsulated cells were stored in DMEM/F12 cell culture media at ambient temperature in a container, such as a conical tube, biotainer bottle, or other sterile container.

Example 3. RPE-mIL12 Capsules Eradicate Pancreatic Cancer in Less than 10 Days of Treatment PAN02-Fluc cells ($5 \times 10^6$) were injected in IP space of B6 albino mice to establish IP PAN02 tumors. At 7 days post injection, mice were randomly divided into groups of 8 and treated with 20 RPE capsules (~30 k cells/cap), sham surgery, or 20 RPE-mIL12 capsules (~30 k cells/cap, ~400 ng mIL-12/day). At 25 days post treatment, mice were sacrificed, and liver, kidney, abdominal wall, spleen, and tumors were examined ex vivo using IVIS imaging. Analysis showed no positive IVIS signal at 10 or 25 days post treatment in RPE-mIL12 treated mice.

Example 4. RPE-mIL12 Capsules Exhibit Reduced Fibrosis Over Time

Pan02-Fluc cells ($5 \times 106$) suspended in HBSS were injected into the IP space of albino B6 mice (mixed gender). Six days after IP injections, mice were imaged via IVIS and stratified into 4 groups of 5-6 mice. Seven days after IP injections, mice were treated with either 1) untreated, 2) 200 RPE capsules, 3) 200 RPE-mIL2 capsules (7000 ng mIL2/day), 4) 10 RPE-mIL12 capsules (~200 ng mIL12/day). All capsules were administered via surgical implantation. Five days after capsule implantation, mice were imaged via IVIS in order to visualize extent of IP tumor burden. Seven days after capsule implantation, mice were sacrificed, and IP cells were collected using 10 mL PBS wash. Cell suspension was filtered using a 70 um filter and spun down using a centrifuge (2000 rpm, 4 min). Supernatant was discarded, and 3 mL RBC lysis buffer was added for 10 min at room temperature. 10 mL of PBS+2% FBS was added to each tube. Cells were spun down (5000 rpm, 10 min). Supernatant was discarded, and cell pellet was resuspended in 2 mL complete media (DME/F12+10% FBS+1% AntiAnti). Individual samples in each group were pooled. Cells were spun down (2000 rpm, 10 min). Supernatant was discarded, cells were resuspended in FC block on ice for 10 min and then spun down (2000 rpm, 10 min). Cells were stained with CD45 antibody for 30 min on ice and then spun down (2000 rpm, 10 min). Supernatant was discarded, and cells were resuspended in 4 mL complete media. Cells were stained with ReadiDrop propidium iodide and sorted (PI-CD45+). Sorted cells were processed, library prepared, and sequenced at BCM core. Visual analysis, and analysis of CSF1R and FN1 macrophage markers showed that RPE-mIL12 capsules displayed minimal fibrotic overgrowth at 7 days post treatment, while RPE and RPE-mIL2 capsules showed extensive overgrowth. Accordingly, the expression of IL-12 from the capsules, which was only difference between the capsules, appears to inhibit fibrotic overgrowth. This was a surprising result because it was accomplished without modifying the alginate with an anti-fibrotic compound or modification.

Example 5. Treatment with RPE-mIL12 Capsules Lead to Increased Expression of CD8a, PRF1, and IFN-γ

Pan02-Fluc cells ($5 \times 106$) suspended in HBSS were injected into the IP space of albino B6 mice (mixed gender). Six days after IP injections, mice were imaged via IVIS and stratified into 4 groups of 5-6 mice. Seven days after IP injections, mice were treated with either 1) untreated, 2) 200 RPE capsules, 3) 200 RPE-mIL2 capsules (~7000 ng mIL2/day), 4) 10 RPE-mIL12 capsules (~200 ng mIL12/day). All capsules were administered via surgical implantation. Five days after capsule implantation, mice were imaged via IVIS in order to visualize extent of IP tumor burden. Seven days after capsule implantation, mice were sacrificed, and IP cells were collected using PBS wash. Cell suspension was filtered using a 70 um filter and spun down using a centrifuge (2000 rpm, 4 min). Supernatant was discarded, and 3 mL RBC lysis buffer was added for min at room temperature. 10 mL of PBS+2% FBS was added to each tube. Cells were spun down (5000 rpm, 10 min). Supernatant was discarded, and cell pellet was resuspended in 2 mL complete media (DME/F12+10% FBS+1% AntiAnti). Individual samples in each group were pooled. Cells were spun down (2000 rpm, 10 min). Supernatant was discarded, cells were resuspended in FC block on ice for 10 min and then spun down (2000 rpm, 10 min). Cells were stained with CD45 antibody for 30 min on ice and then spun down (2000 rpm, 10 min). Supernatant was discarded, and cells were resuspended in 4 mL complete media. Cells were stained with ReadiDrop propidium iodide and sorted (PI-CD45+). Sorted cells were processed, library prepared, and sequenced at BCM core. The data showed that mice treated with RPE-mIL12 exhibited expression of CD8a, PRF1, and IFN-γ, relative to the untreated or RPE treated mice. The data further showed that local high dose RPE-mIL2 did not cause increased FoxP3 expression, a marker of Tregs, while RPE-mIL12 treatment caused increased IFN-γ expression.

Example 6. Subcutaneous or Intraperitoneal Administration of RPE-mIL12 Delays Subcutaneous Tumor Growth in B16F10 Melanoma Model B16F10 ($5 \times 10^5$) cells suspended in HBSS were injected subcutaneously into the right flank of B6 mice (mixed gender). Six days after IP injections, tumors were measured using a digital caliper and stratified into 4 groups of 3-4 mice. Seven days after IP injections, mice were treated with either 1) sham surgery, 2) 10 RPE-mIL12 capsules implanted subcutaneously, 3) 10 RPE-mIL12 capsules implanted in IP cavity, 4) 10 RPE-mIL12 capsules+5 freeze thawed B16F10 capsules (antigens) implanted in the IP cavity. All capsules were administered via surgical implantation. In order to prepare the antigens, B16F10 melanoma cells were encapsulated into alginate capsules and subjected to 3 rounds of freezing/thawing cycles at −80 C to disrupt the cells. At the time of administration, antigen capsules were thawed and administered along with 10 RPE-mIL12 capsules in the IP space of mice bearing subcutaneous B16F10 tumors. After capsule administration, tumors were measured every 2-4 days until tumors reached 15 mm in any direction. Treatment with RPE-mIL12 capsules or RPE-mIL12 capsules co-administered with antigens increased survival and delayed tumor growth, as illustrated in FIG. 1.

Figure 2:
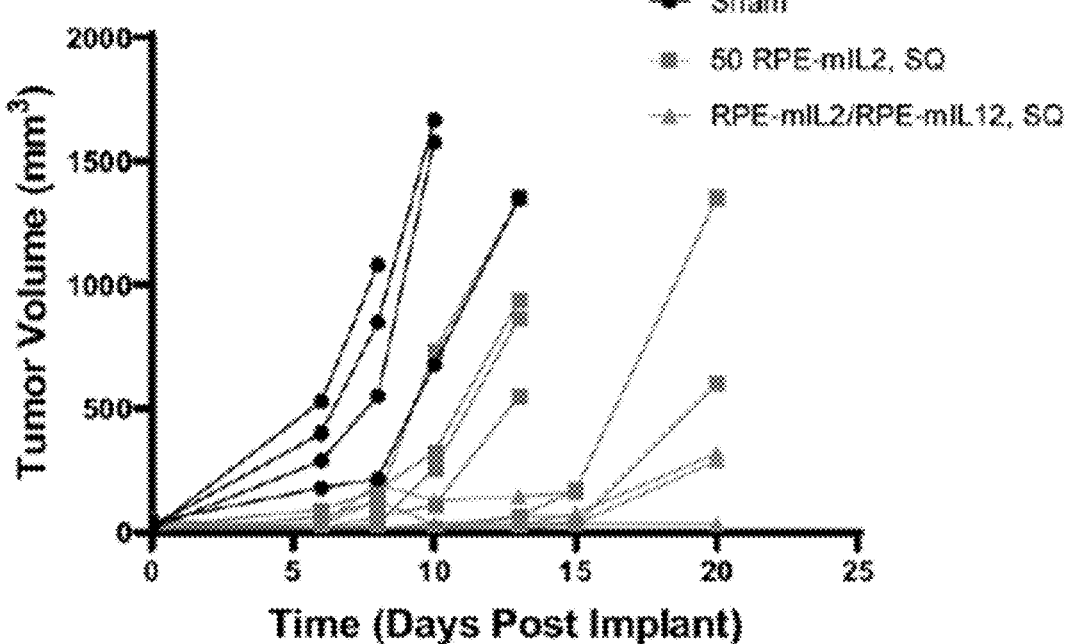
FIG. 2 illustrates tumor growth curves for melanoma B16F10 mice threated subcutaneously with the encapsulated cells disclosed herein or sham surgery.

Example 7. Simultaneous Administration of RPE-mIL2 and RPE-mIL12 Delays Subcutaneous Tumor Growth in B16F10 Melanoma Model B16F10 ($5\times10^5$) cells suspended in HBSS were injected subcutaneously into the right flank of B6 mice (male). Six days after subcutaneous injections, tumors were measured using a digital caliper and stratified into 3 groups of mice. Seven days after subcutaneous injections, mice were treated with either RPE-mIL2 capsules, RPE-mIL2 capsules co-administered with or RPE-mIL12 capsules. Treatment with RPE-mIL2 capsules, RPE-mIL2 capsules co-administered with or RPE-mIL12 capsules delayed tumor growth, as illustrated in FIG. 2.

Example 8. RPE-mIL12 Capsules Caused KPC Pancreatic Tumor Reduction in Less than 1 Week of Treatment without Recurrence KPC-Fluc cells ($1\times10^6$) were injected in IP space of B6 mice to establish IP KPC tumors. At 7 days post injection, 15 mice were stratified into 3 groups and treated with 3 RPE-mIL12 capsules (~30 k cells/cap, ~60 ng mIL-12/day), 10 RPE-mIL12 capsules (~30 k cells/cap, ~200 ng mIL-12/day) or 15 RPE-mIL12 capsules (~30 k cells/cap, ~300 ng mIL-12/day). IVIS analysis at days 6, 14, and 21 following treatment showed KPC pancreatic tumor reduction. Mice treated with 3 RPE-mIL12 capsules (~30 k cells/cap, ~60 ng mIL-12/day), 10 RPE-mIL12 capsules (~30 k cells/cap, ~200 ng mIL-12/day) were further observed up until day 180 and showed no tumor recurrence. Analysis of internal organs at day 180 following treatment showed no increase in vascularization or discoloration as observed in untreated KPC tumor control mice.

Example 9. Cytokine Factories Reduce Pancreatic Cancer Tumor Burden in Less than 7 Days of Treatment PAN02-Fluc cells (5×10 6) were injected in IP space of B6 albino mice to establish IP PAN02 Fluc tumors. At 7 days post injection, mice were stratified into groups of 5-6 and treated with untreated, 200 RPE capsules (~30 k cells/cap), 200 RPE-mIL2 capsules (~30 k cells/cap, ~7000 ng mIL-2/day) or 10 RPE-mIL12 capsules (~30 k cells/cap, ~200 ng mIL-12/day). Seven days post treatment, mice were sacrificed, and IP fluid was processed for single cell RNAseq. IVIS analysis at day 5 following treatment showed KPC pancreatic tumor reduction in mice treated with RPE-mIL2 or RPE-mIL12 capsules. Analysis of immune cell populations via RNAseq showed relative reduction in B cell, and dendritic cell numbers in mice treated with RPE-mIL2 or RPE-mIL12 capsules compared to untreated mice, and increase in monocytes or NK/T-cells.

Figure 3A:
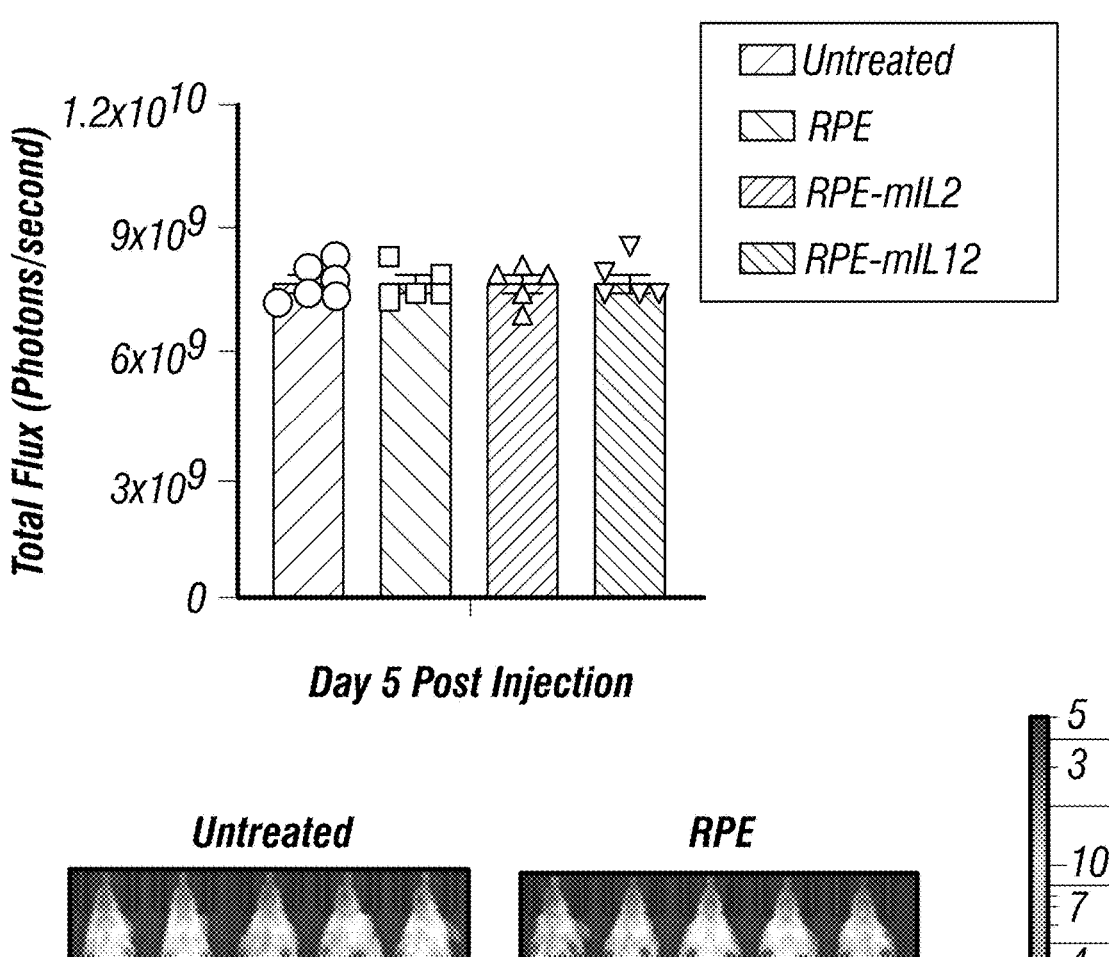
FIG. 3A, upper panel, shows quantification of total flux from IVIS images taken 6 days after injection of Pan02-fluc cells in all mice (n=5-6 per group) before treatment. Lower panel shows luminescent images of mice five days after control (untreated), RPE, RPE-mIL2, or RPE-mIL12 treatment.
Figure 3A:
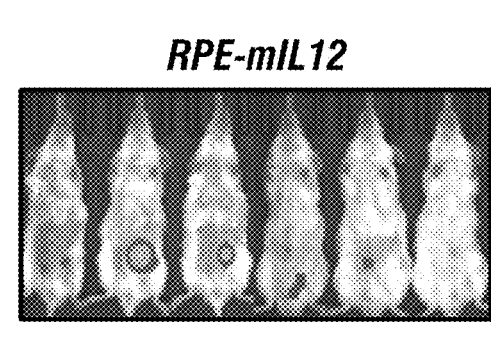
Figure 3A:
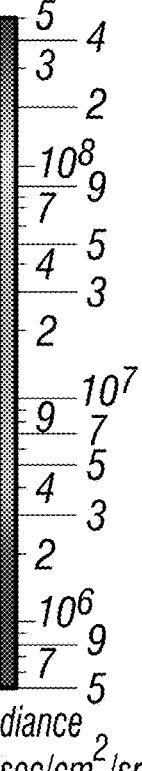
Figure 3B:
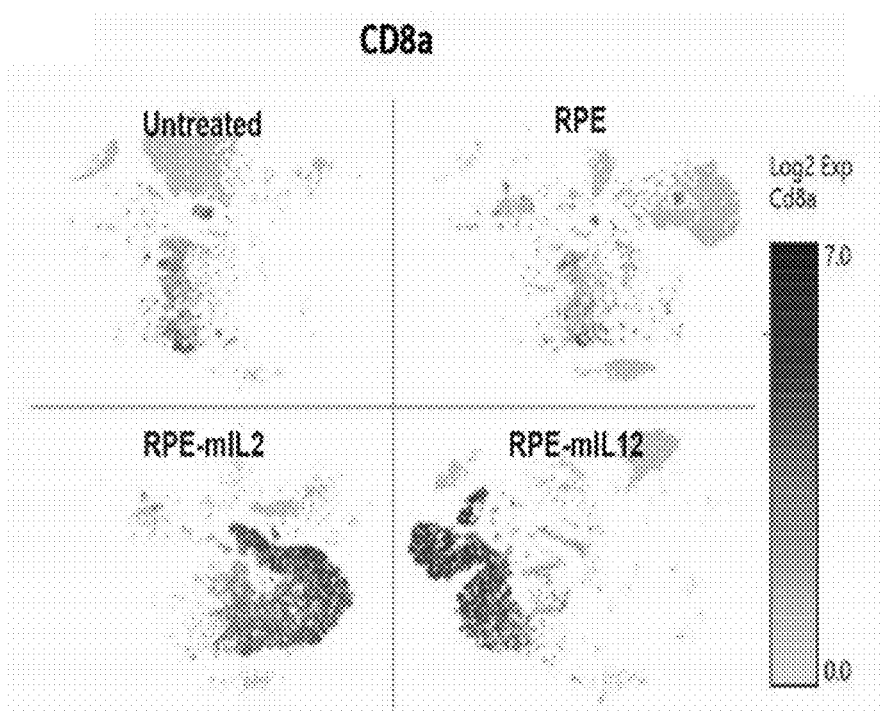
FIG. 3B, upper panel, shows t-SNE plots of CD8a gene expression in individuals cells separated by treatment (untreated, RPE, RPE-mIL2, RPEmIL12) collected from the IP space one week of treatment. Lower panel shows t-SNE plots of IFNg gene expression in individuals cells separated by treatment (untreated, RPE, RPE-mIL2, RPE-mIL12) collected from the IP space one week of treatment.
Figure 3B:
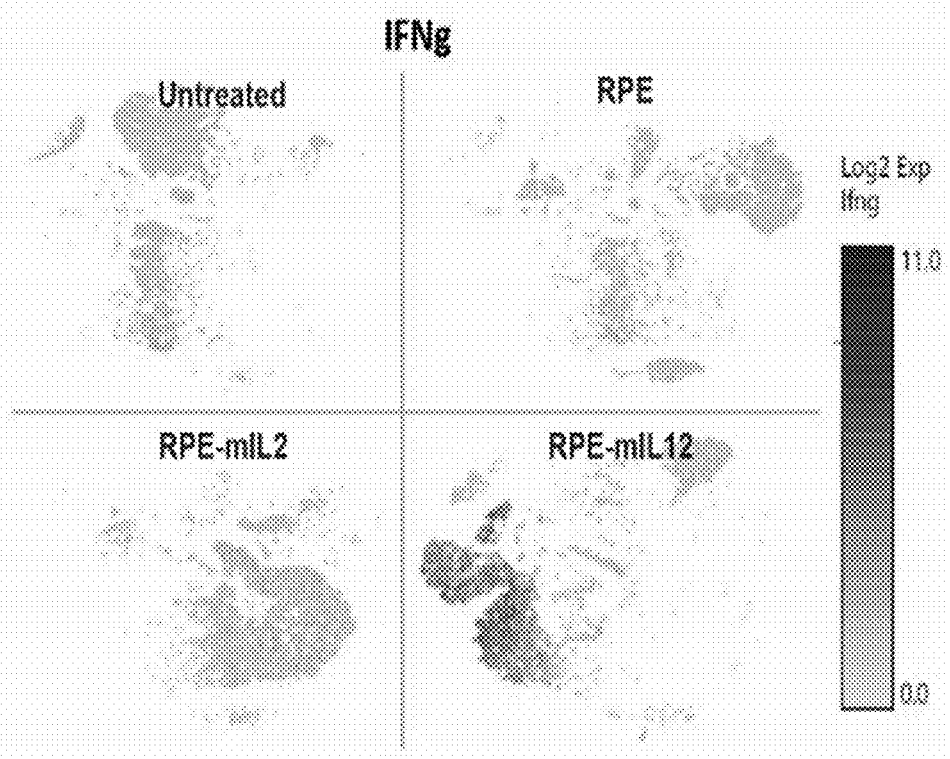

Example 10. Cytokine Factories Reduce Pancreatic Cancer Tumor Burden in 5 Days of Treatment Mice (n=5-6 per group) were injected with Pan02-fluc cells (5×10 6) before treatment. As shown in FIG. 3A, upper panel, IVIS imaging showed stable levels of total flux six days after injection. Five days following control (untreated), RPE, RPE-mIL2, or RPE-mIL12 treatment, as shown in FIG. 3A, lower panel, luminescent imaging showed reduced tumor burden. Scale bar minima and maxima of average radiances (photons/sec/cm2/ser) were 5×105 and 5×108 respectively. Next, individuals cells separated by treatment (untreated, RPE, RPE-mIL2, RPE-mIL12) were collected from the IP space after one week of treatment and CD8a gene expression was assessed. t-SNE plot embedding of CD8a gene expression shows increased expression following RPE-mIL2 or RPE-mIL12 treatment (FIG. 3B, upper panel, heat map represented log 2 scaled expression of CD8a in cells). t-SNE plot embedding of IFNg gene expression in individuals cells separated by treatment (untreated, RPE, RPE-mIL2, RPE-mIL12) collected from the IP space one week of treatment showed increased IFNg expression following RPE-mIL2 or RPE-mIL12 treatment (FIG. 3B, lower panel, heat map represented log 2 scaled expression of IFNg in cells).

Figure 4A:
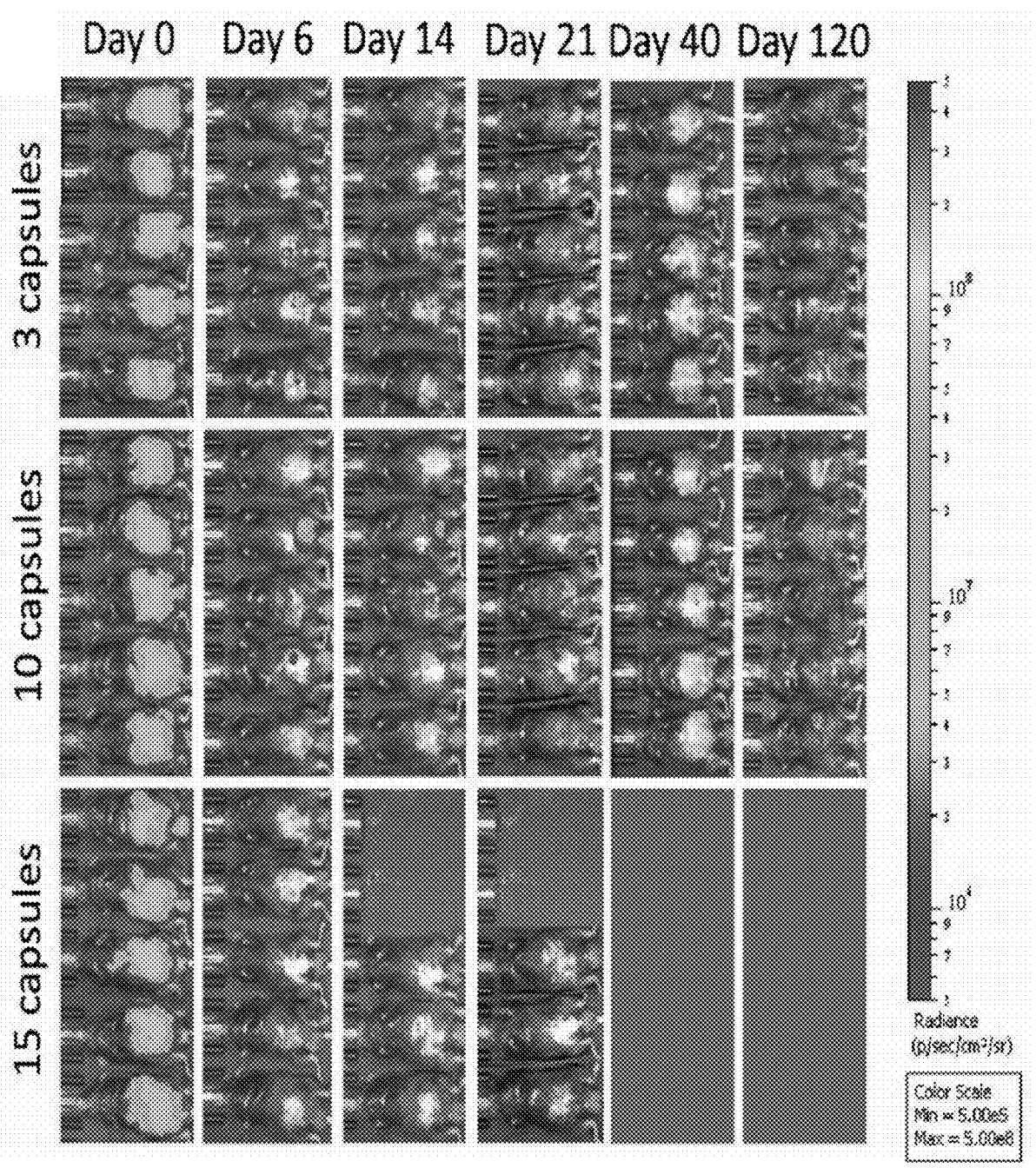
FIG. 4A shows luminescent images of mice over time after varying doses of RPE-mIL12 treatment. Scale bar minima and maxima of average radiances (photons/sec/cm2/ser) are 5×105 and 5×108, respectively.
Figure 4B:
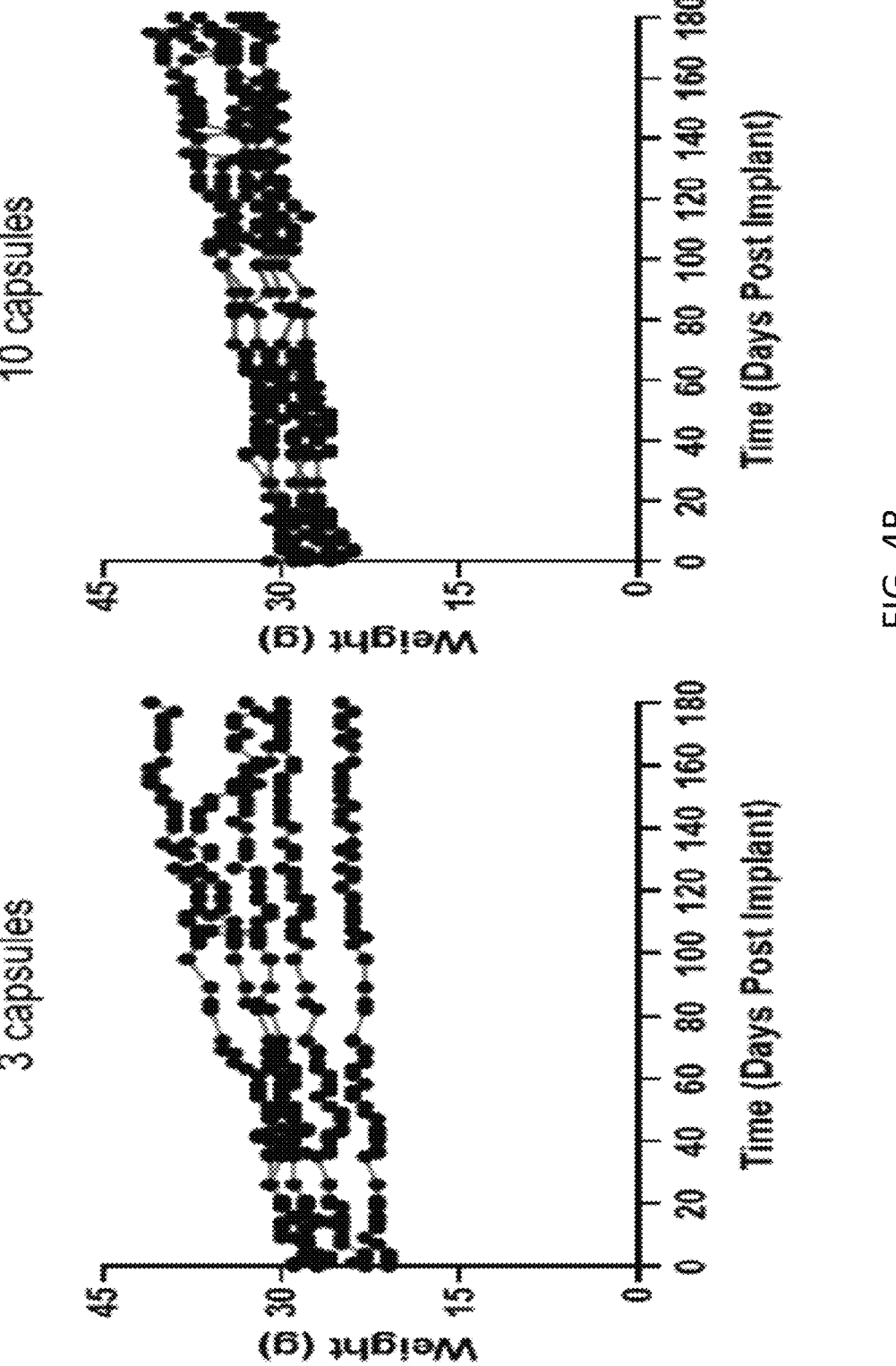
FIG. 4B illustrates individual animal weight over time for animals treated with 3 or 10 RPE-mIL12 capsules.
Figure 4C:
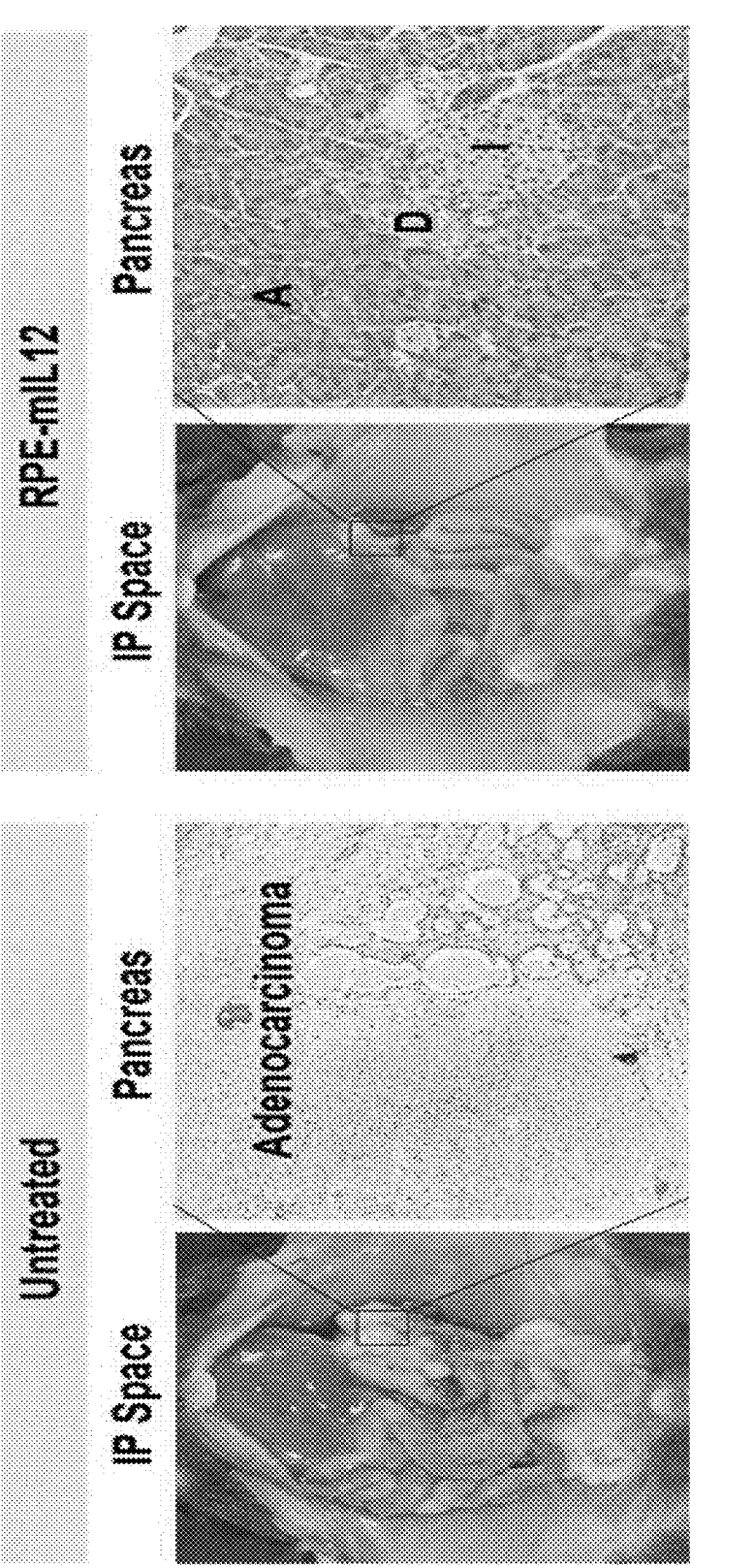
FIG. 4C shows macroscopic and H&E images of the IP space and the pancreas, respectively, 8 weeks post treatment with or with RPE-mIL12. H&E images are 20× magnification. A denotes acinar cells, D denotes ducts and I denotes Islet of Langerhans.

Example 11. RPE-mIL12 Capsules Produced a Long Lasting Reduction of Pancreatic Cancer Tumor Burden KPC cells ($1\times10^6$) were injected in IP space of mice to establish IP KPC tumors. At 7 days post injection, mice were stratified into 3 groups and treated with 3 RPE-mIL12 capsules, 10 RPE-mIL12 capsules, or 15 RPE-mIL12 capsules. IVIS analysis at days 6, 14, 21, 40, and 120 following treatment showed KPC pancreatic tumor reduction (FIG. 4A). Furthermore, gradual increase in weight was observed in animals treated with 3 or 10 RPE-mIL12 capsules up until day 180 following treatment (FIG. 4B). Macroscopic and hematoxylin and eosin imaging of pancreas at 8 weeks following treatment with or without RPE-mIL12 showed that pancreas of animals treated with RPE-mIL12 capsules displayed preserved cellular morphology and structure (FIG. 4C).

Figure 5:
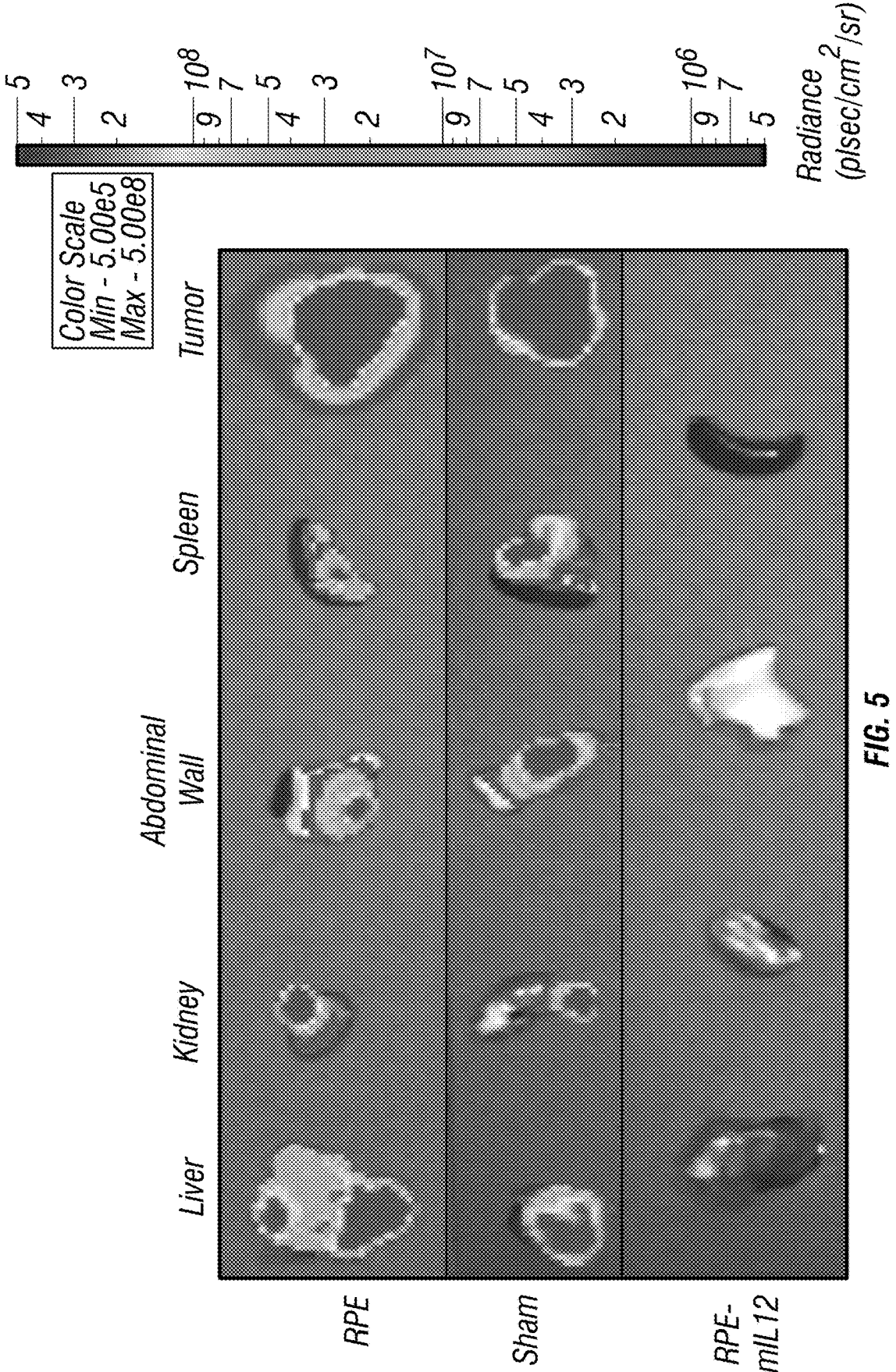
FIG. 5 shows luminescent images of intraperitoneal organs explanted from mice over time days after treatment with sham surgery, RPE, or RPE-mIL12 treatment. Scale bar minima and maxima of average radiances (photons/sec/cm2/ser) are 5×105 and 5×108, respectively.

Example 12. RPE-mIL12 Capsules Reduced Pancreatic Cancer Tumor Burden in Liver, Kidney, Abdominal Wall, and Spleen As provided in the examples above, mice were injected with Pan02-fluc cells ($5\times10^6$) before treatment. Mice were subjected to sham treatment, RPE treatment, or RPE-mIL12 treatment 7 days following injection with the pancreatic cancer cells. At 25 days following treatment, liver, kidney, abdominal wall, and spleen were extracted from mice. Luminescent imaging showed no pancreatic cancer tumor in liver, kidney, abdominal wall, or spleen of animals treated with RPE-mIL12 capsules (FIG. 5).

Figure 6A:
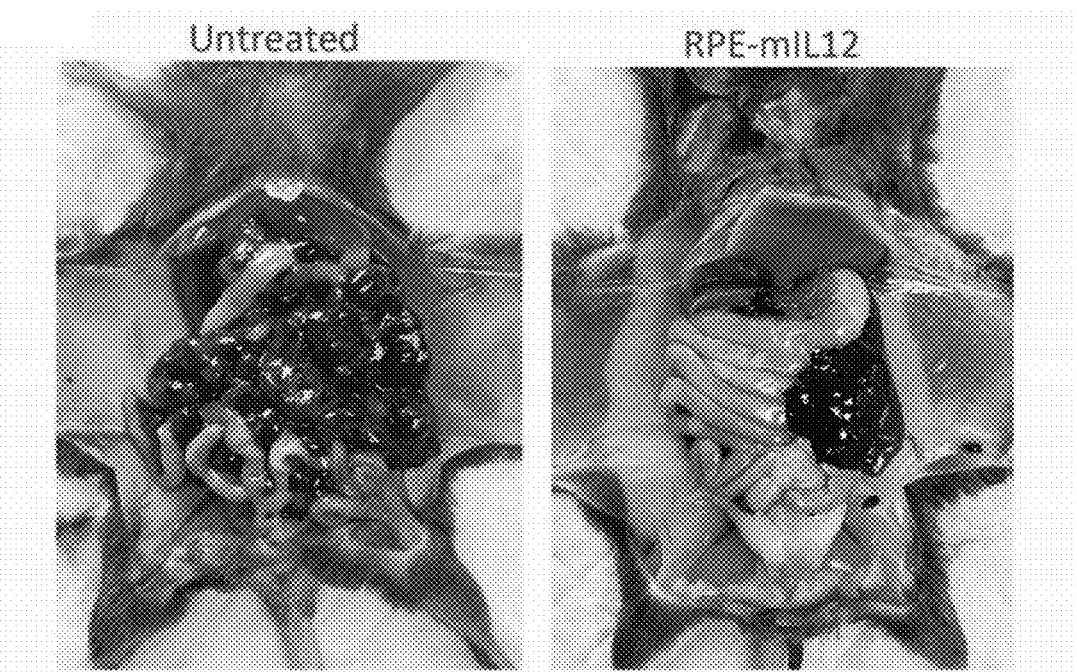
FIG. 6A shows macroscopic images of mice with metastatic melanoma in the IP space one week after treatment with or without RPE-mIL12.
Figure 6B:
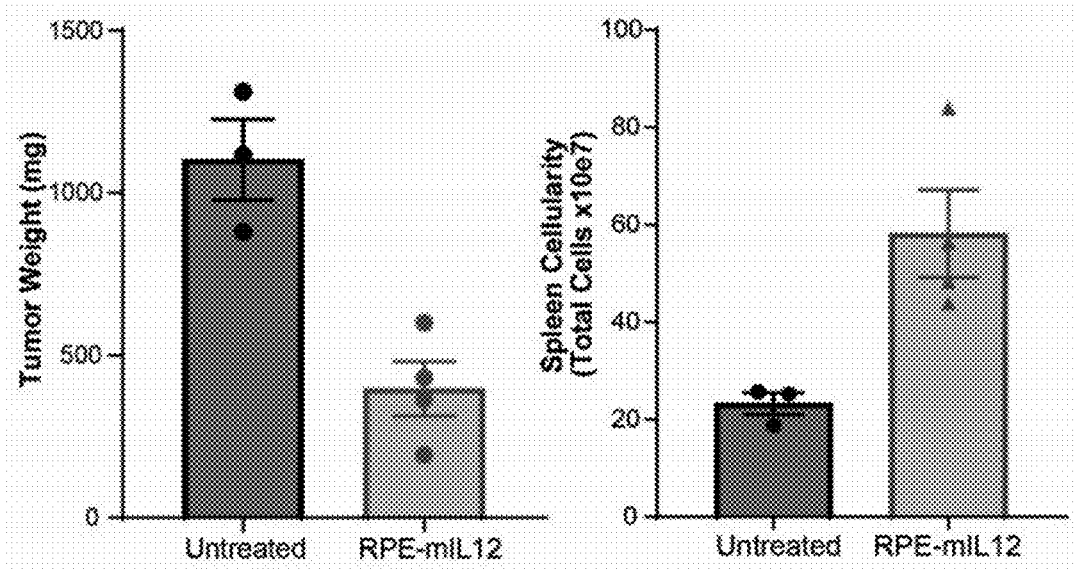
FIG. 6B illustrates splenic cellularity one week after treatment with or without RPE-mIL12.

Example 13. Administration of RPE-mIL12 Reduced Tumor Growth and Preserves Splenic Cellularity in Melanoma Model Melanoma cells ($5\times10^5$) cells were injected into the IP space of mice. Seven days after melanoma cell injections, mice were untreated (control), or treated with RPE-mIL2 capsules. Treatment with RPE-mIL12 capsules resulted in a reduced tumor growth, as shown in FIG. 6A (n=3-4 per group). Next, spleens were extracted and dissociated into single cell suspensions for automated cell counting. Treatment with RPE-mIL12 capsules resulted in preserved splenic cellularity, as shown in FIG. 6B.

Figure 7:
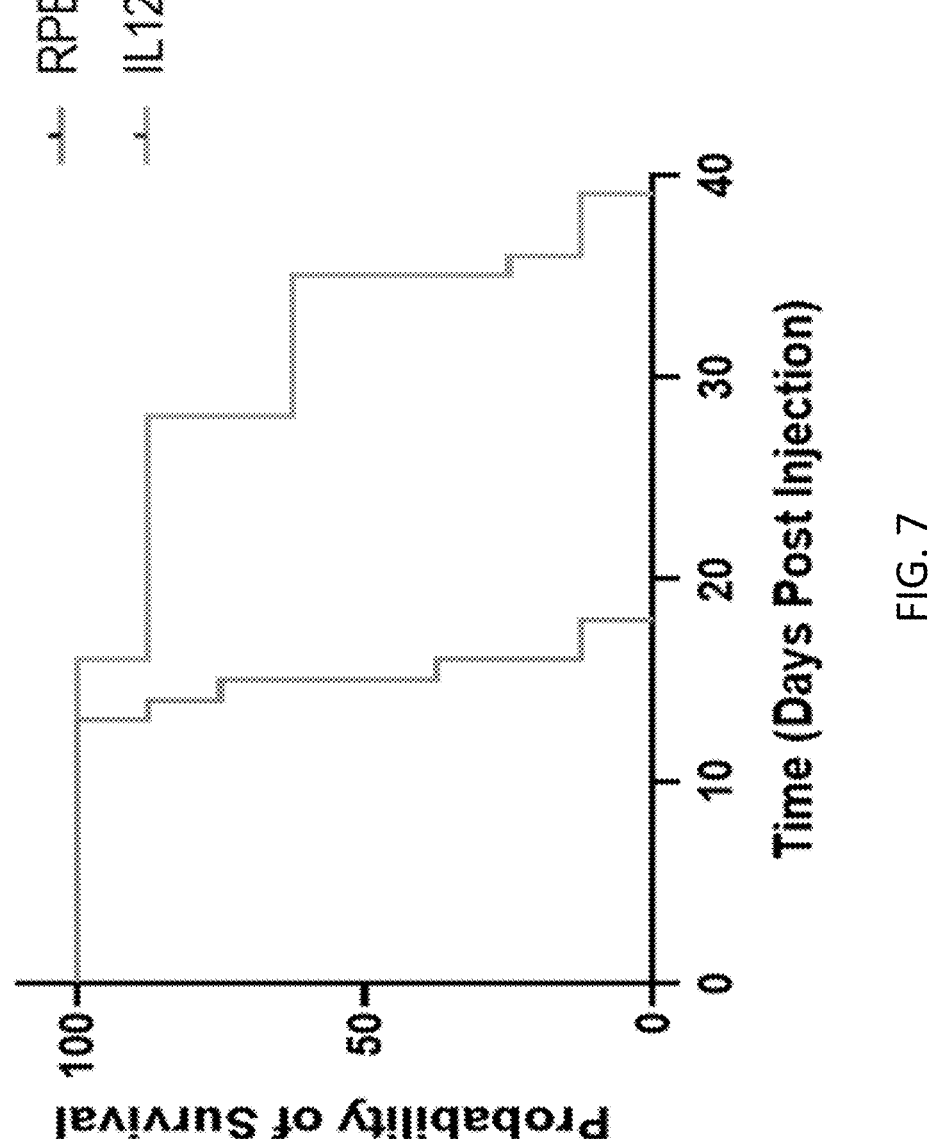
FIG. 7 illustrates survival curves of animals with melanoma tumors following treatment with RPE or RPE-mIL12 capsules.

Example 14. Administration of RPE-mIL12 Increased Survival of Animals with Melanoma Tumors Melanoma cells (5×10 5) cells were injected into the IP space of mice. Seven days after melanoma cell injections, mice (n=4-6 mice per group) were treated with RPE capsules, or RPE-mIL2 capsules. Treatment with RPE-mIL12 capsules resulted in an increased probability of survival, as shown in FIG. 7.

Figure 8:
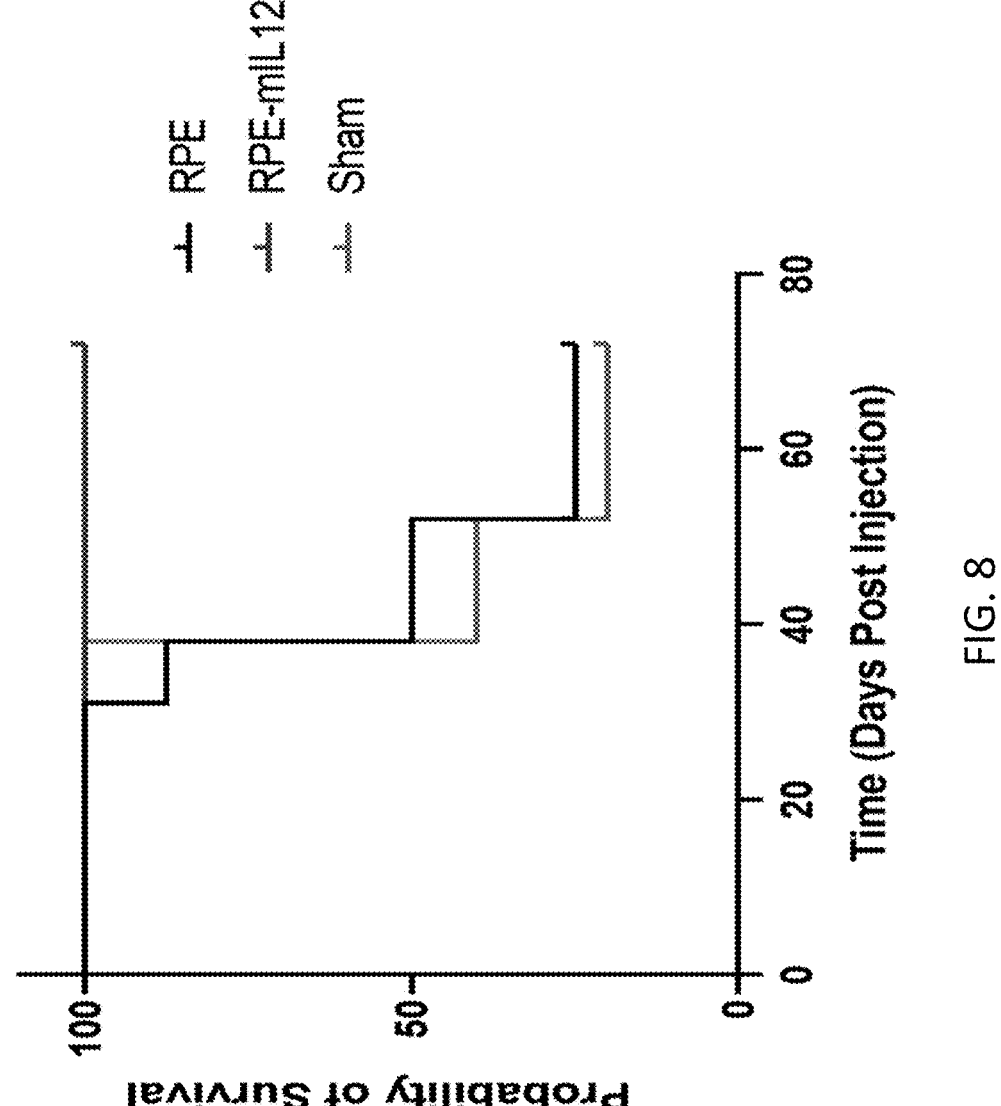
FIG. 8 illustrates survival curves of animals with pancreatic tumors following sham treatment, or treatment with RPE or RPE-mIL12 capsules.

Example 15. Administration of RPE-mIL12 Increased Survival of Animals with Pancreatic Tumors Pan02-fluc cells (5×10 6) cells were injected into the IP space of mice. Seven days after melanoma cell injections, mice (n=5-8 mice per group) were subjected to sham surgery (control), treated with RPE capsules, or treated with RPE-mIL2 capsules. Treatment with RPE-mIL12 capsules resulted in an increased probability of survival, as shown in FIG. 8, while control or RPE treated animals showed lesser probability of survival.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed:

1. A population of encapsulated cells comprising a plurality of oligonucleotide molecules encoding a IL-12 polypeptide, wherein the native human IL-12 polypeptide is a heterodimeric complex comprising a native human IL-12 (p35) polypeptide and a native human IL-12 (p40) polypeptide, further wherein the IL-12 (p35) polypeptide and the IL-12 (p40) polypeptide is expressed at a ratio (IL-12 (p35):IL-12 (p40)) of about 1:1, 1:2, 1:3, 1:4, 1:5, 1:6, 1:7, 1:8, 1:9, or 1:10.

2. The population of encapsulated cells of claim 1, wherein the IL-12 polypeptide is a native human IL-12 polypeptide, a recombinant IL-12 polypeptide, or a IL-12 mutein polypeptide.

3. The population of encapsulated cells of claim 2, wherein the recombinant IL-12 is a heterodimeric complex comprising a recombinant IL-12 (p35) polypeptide and a recombinant IL-12 (p40) polypeptide.

4. The population of encapsulated cells of claim 2, wherein the IL-12 mutein is a heterodimeric complex comprising an IL-12 (p35) mutein polypeptide and an IL-12 (p40) mutein polypeptide.

5. The population of encapsulated cells of claim 4, wherein the IL-12 (p40) mutein polypeptide comprises a mutation selected from N220L, N222L or N222Q as compared to the amino acid sequence of SEQ ID NO: 4.

6. The population of encapsulated cells of claim 1, wherein the plurality of oligonucleotide molecules encodes the native human IL-12 (p35) polypeptide and the native human IL-12 (p40) polypeptide.

7. The population of encapsulated cells claim 1, wherein the oligonucleotide encoding the native human IL-12 (p35) polypeptide comprises a sequence of SEQ ID NO: 1 and the oligonucleotide encoding the native human IL-12 (p40) polypeptide comprises a sequence of SEQ ID NO: 2.

8. The population of encapsulated cells of any one of claim 1, wherein the expressed IL-12 (p35) polypeptide and the expressed IL-12 (p40) polypeptide form a heterodimeric complex.

9. The population of encapsulated cells of claim 1, wherein the population of cells produces about 10 to about 50, about 10 to about 30, about 10 to about 20, or about 20 nanograms/cell/day of native human IL-12.

10. The population of encapsulated cells of claim 1, wherein the cells are ARPE-19 cells, ARPE-19-SEAP-2-neo cells, RPE-J cells, hTERT RPE-1 cells, or any combination thereof.

11. The population of encapsulated cells of claim 1, wherein the cells are encapsulated with a polymeric hydrogel.

12. The population of encapsulated cells claim 11, wherein the polymeric hydrogel comprises chitosan, cellulose, hyaluronic acid, or alginate.

13. The population of encapsulated cells of claim 11, wherein the cells remain viable for at least 5, 10, 15, 20, 40, 120, or 180 days.

14. The population of encapsulated cells of claim 1, wherein the encapsulated cells do not proliferate.

15. The population of encapsulated cells of claim 1, wherein the capsule encapsulating the population of cells does not develop fibrotic overgrowth or develops partial fibrotic overgrowth after implantation in a subject.

16. A pharmaceutical composition comprising the population of encapsulated cells of claim 1.

17. The pharmaceutical composition of claim 16, further comprising a population of encapsulated cells comprising an oligonucleotide molecule encoding native human IL-2.

18. A method of:

treating a tumor or cancer, in a subject, the method comprising implanting in the intraperitoneal space of the subject a pharmaceutical composition comprising a plurality of encapsulated cells of claim 1 to treat the tumor or the cancer in the subject;

reducing tumor burden, in a subject, the method comprising implanting in the intraperitoneal space of the subject a pharmaceutical composition comprising a plurality of encapsulated cells of claim 1 to the subject to reduce the tumor burden in the subject;

treating a tumor, or reducing tumor burden, in a subject by generating memory immunity, the method comprising implanting in, or administering to, the subject a pharmaceutical composition comprising the population of encapsulated cells of claim 1 in the subject;

selectively activating CD8 positive effector T cells in a subject, the method comprising implanting in, or administering to, the subject a pharmaceutical composition comprising a population of encapsulated cells of claim 1 in the subject;

increasing interferon gamma (IFN-γ) in a subject, the method comprising implanting in, or administering to, the subject pharmaceutical composition comprising a population of encapsulated cells of claim 1 in the subject;

preventing or inhibiting fibrosis of a capsule encapsulating cells implanted in a subject, the method comprising having the implanted encapsulated cells express IL-12 or exposing the implanted encapsulated cells to IL-12 at the location of implantation.

\* \* \* \* \*